(12) United States Patent
Shaughnessy et al.

(10) Patent No.: US 7,668,659 B2
(45) Date of Patent: Feb. 23, 2010

(54) DIAGNOSIS AND CLASSIFICATION OF MULTIPLE MYELOMA

(75) Inventors: John D. Shaughnessy, Little Rock, AR (US); Bart Barlogie, Little Rock, AR (US); Fenghuang Zhan, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 153 days.

(21) Appl. No.: 10/289,746

(22) Filed: Nov. 7, 2002

(65) Prior Publication Data

US 2003/0175753 A1    Sep. 18, 2003

Related U.S. Application Data

(60) Provisional application No. 60/403,075, filed on Aug. 13, 2002, now abandoned, provisional application No. 60/355,386, filed on Feb. 8, 2002, now abandoned, provisional application No. 60/348,238, filed on Nov. 7, 2001, now abandoned.

(51) Int. Cl.
  *G01N 33/48* (2006.01)
  *C12Q 1/68* (2006.01)
  *C07H 21/04* (2006.01)

(52) U.S. Cl. .............................. 702/19; 702/20; 435/6; 536/24.1

(58) Field of Classification Search ........................ None
  See application file for complete search history.

(56) References Cited

OTHER PUBLICATIONS

Darnell, et al. Molecular cell Biology, p. 107-108, 1986.*
Dorland's Medical Dictionary, definition for "ex vivo," printed from the internet at http://www.mercksource.com/pp/us/cns/cns_hl_dorlands_split.jsp?pg=/ppdocs/us/common/dorlands/dorland/three/000038060.htm on May 9, 2008.*
Ng, R. T. et al. *Hierarchical Cluser Analysis of SAGE Data for Cancer Profiling: BIOKDD,* Aug. 26, 2001, pp. 65-72.
Duggan, D. J. et al. *Expression Profiling Using cDNA Microarrays: Nature Genetics Supplement,* Jan. 1999, vol. 21, pp. 10-14.
Shaughnessy, J. D. et al.; *Integrating Cytogenetics and Gene Expression Profiling in the Molecualar Analysis of Multiple Myeloma: In. Journal of Hematolgy.,* 2002 vol. 76, pp. 59-64.
Eisen, M. B. et al.; *Cluster Analysis and Display of Genome-Wide Expression Patterns: Proc. Natl. Acad. Sci.,* Dec. 1998, vol. 95, pp. 14863-14868.
Claudio, J. O. et al.; *A Molecular Compendium Of Genes Expressed in Multiple Myeloma:Blood,* Sep. 2002 vol. 100, No. 6, pp. 2175-2186.
Vos, J. D. et al.; *Identifying Intercellular Signaling Genes Expressed in Malignant Plasma Cells by Using Complementary DNA arrays: Blood,* Aug. 1, 2001 vol. 98, No. 3, pp. 771-780.

* cited by examiner

*Primary Examiner*—Shubo (Joe) Zhou
(74) *Attorney, Agent, or Firm*—Benjamin Aaron Adler

(57) ABSTRACT

Gene expression profiling between normal B cells/plasma cells and multiple myeloma cells revealed four distinct subgroups of multiple myeloma plasma cells that have significant correlation with clinical characteristics known to be associated with poor prognosis. Diagnosis for multiple myeloma (and possibly monoclonal gammopathy of undetermined significance) based on differential expression of 14 genes, as well as prognostics for the four subgroups of multiple myeloma based on the expression of 24 genes were also established. Gene expression profiling also allows placing multiple myeloma into a developmental schema parallel to that of normal plasma cell differentiation. The development of a gene expression- or developmental stage-based classification system for multiple myeloma would lead to rational design of more accurate and sensitive diagnostics, prognostics and tumor-specific therapies for multiple myeloma.

4 Claims, 19 Drawing Sheets

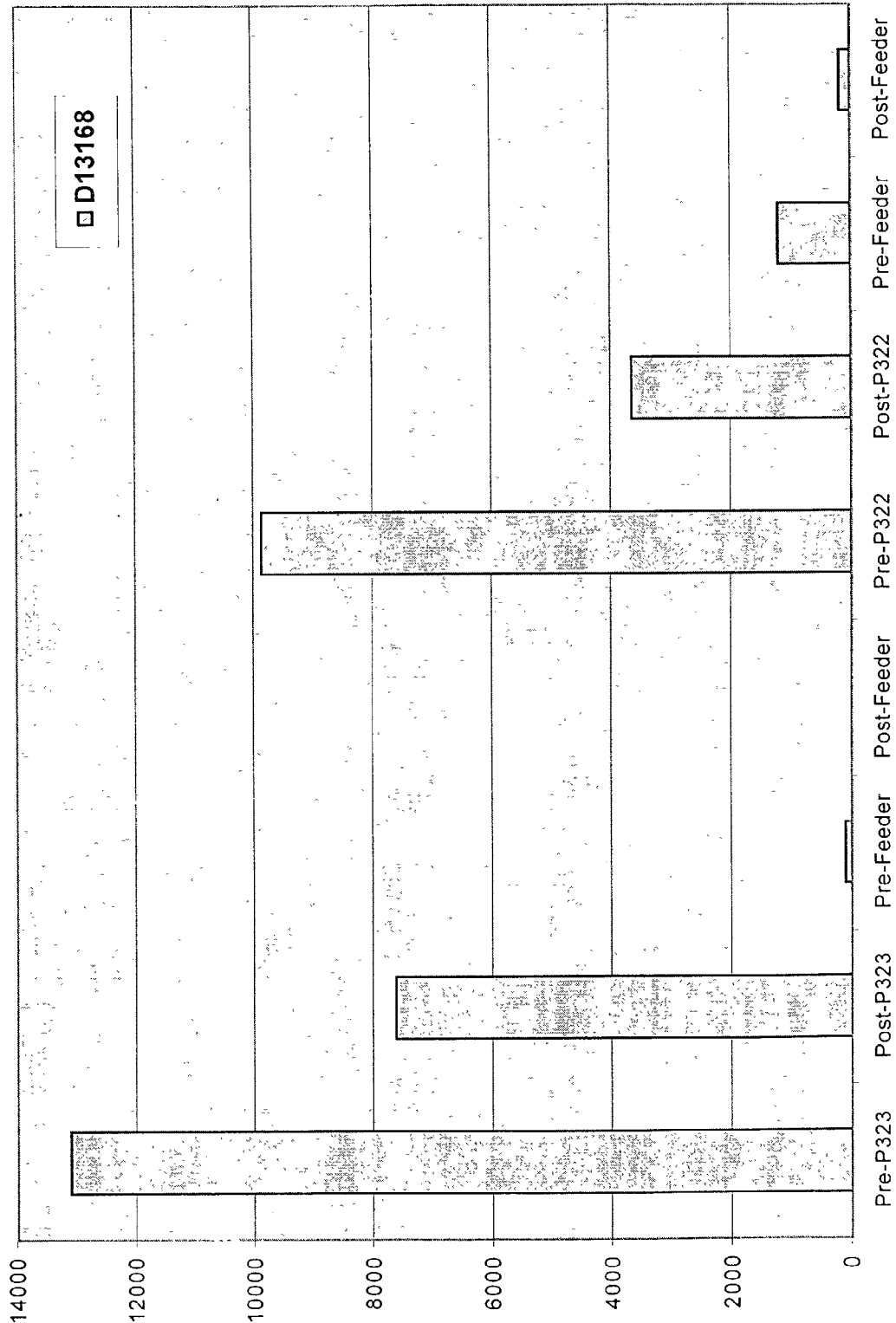

DIAGNOSIS AND CLASSIFICATION OF MULTIPLE MYELOMA

CROSS-REFERENCE TO RELATED APPLICATION

This non-provisional patent application claims benefit of provisional patent application Nos. 60/348,238, filed Nov. 7, 2001, now abandoned, 60/355,386, filed Feb. 8, 2002, now abandoned and 60/403,075, filed Aug. 13, 2002, now abandoned.

FEDERAL FUNDING LEGEND

This invention was produced in part using funds obtained through a grant from the National Cancer Institute. Consequently, the federal government has certain rights in this invention.

BACKGROUND OF THE INVENTION

1. Field of the Invention

The present invention relates generally to the field of cancer research. More specifically, the present invention relates to gene expression profiling of plasma cells from normal individual and patients with multiple myeloma and monoclonal gammopathy of undetermined significance.

2. Description of the Related Art

Multiple myeloma (MM) is a uniformly fatal tumor of terminally differentiated plasma cells (PCs) that home to and expand in the bone marrow. Although initial transformation events leading to the development of multiple myeloma are thought to occur at a post-germinal center stage of development as suggested by the presence of somatic hypermutation of IGV genes, progress in understanding the biology and genetics of and advancing therapy for multiple myeloma has been slow.

Multiple myeloma cells are endowed with a multiplicity of anti-apoptotic signaling mechanisms that account for their resistance to current chemotherapy and thus the ultimately fatal outcome for most patients. While aneuploidy by interphase fluorescence in situ hybridization (FISH) and DNA flow cytometry are observed in >90% of cases, cytogenetic abnormalities in this typically hypoproliferative tumor are informative in only about 30% of cases and are typically complex, involving on average 7 different chromosomes. Given this "genetic chaos" it has been difficult to establish correlations between genetic abnormalities and clinical outcomes. Only recently has chromosome 13 deletion been identified as a distinct clinical entity with a grave prognosis. However, even with the most comprehensive analysis of laboratory parameters, such as $\beta$2-microglobulin ($\beta$2M), C-reactive protein (CRP), plasma cell labeling index (PCLI), metaphase karyotyping, and FISH, the clinical course of patients afflicted with multiple myeloma can only be approximated, because no more than 20% of the clinical heterogeneity can be accounted for. Thus, there are distinct clinical subgroups of multiple myeloma and modern molecular tests may identify these entities.

Monoclonal gammopathy of undetermined significance (MGUS) and multiple myeloma are the most frequent forms of monoclonal gammopathies. Monoclonal gammopathy of undetermined significance is the most common plasma cell dyscrasia with a n incidence of up to 10% of population over age 75. The molecular basis of monoclonal gammopathy of undetermined significance and multiple myeloma are not very well understood and it is not easy to differentiate the two disorders. The diagnosis of multiple myeloma or monoclonal gammopathy of undetermined significance is identical in ⅔ of cases using classification systems that are based on a combination of clinical criteria such as the amount of bone marrow plasmocytosis, the concentration of monoclonal immunoglobulin in urine or serum, and the presence of bone lesions. Especially in early phases of multiple myeloma, the differential diagnosis is associated with a certain degree of uncertainty.

Furthermore, in the diagnosis of multiple myeloma, the clinician must exclude other disorders in which a plasma cell reaction may occur such as rheumatoid arthritis and connective tissue disorders, or metastatic carcinoma where the patient may have osteolytic lesions associated with bone metastases. Therefore, given that multiple myeloma is thought to have an extended latency and clinical features are recognized many years after the development of the malignancy, new molecular diagnostic techniques are needed in screening for the disease and provide differential diagnosis for multiple myeloma, e.g., monoclonal gammopathy of undetermined significance versus multiple myeloma or the recognition of various subtypes of multiple myeloma.

Thus, the prior art is deficient in methods of differential diagnosing and identifying distinct and prognostically relevant clinical subgroups of multiple myeloma. The present invention fulfills this long-standing need and desire in the art.

SUMMARY OF THE INVENTION

Bone marrow plasma cells from 74 patients with newly diagnosed multiple myeloma, 5 with monoclonal gammopathy of undetermined significance (MGUS), and 31 normal volunteers (normal plasma cells) were purified by $CD138^+$ selection. Gene expression of purified plasma cells and 7 multiple myeloma cell lines were profiled using high-density oligonucleotide microarrays interrogating ~6,800 genes. On hierarchical clustering analysis, normal and multiple myeloma plasma cells were differentiated and four distinct subgroups of multiple myeloma (MM1, MM2, MM3 and MM4) were identified. The expression patterns of MM1 was similar to normal plasma cells and monoclonal gammopathy of undetermined significance, whereas MM4 was similar to multiple myeloma cell lines. Clinical parameters linked to poor prognosis such as abnormal karyotype (P=0.0003), and high serum $\beta$2-microglobulin levels (P=0.0004) were most prevalent in MM4. Genes involved in DNA metabolism and cell cycle control were overexpressed in a comparison of MM1 and MM4.

Using chi square and Wilcoxon rank sum tests, 120 novel candidate disease genes that discriminated between normal and malignant plasma cells (P<0.0001) were identified. Many of these candidate genes are involved in adhesion, apoptosis, cell cycle, drug resistance, growth arrest, oncogenesis, signaling and transcription. In addition, a total of 156 genes, including FGFR3 and CCND1; exhibited highly elevated ("spiked") expression in at least 4 of the 74 multiple myeloma cases (range of spikes: 4 to 25). Elevated expression of FGFR3 and CCND1 were caused by the translocation t(4;14)(p16;q32) or t(11;14)(q13;q32).

The present invention also identifies, through multivariate stepwise discriminant analysis, a minimum subset of genes whose expression is intimately associated with the malignant features of multiple myeloma. Fourteen genes were defined as predictors that are able to differentiate plasma cells of multiple myeloma patients from normal plasma cells with a high degree of accuracy, and 24 genes were identified as predictors that are able to differentiate the distinct subgroups of multiple myeloma (MM1, MM2, MM3 and MM4) described herein.

Furthermore, data disclosed herein indicated that multiple myeloma can be placed into a developmental schema parallel to that of normal plasma cell differentiation. Based on gene expression profiling, the MM4, MM3 and MM2 subgroups described above were found to have similarity with tonsil B cells, tonsil plasma cells and bone marrow plasma cells respectively. These data suggest that the enigmatic multiple myeloma is amendable to a gene expression/development stage-based classification system.

In one aspect of the present invention, there are provided methods of using DNA microarray and hierarchical clustering analysis to classify subgroups of multiple myeloma, identify genes with elevated expression in subsets of multiple myeloma patients, and identify potential therapeutic targets for multiple myeloma.

In another aspect of the present invention, there are provided methods of identifying groups of genes that can either differentiate plasma cells of multiple myeloma patients from normal plasma cells, or distinguish between distinct subgroups of multiple myeloma.

In still another aspect of the present invention, there are provided methods of diagnosis for multiple myeloma, or subgroups of multiple myeloma based on the expression of a group of 14 genes or a group of 24 genes respectively.

In yet another aspect of the present invention, there are provided methods of treatment for multiple myeloma. Such methods involve inhibiting or enhancing the expression of genes that are found to be over-expressed or down-regulated respectively in multiple myeloma patients as disclosed herein.

The present invention also provides a method of developmental stage-based classification for multiple myeloma that is based on gene expression profiling between multiple myeloma cells and normal B or plasma cells.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 9A shows the expression of endothelin B receptor (ENDBR) in feeder cells and myeloma cells P323 and P322 before and after co-culture.

CD19-Selected Tonsil B cells: Tonsil-derived mononuclear fractions were tested for percentage of tonsil B cells prior to anti-CD19 immunomagnetic bead sorting by using two-color FACs analysis with antibodies to CD20/CD38 (a and b). The post-sorting purity of the tonsil B cell sample was determined by CD20/CD38 (c and d), CD138/CD20 (e), and CD138/CD38 (f) staining. Cytospin preparations of the purified tonsil B cell samples were stained with Wright Giemsa and cell morphology observed with light microscopy (g). Purifed B cells were also stained with AMCA and FITC antibodies against cytoplasmic immunoglobulin (cIg) light chain (κ and λ) and observed by immunofluorescence microscopy (h). Note the lack of cIg staining and thus minimal plasma cell contamination in the tonsil B cell fraction.

CD138-Selected Tonsil Plasma Cells: Tonsil mononuclear fractions were tested for percentage of plasma cells prior to anti-CD138 immunomagnetic bead sorting by using two color FACs analysis using antibodies to CD38/CD45 (i) and CD138/CD45 (j). The post-sorting purity of the tonsil plasma cell samples was determined by dual color FACs analysis of CD38/CD45 (k), CD138/CD45 (1), CD38/CD20 (m), and CD138/CD38 (n). Cytospin preparations of the purified tonsil plasma cells were analyzed for morphological appearance (O) and cIg (p).

CD138-Selected Bone Marrow Plasma Cells: Mononuclear fractions from bone marrow aspirates were tested for percentage of plasma cells prior to anti-CD138 immunomagnetic bead sorting b y using two color FACs analysis using antibodies to CD38/CD45 (q) and CD138/CD45 (r). The post sorting purity of the bone marrow plasma cell sample was determined by dual color FACs analysis of CD38/CD45 (s), CD138/CD45 (t), CD38/CD20 (u), and CD138/CD38 (v). Cytospin preparations of the purified bone marrow plasma cells were analyzed for morphological appearance (w) and cIg (x). Note the high percentage of cIg-positive bone marrow plasma cells with clear plasma cell morphologic characteristics.

Figure 11:
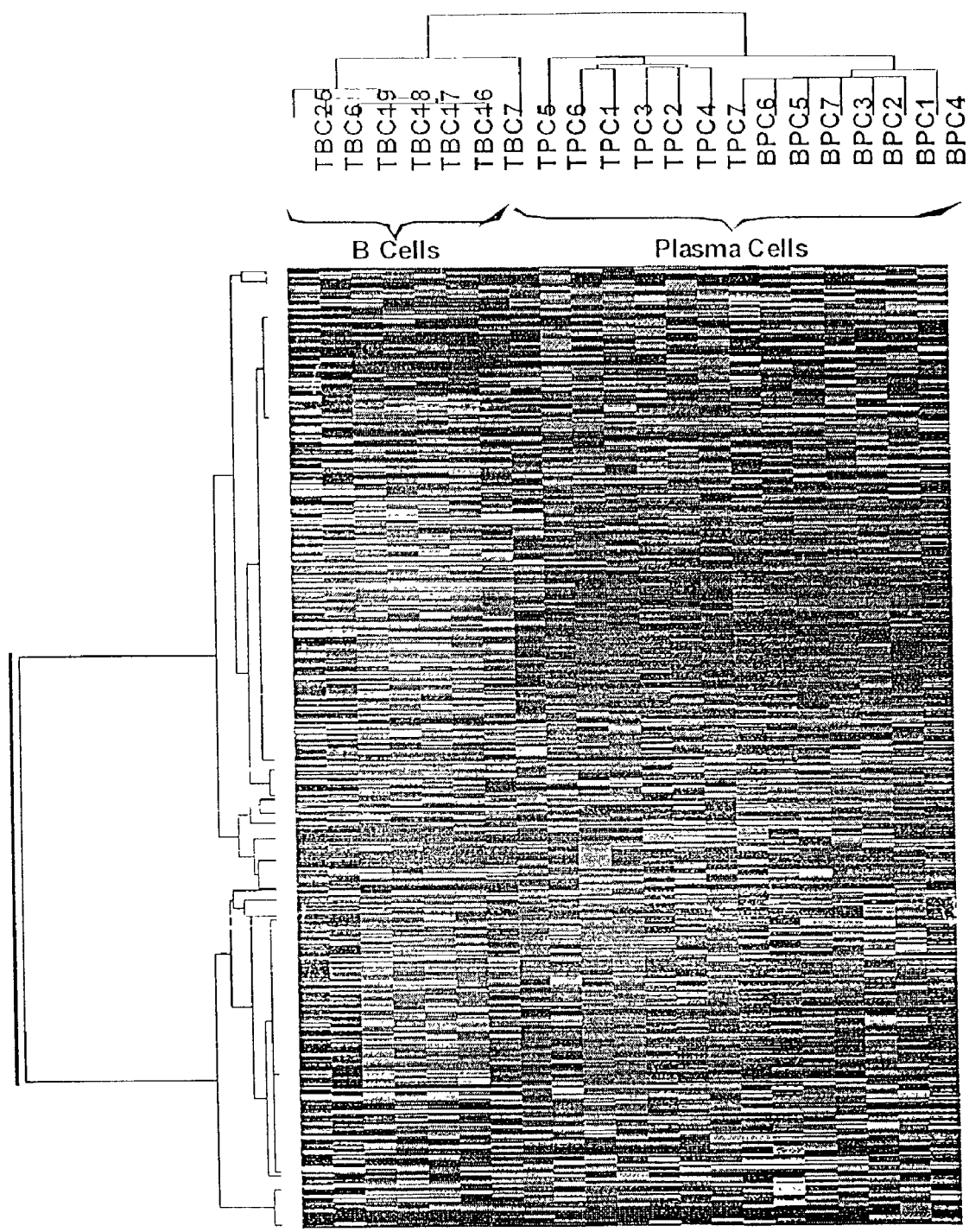

FIG. 11 shows two-dimensional hierarchical cluster analysis of normal human plasma cells. Included were 7 tonsil BC (TBC), 7 tonsil PC (TPC), and 7 bone marrow PC (BPC) samples clustered based on the correlation of experimental expression profiles of 4866 probe sets. The clustering is presented graphically as a colored image. Along the vertical axis, the analyzed genes are arranged as ordered by the clustering algorithm. The genes with the most similar patterns of expression are placed adjacent to each other. Experimental samples are similarly arranged in the horizontal axis. The color of each cell in the tabular image represents the expression level of each gene, with red representing an expression greater than the mean, green representing an expression less than the mean, and the deeper color intensity representing a greater magnitude of deviation from the mean. The top dendrogram produces two major branches separating tonsil BCs from PCs. In addition, within the PC cluster, tonsil PCs and bone marrow PCs are separated on three unique branches.

Figure 12:
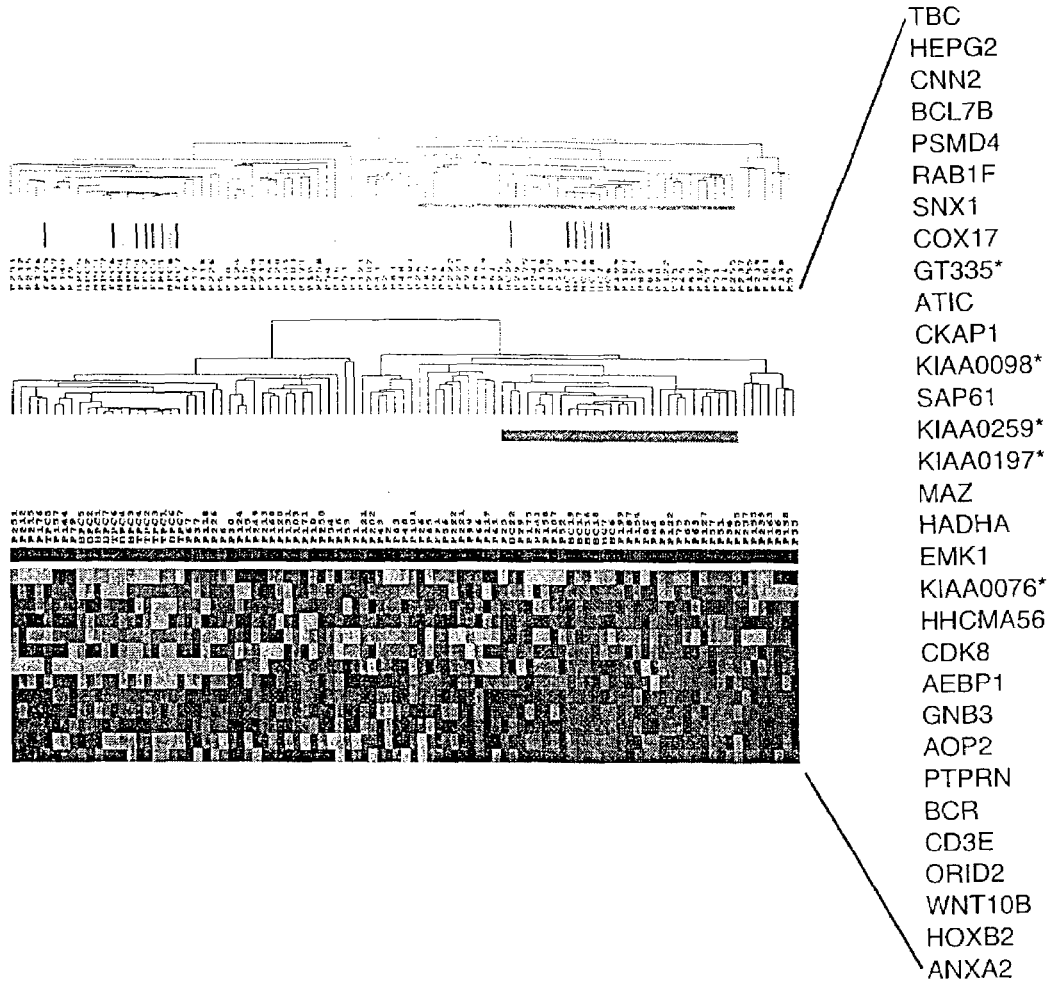

FIG. 12 shows two-dimensional hierarchical cluster analysis of experimental expression profiles and gene behavior of 30 EDG-MM. B cells, tonsil and bone marrow plasma cells, and multiple myeloma (MM) samples were analyzed using a cluster-ordered data table. The tonsil B cell, tonsil plasma cell, bone marrow plasma cell samples are indicated by red, blue, and golden bars respectively. The nomenclature for the 74 MM samples is as indicated in Zhan et al. (2002). Along the vertical axis, the analyzed genes are arranged as ordered by the clustering algorithm. The genes with the most similar patterns of expression are placed adjacent to each other. Both sample and gene groupings can be further described by following the solid lines (branches) that connect the individual components with the larger groups. The tonsil B cell cluster is identified by the horizontal red bar. The color of each cell in the tabular image represents the expression level of each gene, with red representing an expression greater than the mean, green representing an expression less than the mean, and the deeper color intensity representing a greater magnitude of deviation from the mean.

Figure 13:
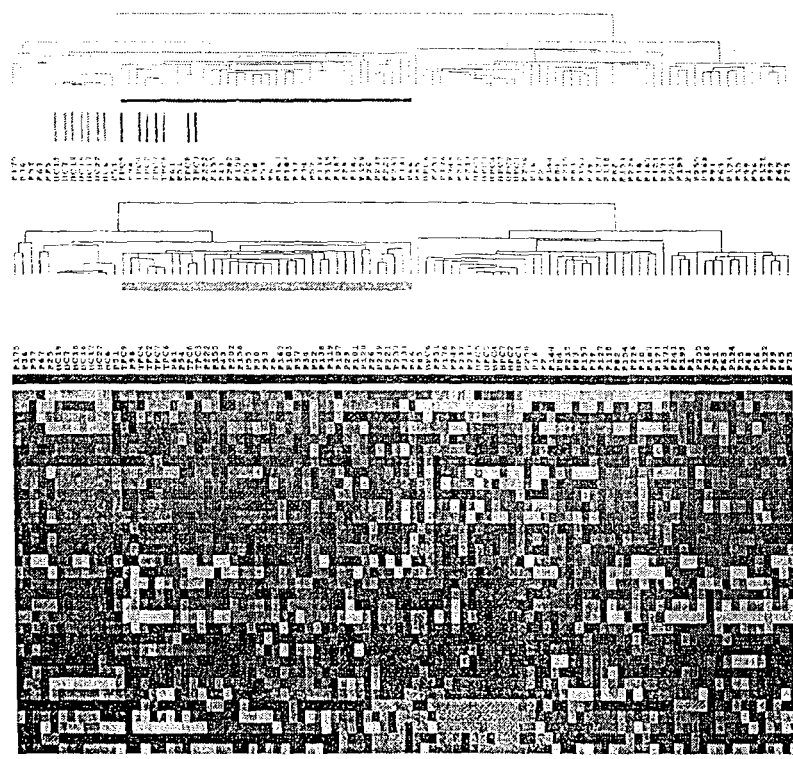

FIG. 13 shows two-dimensional hierarchical cluster analysis of experimental expression profiles and gene behavior of 50 LDG-MM1 genes. Genes are plotted along the vertical axis (right side), and experimental samples are plotted along the top horizontal axis by their similarity. The tonsil plasma cell cluster is identified by a horizontal blue bar. Tonsil B cell, tonsil plasma cell, and bone marrow plasma cell samples are indicated as in FIG. 12.

Figure 14:
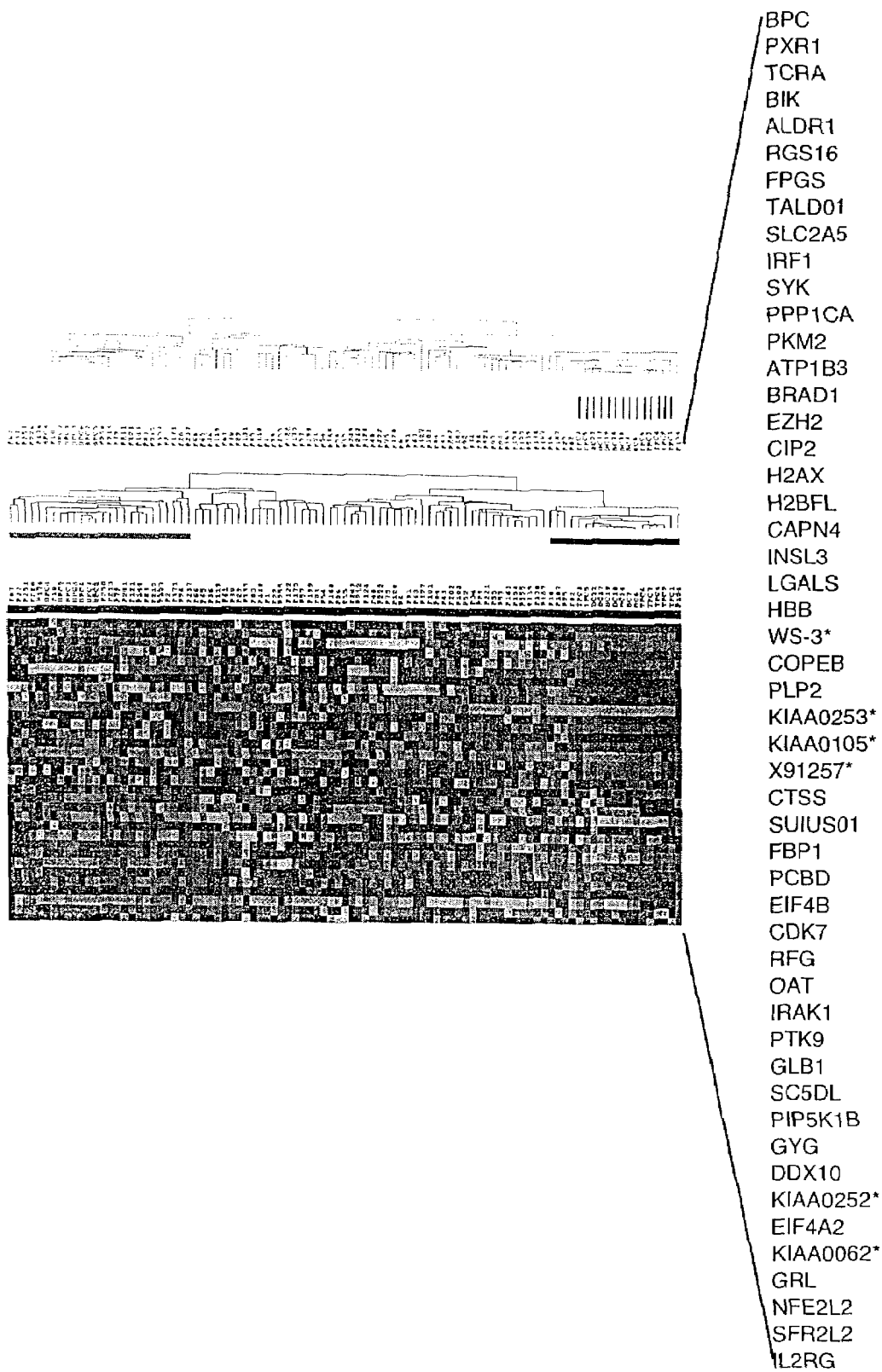

FIG. 14 shows two-dimensional hierarchical cluster analysis of experimental expression profiles and gene behavior of 50 LDG-MM2 genes. Genes are plotted along the vertical axis (right side), and experimental samples are plotted along the top horizontal axis by their similarity. The bone marrow plasma cell cluster is identified by a horizontal golden bar. Tonsil B cell, tonsil plasma cell, and bone marrow plasma cell samples are indicated as in FIG. 12.

Figure 15:
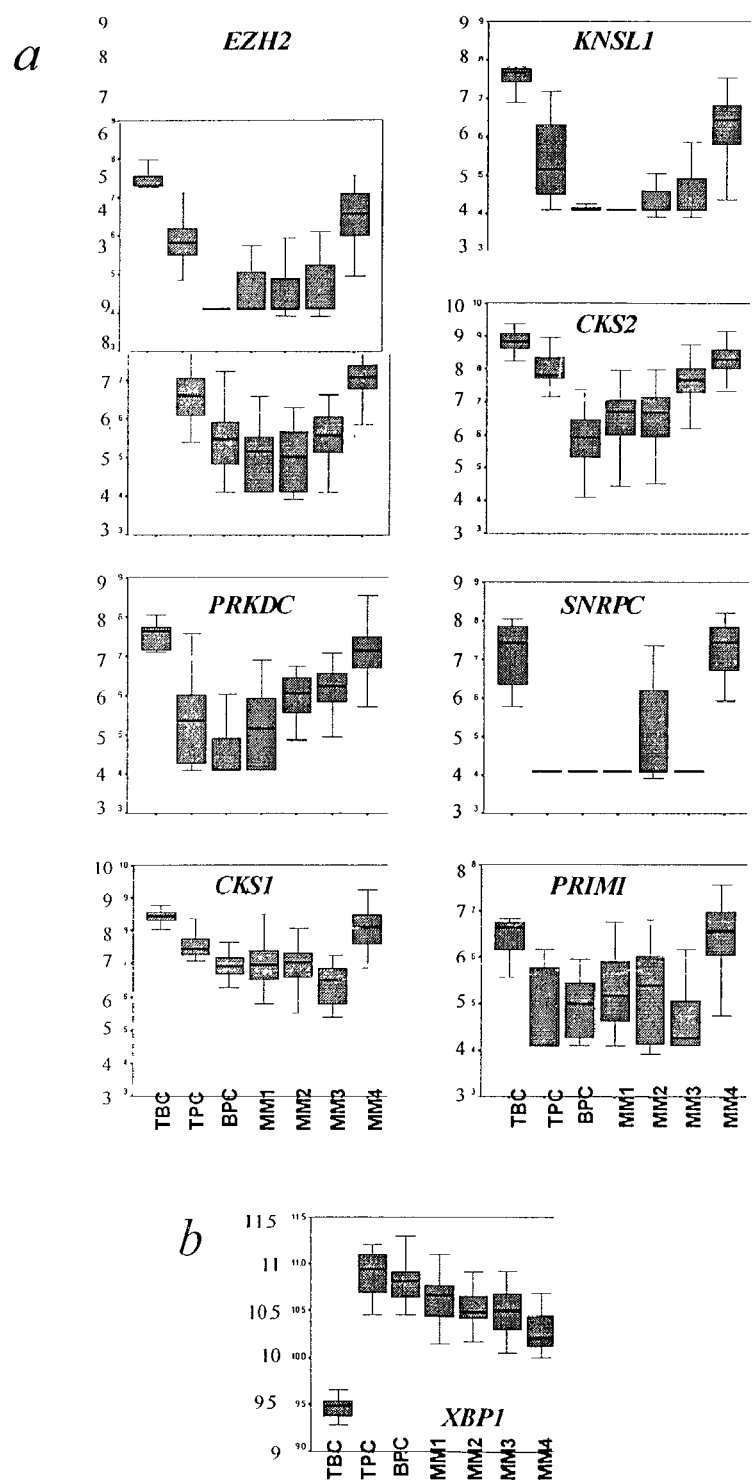

FIG. 15 shows variation in expression of proliferation genes reveals similarities between tonsil B cells and MM4. The data are shown as boxplot of Kruskal-Wallis test values. The seven groups analyzed (tonsil B cells, tonsil plasma cells, bone marrow plasma cells, and gene expression defined subgroups MM1, MM2, MM3, and MM4) are distributed along the x-axis and the natural log transformed average difference is plotted on the y axis. EZH2; $P=7.61\times10^{-11}$; KNSL1, $P=3.21\times10^{-8}$; PRKDC, $P=2.86\times10^{-11}$; SNRPC, $P=5.44\times10^{-12}$; CCNB1, $P=2.54\times10^{-8}$; CKS2, $P=9.49\times10^{-11}$; CKS1, $P=5.86\times10^{-9}$; PRIM1, $P=4.25\times10^{-5}$.

Figure 16:
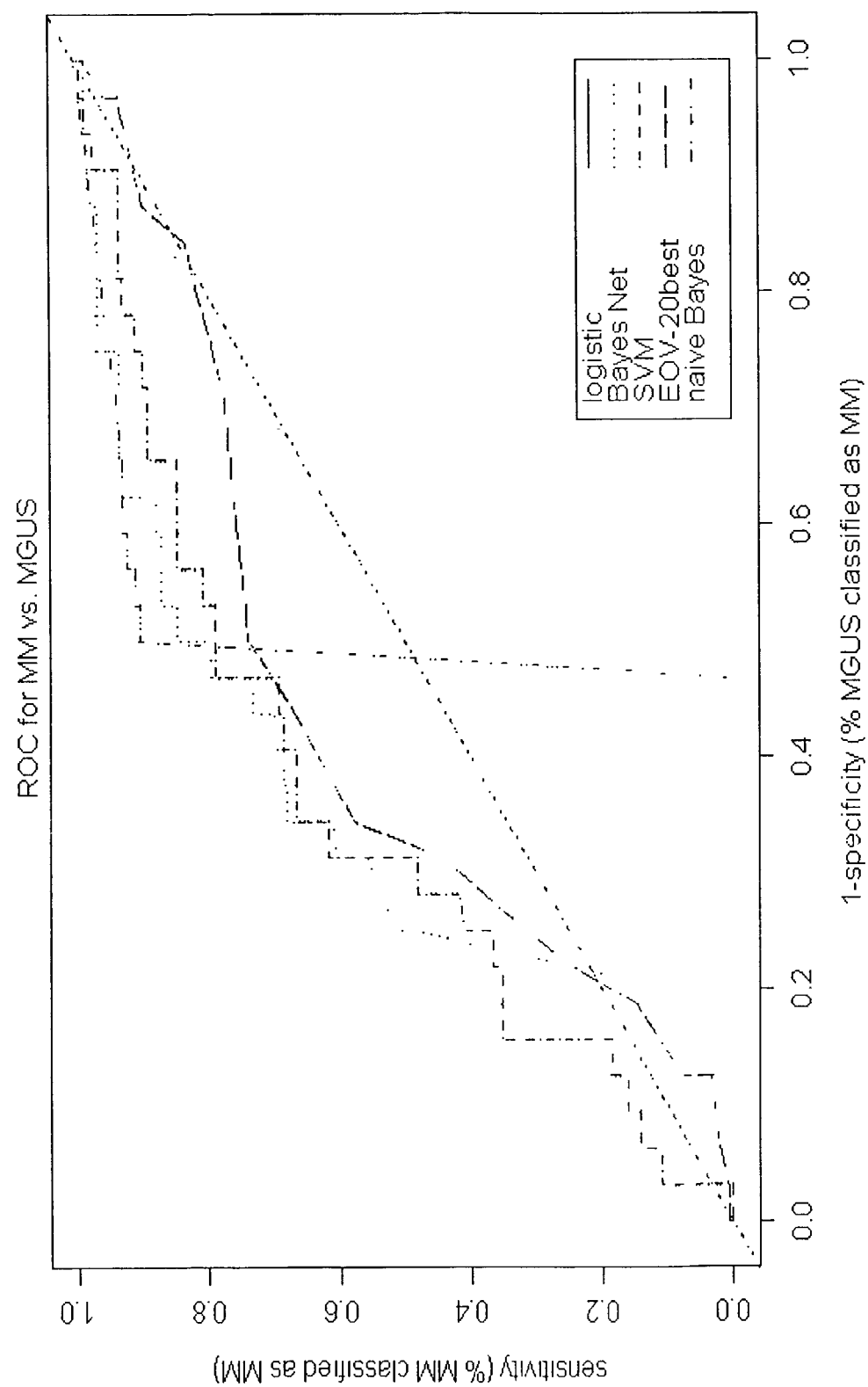

FIG. 16 shows the receiver operating characteristic (ROC) curves for the multiple myeloma (MM) vs monoclonal gammopathy of undetermined significance (MGUS) classification.

DETAILED DESCRIPTION OF THE INVENTION

There is now strong evidence that global gene expression profiling can reveal a molecular heterogeneity of similar or related hematopoietic malignancies that have been difficult to distinguish. The most significantly differentially expressed genes in a comparison of normal and malignant cells can be used in the development of clinically relevant diagnostics as well as provide clues into the basic mechanisms of cellular transformation. In fact, these profiles might even be used to identify malignant cells even in the absence of any clinical manifestations. In addition, the biochemical pathways in which the products of these genes act may be targeted by novel therapeutics.

The present invention demonstrates that both normal and malignant plasma cells can be purified to homogeneity from bone marrow aspirates using anti-CD 138-based immunomagnetic bead-positive selection. Using these cells, the present invention provides the first comprehensive global gene expression profiling of newly diagnosed multiple myeloma patients and contrasted these expression patterns with those of normal plasma cells. Novel candidate multiple myeloma disease genes were identified using the method of gene expression profiling disclosed herein and this profiling has lead to the development of a gene-based classification system for multiple myeloma.

Results from hierarchical cluster analysis on multiple myeloma and normal plasma cells, as well as the benign plasma cell dyscrasia monoclonal gammopathy of undetermined significance and the end-stage-like multiple myeloma cell lines revealed normal plasma cells are unique and that primary multiple myeloma is either like monoclonal gammopathy of undetermined significance or multiple myeloma cell lines. In addition, multiple myeloma cell line gene expression was homogeneous as evidenced by the tight clustering in the hierarchical analysis. The similarity of multiple myeloma cell line expression patterns to primary newly diagnosed forms of multiple myeloma support the validity of using multiple myeloma cell lines as models for multiple myeloma.

Upon hierarchical clustering of multiple myeloma alone, four distinct clinical multiple myeloma subgroups (MM1 to MM4) were distinguished. The MM1 subgroup contained samples that were more like monoclonal gammopathy of undetermined significance, whereas the MM4 subgroup contained samples more like multiple myeloma cell lines. The most significant gene expression patterns differentiating MM1 and MM4 were cell cycle control and DNA metabolism genes, and the MM4 subgroup was more likely to have abnormal cytogenetics, elevated serum β2M, elevated creatinine, and deletions of chromosome 13. These are important variables that historically have been linked to poor prognosis.

Gene Expression Changes in Multiple Myeloma

Data disclosed herein indicated that the MM4 subgroup likely represents the most high-risk clinical entity. Thus, knowledge of the molecular genetics of this particular subgroup, should provide insight into its biology and possibly provide a rationale for appropriate subtype-specific therapeutic interventions. The most significant gene expression changes differentiating the MM1 and MM4 subgroups code for activities that clearly implicate MM4 as having a more proliferative and autonomous phenotype. The most significantly altered gene in the comparison, TYMS (thymidylate synthase), which functions in the prymidine biosynthetic pathway, has been linked to resistance to fluoropyrimidine chemotherapy and also poor prognosis in colorectal carcinomas. Other notable genes upregulated in MM4 were the CAAX farnesyltransferase gene, FTNA. Farnesyltransferase prenylates RAS, a post translational modification required to allow RAS to attach to the plasma membrane. These data suggest that farnesyltransferase inhibitors may be effective in treating patients with high levels of FTNA expression.

Two other genes coding for components of the proteasome pathway, POH1 (26S proteasome-associated pad1 homolog) and UBL1 (ubiquitin-like protein 1) were also overexpressed in MM4. Overexpression of POH1 confers P-glycoprotein-independent, pleotropic drug resistance to mammalian cells. UBL1, also known as sentrin, is involved in many processes including associating with RAD51, RAD52, and p53 proteins in the double-strand repair pathway; conjugating with RAN-GAP1 involved in nuclear protein import; and importantly for multiple myeloma, protecting against both Fas/Apo-1 (TN-FRSF6) or TNFR1-induced apoptosis. In contrast to normal plasma cells, more than 75% of multiple myeloma plasma cells express abundant mRNA for the multidrug resistance gene, lung-resistance-related protein (MVP). These data are consistent with previous reports showing that expression of MVP in multiple myeloma is a poor prognostic factor. Given the uniform development of chemotherapy resistance in multiple myeloma, the combined overexpression of POH1 and MVP may have profound influences on this phenotype. The deregulated expression of many genes whose products function in the proteasome pathway may be used in the pharmacogenomic analysis of efficacy of proteasome inhibitors like PS-341 (Millennium Pharmaceuticals, Cambridge, Mass.).

Another significantly upregulated gene in MM4 was the single stranded DNA-dependent ATP-dependent helicase (G22P1), which is also known as Ku70 autoantigen. The DNA helicase II complex, made up of p70 and p80, binds preferentially to fork-like ends of double-stranded DNA in a cell cycle-dependent manner. Binding to DNA is thought to be mediated by p70 and dimerization with p80 forms the ATP-dependent DNA-unwinding enzyme (helicase II) and acts as the regulatory component of a DNA-dependent protein kinase (DNPK) which was also significantly upregulated in MM4. The involvement of the helicase II complex in DNA double-strand break repair, V(D)J recombination, and notably chromosomal translocations has been proposed. Another gene upregulated was the DNA fragmentation factor (DFFA). Caspase-3 cleaves the DFFA-encoded 45 kD subunit at two sites to generate an active factor that produces DNA fragmentation during apoptosis signaling. In light of the many blocks to apoptosis in multiple myeloma, DFFA activation could result in DNA fragmentation, which in turn would activate the helicase II complex that then may facilitate chromosomal translocations. It is of note that abnormal karyotypes, and thus chromosomal translocations, are associated with the MM4 subgroup which tended to overexpress these two genes.

Hence, results disclosed herein demonstrate that direct comparison of gene expression patterns in multiple myeloma and normal plasma cells can identified novel genes that could represent the fundamental changes associated with the malignant transformation of plasma cells.

The progression of multiple myeloma as a hypoproliferative tumor is thought to be linked to a defect in programmed cell death rather than rapid cell replication. Two genes, prohibitin (PHB) and quiescin Q6 (QSCN6), overexpressed in multiple myeloma are involved in growth arrest. The overexpression of these genes may b e responsible for the typically low proliferation indices seen in multiple myeloma. It is hence conceivable that therapeutic downregulation of these genes that results in enhanced proliferation could render multiple myeloma cells more susceptible to cell cycle-active chemotherapeutic agents.

The gene coding for CD27, TNFRSF7, the second most significantly underexpressed gene in multiple myeloma, is a member of the tumor necrosis factor receptor (TNFR) superfamily that provides co-stimulatory signals for T and B cell proliferation and B cell immunoglobulin production and apoptosis. Anti-CD27 significantly inhibits the induction of Blimp-1 and J-chain transcripts which are turned on in cells committed to plasma cell differentiation, suggesting that ligation of CD27 on B cells may prevent terminal differentiation. CD27 ligand (CD70) prevents IL-10-mediated apoptosis and directs differentiation of CD27$^+$ memory B cells toward plasma cells in cooperation with IL-10. Thus, it is possible that the downregulation of CD27 gene expression in multiple myeloma may block an apoptotic program.

The overexpression of CD47 on multiple myeloma may be related to escape of multiple myeloma cells from immune surveillance. Studies have shown that cells lacking CD47 are rapidly cleared from the bloodstream by splenic red pulp macrophages and CD47 on normal red blood cells prevents this elimination.

The gene product of DNA methyltransferase 1, DNMT1, overexpressed in multiple myeloma, is responsible for cytosine methylation in mammals and has an important role in epigenetic gene silencing. In fact, aberrant hypermethylation of tumor suppressor genes plays an important role in the development of many tumors. De novo methylation of p16/INK4α is a frequent finding in primary multiple myeloma. Also, recent studies have shown that upregulated expression of DNMTs may contribute to the pathogenesis of leukemia by inducing aberrant regional hypermethylation. DNA methylation represses genes partly by recruitment of the methyl-CpG-binding protein MeCP2, which in turn recruits a histone deacetylase activity. It has been shown that the process of DNA methylation, mediated b y Dnmt1, may depend on or generate an altered chromatin state via histone deacetylase activity. It is potentially significant that multiple myeloma cases also demonstrate significant overexpression of the gene for metastasis-associated 1 (MTA1). MTA1 was originally identified as being highly expressed in metastatic cells. MTA1 has more recently been discovered to be one subunit of the NURD (NUcleosome Remodeling and histone Deacetylation) complex which contains not only ATP-dependent nucleosome disruption activity, but also histone deacetylase activity. Thus, over expression of DNMT1 and MTA1 may have dramatic effects on repressing gene expression in multiple myeloma.

Oncogenes activated in multiple myeloma included ABL and MYC. Although it is not clear whether ABL tyrosine kinase activity is present in multiple myeloma, it is important to note that overexpression of abl and c-myc results in the accelerated development of mouse plasmacytomas. Thus, it may be more than a coincidence that multiple myeloma cells significantly overexpresses MYC and ABL.

Chromosomal translocations involving the MYC oncogene and IGH and IGL genes that result in dysregulated MYC expression are hallmarks of Burkitt's lymphoma and experimentally induced mouse plasmacytomas; however, MYC/IGH-associated translocations are rare in multiple myeloma. Although high MYC expression was a common feature in our panel of multiple myeloma, it was quite variable, ranging from little or no expression to highly elevated expression. It is also of note that the MAZ gene whose product is known to bind to and activate MYC expression was significantly upregulated in the MM4 subgroup. Given the important role of MYC in B cell neoplasia, it is speculated that overexpression of MYC, and possibly ABL, in multiple myeloma may have biological and possibly prognostic significance.

EXT1 and EXT2, which are tumor suppressor genes involved in hereditary multiple exostoses, heterodimerize and are critical in the synthesis and display of cell surface heparan sulfate glycosaminoglycans (GAGs). EXT1 is expressed in both multiple myeloma and normal plasma cells. EXT2L was overexpressed in multiple myeloma, suggesting that a functional glycosyltransferase could be created in multiple myeloma. It is of note that syndecan-1 (CD138/SDC1), a transmembrane heparan sulfate proteoglycan, is abundantly expressed on multiple myeloma cells and, when shed into the serum, is a negative prognostic factor. Thus, abnormal GAG-modified SDC1 may be important in multiple myeloma biology. The link of SDC1 to multiple myeloma biology is further confirmed by the recent association of SDC1 in the signaling cascade induced by the WNT proto-oncogene products. It has been showed that syndecan-1 (SDC1) is required for Wnt-1-induced mammary tumorigenesis. Data disclosed herein indicated a significant downregulation of WNT10B in primary multiple myeloma cases. It is also of note that the WNT5A gene and the FRZB gene, which codes for a decoy WNT receptor, were also marginally upregulated in newly diagnosed multiple myeloma. Given that the WNTs represent a novel class of B cell regulators, deregulation of the expression of these growth factors (WNT5A, WNT10B) and their receptors (e.g., FRZB) and genes products that modulate receptor signaling (e.g., SDC1), may be important in the genesis of multiple myeloma.

The present invention also identifies, through multivariate stepwise discriminant analysis, a minimum subset of genes whose expression is intimately associated with the malignant features of multiple myeloma. By applying linear regression analysis to the top 50 statistically significant differentially expressed genes, 14 genes were defined as predictors that are able to differentiate multiple myeloma from normal plasma cells with a high degree of accuracy. When the model was applied to a validation group consisting of 118 multiple myeloma, 6 normal plasma cells and 7 cases of MGUS, an accuracy of classification of more than 99% was achieved. Importantly, 6 of the 7 MGUS cases were classified as multiple myeloma, indicating that MGUS has gene expression features of malignancy. Thus the altered expression of 14 genes out of over 6,000 genes interrogated are capable of defining multiple myeloma. Similar multivariate discriminant analysis also identified a set of 24 genes that can distinguish between the four multiple myeloma subgroups described above.

In addition to identifying genes that were statistically different between the group of normal plasma cells and multiple myeloma plasma cells, the present invention also identified genes, like FGFR3 and CCND1, that demonstrate highly elevated "spiked" expression in subsets of multiple myelomas. Patients with elevated expression of these genes can have significant distribution differences among the four gene expression cluster subgroups. For example, FGFR3 spikes are found in MM1 and MM2 whereas spikes of IFI27 are more likely to be found in MM3 and MM4. Highly elevated expression of the interferon-induced gene IFI27 may be indicative of a viral infection, either systemic or specifically within the plasma cells from these patients. Correlation analysis has shown that IFI27 spikes are significantly linked (Pearson correlation coefficient values of 0.77 to 0.60) to elevated expression of 14 interferon-induced genes, including MX1, MX2, OAS1, OAS2, IFIT1, IFIT4, PLSCR1, and STAT1. More recent analysis of a large population of multiple myeloma patients (N=280) indicated that nearly 25% of all patients had spikes of the IFI27 gene. It is of interest to determine whether or not the IFI27 spike patients who cluster in the MM4 subgroup are more likely to have a poor clinical course and to identify the suspected viral infection causing the upregulation of this class of genes. Thus, spiked gene expression may also be used in the development of clinically relevant prognostic groups.

Finally, the 100% coincidence of spiked FGFR3 or CCND1 gene expression with the presence of the t(4;14)(p14;q32) or t(11;14)(q13;q32) translocations, as well as the strong correlations between protein expression and gene expression represent important validations of the accuracy of gene expression profiling and suggests that gene expression profiling may eventually supplant the labor intensive and expensive clinical laboratory procedures, such as cell surface marker immunophenotyping and molecular and cellular cytogenetics.

Genes identified by the present invention that shows significantly up-regulated or down-regulated expression in multiple myeloma are potential therapeutic targets for multiple myeloma. Over-expressed genes may be targets for small molecules or inhibitors that decrease their expression. Methods and materials that can be used to inhibit gene expression, e.g. small drug molecules, anti-sense oligo, or antibody would be readily apparent to a person having ordinary skill in this art. On the other hand, under-expressed genes can be replaced by gene therapy or induced by drugs.

Comparison of Multiple Myeloma with Normal Plasma Cell Development

Data disclosed herein indicated that multiple myeloma can be placed into a developmental schema parallel to that of normal plasma cell differentiation. Global gene expression profiling reveals distinct changes in transcription associated with human plasma cell differentiation. Hierarchical clustering analyses with 4866 genes segregated tonsil B cells, tonsil plasma cells, and bone marrow plasma cells. Combining $\chi^2$ and Wilcoxon rank sum tests, 359 previously defined and novel genes significantly (P<0.0005) discriminated tonsil B cells from tonsil plasma cells, and 500 genes significantly discriminated tonsil plasma cells from bone marrow plasma cells. Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). One-way ANOVA was then applied to EDGs and LDGs to identify statistically significant expression differences between multiple myeloma (MM) and tonsil B cells (EDG-MM), tonsil plasma cells (LDG-MM1), or bone marrow plasma cells (LDG-MM2).

Hierarchical cluster analysis revealed that 13/18 (P=0.00005) MM4 cases (a putative poor-prognosis subtype) clustered tightly with tonsil B cells. The other groups (MM1, 2 and 3) failed to show such associations. In contrast, there was tight clustering between tonsil plasma cells and 14/15 (P=0.00001) MM3, and significant similarities between bone marrow plasma cells and 14/20 (P=0.00009) MM2 cases were found. MM1 showed no significant linkage with the normal cell types studied. In addition, XBP1, a transcription factor essential for plasma cell differentiation, exhibited a significant, progressive reduction in expression from MM1 to MM4, consistent with developmental-stage relationships. Therefore, global gene expression patterns linked to late-stage B cell differentiation confirmed and extended a global gene expression-defined classification system of multiple myeloma, suggesting that multiple myeloma represents a constellation of distinct subtypes of disease with unique origins.

The present invention is drawn to a method of gene-based classification for multiple myeloma. Nucleic acid samples of isolated plasma cells derived from individuals with or without multiple myeloma were applied to a DNA microarray, and hierarchical clustering analysis performed on data obtained from the microarray will classify the individuals into distinct subgroups such as the MM1, MM2, MM3 and MM4 subgroups disclosed herein.

In another embodiment of the present invention, there is provided a method of identifying genes with elevated expression in subsets of multiple myeloma patients. Nucleic acid samples of isolated plasma cells derived from individuals with multiple myeloma were applied to a DNA microarray, and hierarchical clustering analysis performed on data obtained from the microarray will identify genes with elevated expression in subsets of multiple myeloma patients. Representative examples of these genes are listed in Table 8.

In another embodiment of the present invention, there is provided a method of identifying potential therapeutic targets for multiple myeloma. Nucleic acid samples of isolated plasma cells derived from individuals with or without multiple myeloma were applied to a DNA microarray, and hierarchical clustering analysis was performed on data obtained from the microarray. Genes with significantly different levels of expression in multiple myeloma patients as compared to normal individuals are potential therapeutic targets for multiple myeloma. Representative examples of these genes are listed in Tables 4, 5 and 8.

In yet another embodiment of the present invention, there is provided a method of identifying a group of genes that can distinguish between normal plasma cells and plasma cells of multiple myeloma. Nucleic acid samples of isolated plasma cells derived from individuals with or without multiple myeloma were applied to a DNA microarray, and hierarchical clustering analysis was performed on data obtained from the microarray. Genes with statistically significant differential expression patterns were identified, and linear regression analysis was used to identify a group of genes that is capable of accurate discrimination between normal plasma cells and plasma cells of multiple myeloma. Representative examples of these genes are listed in Table 6.

In still yet another embodiment of the present invention, there is provided a method of identifying a group of genes that can distinguish between subgroups of multiple myeloma. Nucleic acid samples of isolated plasma cells derived from individuals with multiple myeloma were applied to a DNA microarray, and hierarchical clustering analysis was performed on data obtained from the microarray. Genes with statistically significant differential expression patterns were identified, and linear regression analysis was used to identify a group of genes that is capable of accurate discrimination between subgroups of multiple myeloma. Representative examples of these genes are listed in Table 7.

In another embodiment of the present invention, there is provided a method of diagnosis for multiple myeloma. Expression levels of a group of 14 genes as listed in Table 6 were examined in plasma cells derived from an individual, wherein statistically significant differential expression would indicate that such individual has multiple myeloma. Gene expression levels can be examined a t nucleic acid level or protein level according to methods well known to one of skill in the art.

In yet another embodiment of the present invention, there is provided a method of diagnosis for subgroups of multiple myeloma. Expression levels of a group of 24 genes as listed in Table 7 were examined in plasma cells derived from an individual, wherein statistically significant differential expression would provide diagnosis for subgroups of multiple myeloma. Gene expression levels can b e examined at nucleic acid level or protein level according to methods well known to one of skill in the art.

In another embodiment of the present invention, there are provided methods of treatment for multiple myeloma. Such methods involve inhibiting expression of one of the genes listed in Table 5 or Table 8, or increasing expression of one of the genes listed in Table 4. Methods of inhibiting or increasing gene expression such as those using anti-sense oligonucleotide or antibody are well known to one of skill in the art.

The present invention is also drawn to a method of developmental stage-based classification for multiple myeloma. Nucleic acid samples of isolated B cells and plasma cells derived from individuals with or without multiple myeloma were applied to a DNA microarray, and hierarchical clustering analysis performed on data obtained from the microarray will classify the multiple myeloma cells according to the developmental stages of normal B cells and plasma cells. In general, normal B cells and plasma cells are isolated from tonsil, bone marrow, mucoal tissue, lymph node or peripheral blood.

The following examples are given for the purpose of illustrating various embodiments of the invention and are not meant to limit the present invention in any fashion.

EXAMPLE 1

Cell Isolation and Analysis

Samples for the following studies included plasma cells from 74 newly diagnosed cases of multiple myeloma, 5 subjects with monoclonal gammopathy of undetermined significance, 7 samples of tonsil B lymphocytes (tonsil BCs), 11 samples of tonsil plasma cells (tonsil PCs), and 31 bone marrow PCs derived from normal healthy donor. Multiple myeloma cell lines (U266, ARP1, RPMI-8226, UUN, ANBL-6, CAG, and H929 (courtesy of P. L. Bergsagel) and a n Epstein-Barr virus (EBV)-transformed B-lymphoblastoid cell line (ARH-77) were grown as recommended (ATCC, Chantilly, Va.).

Tonsils were obtained from patients undergoing tonsillectomy for chronic tonsillitis. Tonsil tissues were minced, softly teased and filtered. The mononuclear cell fraction from tonsil preparations and bone marrow aspirates were separated by a standard Ficoll-Hypaque gradient (Pharmacia Biotech, Piscataway, N.J.). The cells in the light density fraction (S.G.≦1.077) were resuspended in cell culture media and 10% fetal bovine serum, RBC lysed, and several PBS wash steps were performed. Plasma cell isolation was performed with anti-CD138 immunomagnetic bead selection as previously described (Zhan et al., 2002). B lymphocyte isolation was performed using directly conjugated monoclonal mouse anti-human CD19 antibodies and the AutoMacs automated cell sorter (Miltenyi-Biotec, Auburn, Calif.).

For cytology, approximately 40,000 purified tonsil BC and PC mononuclear cells were cytocentrifuged at 1000×g for 5 min at room temperature. For morphological studies, the cells were immediately processed by fixing and staining with Diff-Quick fixative and stain (Dade Diagnostics, Aguada, PR).

For immunofluorescence, slides were treated essentially as described (Shaughnessy et al., 2000). Briefly, slides were air-dried overnight, then fixed in 100% ethanol for 5 min at room temperature and baked in a dry 37° C. incubator for 6 hr. The slides were then stained with 100 µl of a 1:20 dilution of goat anti-human-kappa immunoglobulin light chain conjugated with 7-amino-4-methylcourmarin-3-acitic acid (AMCA) (Vector Laboratories, Burlingame, Calif.) for 30 min in a humidified chamber. After incubation, the slides were washed two times in 1×PBS+0.1% NP–40 (PBD). To enhance the AMCA signal, the slides were incubated with 100 µl of a 1:40 dilution of AMCA-labeled rabbit-anti-goat IgG antibody and incubated for 30 min at room temperature in a humidified chamber. Slides were washed 2 times in 1×PBD. The slides were then stained with 100 µl of a 1:100 dilution of goat anti-human-lambda immunoglobulin light chain conjugated with FITC (Vector Laboratories, Burlingame, Calif.) for 30 min in a humidified chamber; the slides were washed two times in 1×PBD. Then the slides were stained with propidium iodide at 0.1 µg/ml in 1×PBS for 5 min, washed in 1×PBD, and 10 µl anti-fade (Molecular Probes, Eugene, Oreg.) was added and coverslips were placed. Cytoplasmic immunoglobulin light chain-positive PCs were visualized using an Olympus BX60 epi-fluorescence microscope equipped with appropriate filters. The images were captured using a Quips XL genetic workstation (Vysis, Downers Grove, Ill.).

Both unpurified mononuclear cells and purified fractions from tonsil BCs, tonsil PCs, and bone marrow PCs were subjected to flow cytometric analysis of CD marker expression using a panel of antibodies directly conjugated to FITC or PE. Markers used in the analysis included FITC-labeled CD20, PE-labeled CD38, FITC-labeled or ECD-labeled CD45, PE- or PC5-labled CD138 (Beckman Coulter, Miami, Fla.). For detection of CD138 on PCs after CD138 selection, we employed an indirect detection strategy using a FITC-labeled rabbit anti-mouse IgG antibody (Beckman Coulter) to detect the mouse monoclonal anti-CD 138 antibody BB4 used in the immunomagnetic selection technique. Cells were taken after Ficoll Hypaque gradient or after cell purification, washed in PBS, and stained at 4° C. with CD antibodies or isotype-matched control G1 antibodies (Beckman Coulter).

After staining, cells were resuspended in 1×PBS and analyzed using a Epics XL-MCL flow cytometry system (Beckman Coulter).

EXAMPLE 2

Preparation of Labeled cRNA And Hybridization to High-Density Microarray

Total RNA was isolated with RNEASY (RNeasy) Mini Kit (Qiagen, Valencia, Calif.). Double-stranded cDNA and biotinylated cRNA were synthesized from total RNA and hybridized to HUGENEFL (HuGeneFL) GENECHIP (GeneChip) microarrays (Affymetrix, Santa Clara, Calif.), which were washed and scanned according to procedures developed by the manufacturer. The arrays were scanned using Hewlett Packard confocal laser scanner and visualized using Affymetrix 3.3 software (Affymetrix). Arrays were scaled to an average intensity of 1,500 and analyzed independently.

EXAMPLE 3

GENECHIP (Genechip) Data Analysis

To efficiently manage and mine high-density oligonucleotide DNA microarray data, a new data-handling tool was developed. GENECHIP (GeneChip)-derived expression data was stored on an MS SQL Server. This database was linked, via an MS Access interface called Clinical Gene-Organizer to multiple clinical parameter databases for multiple myeloma patients. This Data Mart concept allows gene expression profiles to be directly correlated with clinical parameters and clinical outcomes using standard statistical software. All data used in the present analysis were derived from Affymetrix 3.3 software. GENECHIP (GeneChip) 3.3 output files are given (1) as an average difference (AD) that represents the difference between the intensities of the sequence-specific perfect match probe set and the mismatch probe set, or (2) as an absolute call (AC) of present or absent as determined by the GENECHIP (GeneChip) 3.3 algorithm. Average difference calls were transformed by the natural log after substituting any sample with an average difference of <60 with the value 60 (2.5 times the average Raw Q). Statistical analysis of the data was performed with software packages SPSS 10.0 (SPSS, Chicago, Ill.), S-Plus 2000 (Insightful Corp., Seattle, Wash.), and Gene Cluster/Treeview (Eisen et al., 1998).

To differentiate four distinct subgroups of multiple myeloma (MM1, MM2, MM3 and MM4), hierarchical clustering of average linkage clustering with the centered correlation metric was employed. The clustering was done on the average difference data of 5,483 genes. Either Chi square ($\chi^2$) or Fisher's exact test was used to find significant differences between cluster groups with the AC data. To compare the expression levels, the non-parametric Wilcoxon rank sum (WRS) test was used. This test uses a null hypothesis that is based on ranks rather than on normally distributed data. Before the above tests were performed, genes that were absent (AC) across all samples were removed; 5,483 genes were used in the analyses. Genes that were significant (P<0.0001) for both the $\chi^2$ test and the WRS test were considered to be significantly differentially expressed.

Clinical parameters were tested across multiple myeloma cluster groups. ANOVA test was used to test the continuous variables, and $\chi^2$ test of independence or Fisher's exact test was applied to test discrete variables. The natural log of the average difference data was used to find genes with a "spiked profile" of expression in multiple myeloma. Genes were identified that had low to undetectable expression in the majority of patients and normal samples (no more than 4 present absolute calls [P-AC]). A total of 2,030 genes fit the criteria of this analysis. The median expression value of each of the genes across all patient samples was determined. For the $i^{th}$ gene, this value was called medgene (i). The $i^{th}$ gene was a "spiked" gene if it had at least 4 patient expression values >2.5+ medgene (i). The constant 2.5 was based on the log of the average difference data. These genes that were "spiked" were further divided into subsets according to whether or not the largest spike had an average difference expression value greater than 10,000.

To determine transcriptional changes associated with human plasma cell differentiation, a total of 4866 genes were scanned across 7 cases each of tonsil B cells, tonsil plasma cells, and bone marrow plasma cells. The 4866 genes were derived from 6800 by filtering out all control genes, and genes not fulfilling the test of Max-Min<1.5 (1.5 being the natural log of the average difference). The $\chi^2$ test was used to eliminate genes with absent absolute call (AAC). For example, in the tonsil plasma cell to bone marrow plasma cell comparison, genes with $\chi^2$ values greater than 3.84 (P<0.05) or having "present" AC (PAC) in more than half of the samples in each group were retained. In the tonsil B cell to tonsil plasma cell and tonsil plasma cell to bone marrow plasma cell comparisons, 2662 and 2549 genes were retained as discriminating between the two groups, respectively. To compare gene expression levels, the non-parametric Wilcoxon Rank Sum (WRS) test was used to compare two groups using natural log transformed AD. The cutoff P value depended on the sample size, the heterogeneity of the two comparative populations (tonsil B cells, tonsil plasma cells, and bone marrow plasma cells showed a higher degree of stability in AD), and the degree of significance. In this analysis, 496 and 646 genes were found to be significantly (P<0.0005) differentially expressed in the tonsil B cell versus tonsil plasma cell and tonsil plasma cell versus bone marrow plasma cell comparisons, respectively. To define the direction of significance (expression changes being up or down in one group compared with the other), the non-parametric Spearman correlation test of the AD was employed.

Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). Previously defined and novel genes were identified that significantly discriminated tonsil B cells from tonsil plasma cells (359 genes) and tonsil plasma cells from bone marrow plasma cells (500 genes).

To classify multiple myeloma with respect to EDG and LDG, 74 newly diagnosed cases of multiple myeloma and 7 tonsil B cell, 7 tonsil plasma cell, and 7 bone marrow plasma cell samples were tested for variance across the 359 EDGs and 500 LDGs. The top 50 EDGs that showed the most significant variance across all samples were defined as early differentiation genes for myeloma (EDG-MM). Likewise, the top 50 LDGs showing the most significant variance across all samples were identified as late differentiation genes for myeloma-1 (LDG-MM1). Subtracting the LDG-MM1 from the 500 LDG and then applying one-way ANOVA test for variance to the remaining genes identified the top 50 genes showing similarities between bone marrow plasma cells and multiple myeloma. These genes were defined as LDG-MM2.

Hierarchical clustering was applied to all samples using 30 of the 50 EDG-MM. A total of 20 genes were filtered out with Max-Min <2.5. This filtering was performed on this group because many of the top 50 EDG-MM showed no variability across multiple myeloma and thus could not be used to distinguish multiple myeloma subgroups. A similar clustering strategy was employed to cluster the samples using the 50 LDG-MM1 and 50 LDG-MM2; however, in these cases all 50 significant genes were used in the cluster analysis.

EXAMPLE 4

RT-PCR and Immunohistochemistry

RT-PCR for the FGFR3 MMSET was performed on the same cDNAs used in the microarray analysis. Briefly, cDNA was mixed with the IGJH2 (5'-CAATGGTCACCGTCTCT-TCA-3', SEQ ID No. 1) primer and the MMSET primer (5'-CCTCAATTTCCTGAAATTGGTT-3', SEQ ID No. 2). PCR reactions consisted of 30 cycles with a 58° C. annealing temperature and 1-minute extension time at 72° C. using a Perkin-Elmer GeneAmp 2400 thermocycler (Wellesley, Mass.). PCR products were visualized by ethidium bromide staining after agarose gel electrophoresis.

Immunohistochemical staining was performed on a Ventana ES (Ventana Medical Systems, Tucson, Ariz.) using Zenker-fixed paraffin-embedded bone marrow sections, an avidin-biotin peroxidase complex technique (Ventana Medical Systems), and the antibody L26 (CD20, Ventana Medical Systems). Heat-induced epitope retrieval was performed by microwaving the sections for 28 minutes in a 1.0-mmol/L concentration of citrate buffer at pH 6.0.

EXAMPLE 5

Interphase FISH

For interphase detection of the t(11;14)(q13;q32) translocation fusion signal, a LSI IGH/CCND1 dual-color, dual-fusion translocation probe was used (Vysis, Inc, Downers Grove, Ill.). The TRI-FISH procedure used to analyze the samples has been previously described. Briefly, at least 100 clonotypic plasma cells identified by cIg staining were counted for the presence or absence of the translocation fusion signal in all samples except one, which yielded only 35 plasma cells. An multiple myeloma sample was defined as having the translocation when >25% of the cells contained the fusion.

EXAMPLE 6

Figure 1A:
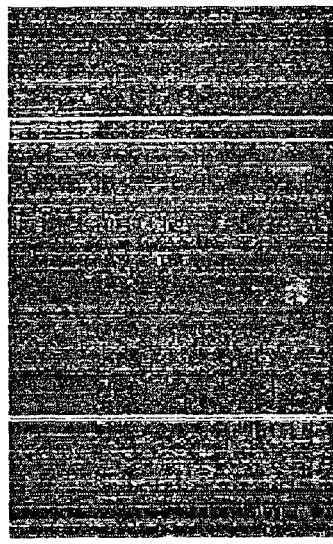
FIG. 1A shows cluster-ordered data table. The clustering is presented graphically as a colored image. Along the vertical axis, the analyzed genes are arranged as ordered by the clustering algorithm. The genes with the most similar patterns of expression are placed adjacent to each other. Likewise, along the horizontal axis, experimental samples are arranged; those with the most similar patterns of expression across all genes are placed adjacent to each other. Both sample and gene groupings can be further described by following the solid lines (branches) that connect the individual components with the larger groups. The color of each cell in the tabular image represents the expression level of each gene, with red representing an expression greater than the mean, green representing an expression less than the mean, and the deeper color intensity representing a greater magnitude of deviation from the mean.
Figure 1B:
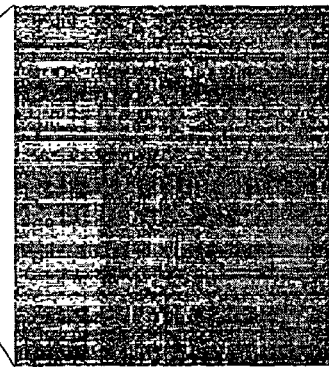
FIG. 1B shows amplified gene cluster showing genes downregulated in MM. Most of the characterized and sequence-verified cDNA-encoded genes are known to be immunoglobulins.
Figure 1C:
FIG. 1C shows cluster enriched with genes whose expression level was correlated with tumorigenesis, cell cycle, and proliferation rate. Many of these genes were also statistically significantly upregulated in multiple myeloma ($\chi^2$ and WRS test) (see Table 5).
Figure 1D:
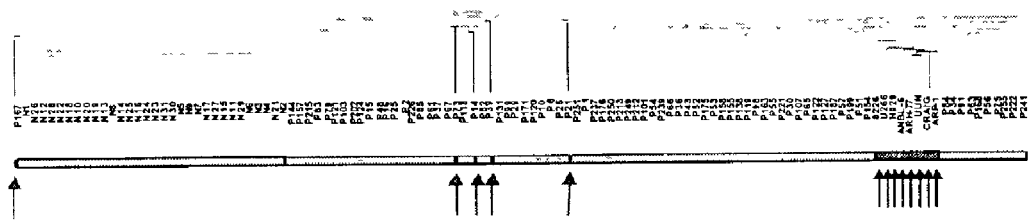
FIG. 1D shows dendrogram of hierarchical cluster. 74 cases of newly diagnosed untreated multiple myeloma, 5 monoclonal gammopathy of undetermined significance, 8 multiple myeloma cell lines, and 31 normal bone marrow plasma cell samples clustered based on the correlation of 5,483 genes (probe sets). Different-colored branches represent normal plasma cell (green), monoclonal gammopathy of undetermined significance (blue arrow), multiple myeloma (tan) and multiple myeloma cell lines (brown arrow).

Hierarchical Clustering of Plasma Cell Gene Expression Demonstrates Class Distinction As a result of 656,000 measurements of gene expression in 118 plasma cell samples, altered gene expression in the multiple myeloma samples was identified. Two-dimensional hierarchical clustering differentiated cell types by gene expression when performed on 5,483 genes that were expressed in at least one of the 118 samples (FIG. 1A). The sample dendrogram derived two major branches (FIGS. 1A and 1D). One branch contained all 31 normal samples and a single monoclonal gammopathy of undetermined significance case whereas the second branch contained all 74 multiple myeloma and 4 monoclonal gammopathy of undetermined significance cases and the 8 cell lines. The multiple myeloma-containing branch was further divided into two sub-branches, one containing the 4 monoclonal gammopathy of undetermined significance and the other the 0.8 multiple myeloma cell lines. The cell lines were all clustered next to one another, thus showing a high degree of similarity in gene expression among the cell lines. This suggested that multiple myeloma could be differentiated from normal plasma cells and that at least two different classes of multiple myeloma could be identified, one more similar to monoclonal gammopathy of undetermined significance and the other similar to multiple myeloma cell lines.

Hierarchical clustering analysis with all 118 samples together with duplicate samples from 12 patients (plasma cells taken 24 hr or 48 hr after initial sample) were repeated to show reproducibility of the technique and analysis. All samples from the 12 patients studied longitudinally were found to cluster adjacent to one another. This indicated that gene expression in samples from the same patient were more similar to each other than they were to all other samples (data not shown).

In addition to the demonstration of reproducibility of clustering noted above, three microarray analyses were also performed on a single source of RNA from one patient. When included in the cluster analysis, the three samples clustered adjacent to one another. Consistent with the manufacturer's specification, an analysis of the fold changes seen in the samples showed that <2% of all genes had a >2-fold difference. Hence, these data indicated reproducibility for same samples.

The clustergram (FIG. 1A) showed that genes of unrelated sequence but similar function clustered tightly together along the vertical axis. For example, a particular cluster of 22 genes, primarily those encoding immunoglobulin molecules and major histocompatibility genes, had relatively low expression in multiple myeloma plasma cells and high expression in normal plasma cells (FIG. 1B). This was anticipated, given that the plasma cells isolated from multiple myeloma are clonal and hence only express single immunoglobulin light-chain and heavy-chain variable and constant region genes, whereas plasma cells from normal donors are polyclonal and express many different genes of these two classes. Another cluster of 195 genes was highly enriched for numerous oncogenes/growth-related genes (e.g., MYC, ABL1, PHB, and EXT2), cell cycle-related genes (e.g., CDC37, CDK4, and CKS2), and translation machinery genes (EIF2, EIF3, HTF4A, and TFIIA) (FIG. 1C). These genes were all highly expressed in MM, especially in multiple myeloma cell lines, but had low expression levels in normal plasma cells.

EXAMPLE 7

Figure 1E:
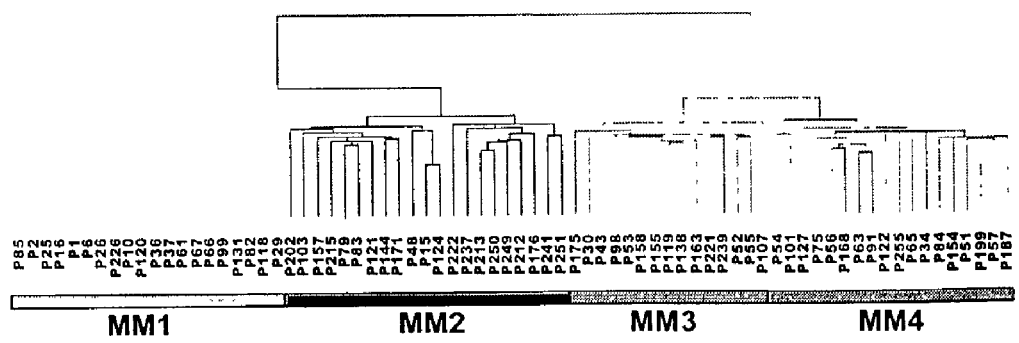
FIG. 1E shows dendrogram of a hierarchical cluster analysis of 74 cases of newly diagnosed untreated multiple myeloma alone (clustergram note shown). Two major branches contained two distinct cluster groups. The subgroups under the right branch, designated MM1 (light blue) and MM2 (blue) were more related to the monoclonal gammopathy of undetermined significance cases in FIG. 1D. The two subgroups under the left branch, designated MM3 (violet) and MM4 (red) represent samples that were more related to the multiple myeloma cell lines in FIG. 1D.

Hierarchical Clustering of Newly Diagnosed Multiple Myeloma Identifies Four Distinct Subgroups Two-dimensional cluster analysis was performed on the 74 multiple myeloma cases alone. The sample dendrogram identified two major branches with two distinct subgroups within each branch (FIG. 1E). The four subgroups were designated MM1, MM2, MM3, and MM4 containing 20, 21, 15, and 18 patients respectively. The MM1 subgroup represented the patients whose plasma cells were most closely related to the monoclonal gammopathy of undetermined significance plasma cells and MM4 were most like the multiple myeloma cell lines (see FIG. 1D). These data suggested that the four gene expression subgroups were authentic and might represent four distinct clinical entities.

Differences in gene expression across the four subgroups were then examined using the $\chi^2$ and WRS tests (Table 1). As expected the largest difference was between MM1 and MM4 (205 genes) and the smallest difference was between MM1 and MM2 (24 genes). Next, the top 30 genes turned on or upregulated in MM4 as compared with MM1 were examined (Table 2). The data demonstrated that 13 of 30 most significant genes (10 of the top 15 genes) were involved in DNA replication/repair or cell cycle control. Thymidylate synthase (TYMS), which was present in all 18 samples comprising the MM4 subgroup, was only present in 3 of the 20 MM1 samples and represented the most significant gene in the $\chi^2$ test. The DNA mismatch repair gene, mutS (*E. coli*) homolog 2 (MSH2) with a WRS P value of $2.8 \times 10^{-6}$ was the most significant gene in the WRS test. Other notable genes in the list included the CAAX farnesyltransferase (FNTA), the transcription factors enhancer of zeste homolog 2 (EZH2) and MYC-associated zinc finger protein (MAZ), eukaryotic translation initiation factors (EIF2S1 and EIF2B1), as well as the mitochondrial translation initiation factor 2 (MTIF2), the

TABLE 1

Differences In Gene Expression Among Multiple Myeloma Subgroups

| Comparison | Range of WRS* P Values | Number of Genes |
|---|---|---|
| MM1 vs MM4 | .00097 to $9.58 \times 10^{-7}$ | 205 |
| MM2 vs MM4 | .00095 to $1.0410^{-6}$ | 162 |
| MM3 vs MM4 | .00098 to $3.7510^{-6}$ | 119 |
| MM1 vs MM3 | .00091 to $6.2710^{-6}$ | 68 |
| MM2 vs MM3 | .00097 to $1.9810^{-5}$ | 44 |
| MM1 vs MM2 | .00083 to $2.9310^{-5}$ | 24 |

*Wilcoxon rank sum test. Comparisons are ordered based on the number of significant genes. Comparisons have a WRS P value < 0.001.

TABLE 2

The 30 Most Differentially Expressed Genes In A Comparison Of MM1 And MM4 Subgroups

| Accession* | Function | Gene Symbol | MM1 (N = 20) P | MM4 (N = 18) P | Chi Square | WRS‡ P Value |
|---|---|---|---|---|---|---|
| D00596 | DNA replication | TYMS | 3 | 18 | 24.35 | $1.26 \times 10^{-4}$ |
| U35835 | DNA repair | PRKDC | 2 | 17 | 23.75 | $4.55 \times 10^{-6}$ |
| U77949 | DNA replication | CDC6 | 1 | 13 | 15.62 | $5.14 \times 10^{-6}$ |
| U91985 | DNA fragmentation | DFFA | 1 | 12 | 13.38 | $6.26 \times 10^{-5}$ |
| U61145 | transcription | EZH2 | 4 | 15 | 12.77 | $1.67 \times 10^{-4}$ |
| U20979 | DNA replication | CHAF1A | 2 | 12 | 10.75 | $1.10 \times 10^{-4}$ |
| U03911 | DNA repair | MSH2 | 0 | 9 | 10.48 | $2.88 \times 10^{-6}$ |
| X74330 | DNA replication | PRIM1 | 0 | 9 | 10.48 | $9.36 \times 10^{-6}$ |
| X12517 | SnRNP | SNRPC | 0 | 9 | 10.48 | $5.26 \times 10^{-6}$ |
| D85131 | transcription | MAZ | 0 | 9 | 10.48 | $1.08 \times 10^{-5}$ |
| L00634 | farnesyltransferase | FNTA | 10 | 18 | 9.77 | $7.28 \times 10^{-5}$ |
| U21090 | DNA replication | POLD2 | 11 | 18 | 8.27 | $8.05 \times 10^{-5}$ |
| X54941 | cell cycle | CKS1 | 10 | 17 | 7.07 | $1.26 \times 10^{-4}$ |
| U62136 | cell cycle | UBE2V2 | 13 | 18 | 5.57 | $4.96 \times 10^{-6}$ |
| D38076 | cell cycle | RANBP1 | 13 | 18 | 5.57 | $7.34 \times 10^{-6}$ |
| X95592 | unknown | C1D† | 13 | 18 | 5.57 | $1.10 \times 10^{-4}$ |
| X66899 | cell cycle | EWSR1 | 14 | 18 | 4.35 | $1.89 \times 10^{-4}$ |
| L34600 | translation initiation | MTIF2 | 14 | 18 | 4.35 | $3.09 \times 10^{-5}$ |
| U27460 | Metabolism | IUGP2 | 15 | 18 | 3.22 | $1.65 \times 10^{-4}$ |
| U15009 | SnRNP | SNRPD3 | 15 | 18 | 3.22 | $1.47 \times 10^{-5}$ |
| J02645 | translation initiation | EIF2S1 | 16 | 18 | 2.18 | $7.29 \times 10^{-5}$ |
| X95648 | translation initiation | EIF2B1 | 16 | 18 | 2.18 | $1.45 \times 10^{-4}$ |
| M34539 | calcium signaling | FKBP1A | 18 | 18 | 0.42 | $1.71 \times 10^{-5}$ |
| J04611 | DNA repair | G22P1 | 18 | 18 | 0.42 | $7.29 \times 10^{-5}$ |
| U67122 | anti-apoptosis | UBL1 | 20 | 18 | 0.00 | $7.29 \times 10^{-5}$ |
| U38846 | chaperon | CCT4 | 20 | 18 | 0.00 | $1.26 \times 10^{-4}$ |
| U80040 | metabolism | ACO2 | 20 | 18 | 0.00 | $8.38 \times 10^{-5}$ |
| U86782 | proteasome | POH † | 20 | 18 | 0.00 | $5.90 \times 10^{-5}$ |
| X57152 | signaling | CSNK2B | 20 | 18 | 0.00 | $7.29 \times 10^{-5}$ |
| D87446 | unknown | KIAA0257 † | 20 | 18 | 0.00 | $1.26 \times 10^{-5}$ |

*Accession numbers listed are GENBANK ® numbers.
†Gene symbol not HUGO approved.
‡Wilcoxon rank sum test.

chaperone (CCT4), the UDP-glucose pyrophosphorylase 2 (IUGP2), and the 26S proteasome-associated pad1 homolog (POH1).

To assess the validity of the clusters with respect to clinical features, correlations of various clinical parameters across the 4 subgroups were analyzed (Table 3). Of 17 clinical variables tested, the presence of an abnormal karyotype (P=0.0003) and serum β2M levels (P=0.0005) were significantly different among the four subgroups and increased creatinine (P=0.06) and cytogenetic deletion of chromosome 13 (P=0.09) were marginally significant. The trend was to have higher β2M and creatinine as well as an abnormal karyotype and chromosome 13 deletion in the MM4 subgroup as compared with the other 3 subgroups.

TABLE 3

Clinical Parameters Linked To Multiple Myeloma Subgroups

| Clinical Parameter | Multiple Myeloma Subgroups | | | | |
|---|---|---|---|---|---|
| | 1 | 2 | 3 | 4 | P value |
| Abnormal cytogenetics | 40.0% | 5.3% | 53.3% | 72.2% | .00028 |
| Average 2-microglobulin (mg/L) | 2.81 | 2.73 | 4.62 | 8.81 | .00047 |

ANOVA, Chi square, and Fisher's exact tests were used to determine significance.

EXAMPLE 8

Altered Expression of 120 Genes in Malignant Plasma Cells

Hierarchical cluster analysis disclosed above showed that multiple myeloma plasma cells could be differentiated from normal plasma cells. Genes distinguishing the multiple myeloma from normal plasma cells were identified as significant by $\chi^2$ analysis and the WRS test (P<0.0001). A statistical analysis showed that 120 genes distinguished multiple myeloma from normal plasma cells. Pearson correlation analyses of the 120 differentially expressed genes were used to identify whether the genes were upregulated or downregulated in MM.

When genes associated with immune function (e.g. IGH, IGL, HLA) that represent the majority of significantly downregulated genes were filtered out, 50 genes showed significant downregulation in multiple myeloma (Table 4). The P values for the WRS test ranged from $9.80 \times 10^{-5}$ to $1.56 \times 10^{-14}$, and the $\chi^2$ test of the absence or presence of the expression of the gene in the groups ranged from 18.83 to 48.45. The gene representing the most significant difference in the $\chi^2$ test was the CXC chemokine SDF1. It is important to note that a comparison of multiple myeloma plasma cells to tonsil-derived plasma cells showed that, like multiple myeloma plasma cells, tonsil plasma cells also do not express SDF1. Two additional CXC chemokines, PF4 and PF4V1, were also absent in multiple myeloma plasma cells. The second most significant gene was the tumor necrosis factor receptor super family member TNFRF7 coding for CD27, a molecule that has been linked to controlling maturation and apoptosis of plasma cells.

The largest group of genes, 20 of 50, were linked to signaling cascades, multiple myeloma plasma cells have reduced or no expression of genes associated with calcium signaling (S100A9 and S100A12) or lipoprotein signaling (LIPA, LCN2, PLA2G7, APOE, APOC1). LCN2, also known as 24p3, codes for secreted lipocalin, which has recently been shown to induce apoptosis in pro B-cells after growth factor deprivation. Another major class absent in multiple, myeloma plasma cells was adhesion-associated genes (ITGA2B, IGTB2, GP5, VCAM, and MIC2).

Correlation analysis showed that 70 genes were either turned on or upregulated in multiple myeloma (Table 5). When considering the $\chi^2$ test of whether expression is present or absent, the cyclin-dependent inhibitor, CDKN1A, was the most significantly differentially expressed gene ($\chi^2=53.33$, WRS=$3.65 \times 10^{-11}$). When considering a quantitative change using the WRS test, the tyrosine kinase oncogene ABL1 was the most significant ($\chi^2=43.10$, WRS=$3.96 \times 10^{-14}$). Other oncogenes in the list included USF2, USP4, MLLT3 and MYC. The largest class of genes represented those whose products are involved in protein metabolism (12 genes), including amino acid synthesis, translation initiation, protein folding, glycosylation, trafficking, and protein degradation. Other multiple-member classes included transcription (11 genes), signaling (9 genes), DNA synthesis and modification (6 genes), and histone synthesis and modification (5 genes).

Overexpression of signaling genes such as QSCN6, PHB, phosphatases PTPRK and PPP2R4, and the kinase MAP-KAPK3 has been linked to growth arrest. The only secreted growth factor in the signaling class was HGF, a factor known to play a role in multiple myeloma biology. The MOX2 gene, whose product is normally expressed as an integral membrane protein on activated T cells and CD19$^+$ B cells and involved in inhibiting macrophage activation, was in the signaling class. The tumor suppressor gene and negative regulator of β-catenin signaling, APC, was another member of the signaling class. Classes containing two members included RNA binding, mitochondrial respiration, cytoskeletal matrix, metabolism, cell cycle, and adhesion. Single member classes included complement casasde (MASP1), drug resistance (MVP), glycosaminoglycan catabolism, heparin sulfate synthesis (EXTL2), and vesicular transport (TSC1). Four genes of unknown function were also identified as significantly upregulated in MM.

TABLE 4

The 50 Most Significantly Downregulated Genes In Multiple Myeloma In Comparison With Normal Bone Marrow Plasma Cells

| Accession* | Function | Gene Symbol | Chi Square | WRS ‡ P Value |
|---|---|---|---|---|
| L36033 | cxc chemokine | SDF1 | 48.45 | $3.05 \times 10^{-12}$ |
| M63928 | signaling | TNFRSF7 | 48.45 | $6.35 \times 10^{-11}$ |
| U64998 | ribonuclease | RNASE6 | 46.44 | $2.82 \times 10^{-9}$ |
| M20902 | lipoprotein signaling | APOC1 | 45.62 | $4.63 \times 10^{-10}$ |
| M26602 | immunity | DEFA1 | 40.75 | $1.06 \times 10^{-12}$ |
| M21119 | immunity | LYZ | 40.73 | $6.24 \times 10^{-10}$ |
| M14636 | metabolism | PYGL | 39.84 | $1.15 \times 10^{-10}$ |
| M26311 | calcium signaling | S100A9 | 38.96 | $3.60 \times 10^{-13}$ |
| M54992 | signaling | CD72 | 36.14 | $2.40 \times 10^{-9}$ |
| X16832 | protein degradation | CTSH | 35.26 | $1.81 \times 10^{-12}$ |
| M12529 | lipoprotein signaling | APOE | 34.50 | $3.95 \times 10^{-14}$ |
| M15395 | adhesion | ITGB2 | 34.02 | $1.74 \times 10^{-13}$ |
| Z74616 | extracellular matrix | COL1A2 | 34.02 | $8.06 \times 10^{-11}$ |
| HT2152 | receptor signaling | CD163 | 33.01 | $1.66 \times 10^{-12}$ |
| U97105 | pyrimidine metabolism | DPYSL2 | 32.52 | $2.22 \times 10^{-10}$ |
| U81787 | signaling | WNT10B | 32.50 | $1.77 \times 10^{-5}$ |
| HT3165 | receptor tyrosine kinase | AXL | 31.36 | $5.26 \times 10^{-11}$ |
| M83667 | transcription | CEBPD | 31.19 | $4.69 \times 10^{-10}$ |
| L33930 | receptor signaling | CD24 | 30.33 | $1.56 \times 10^{-14}$ |
| D83657 | calcium signaling | S100A12 | 29.91 | $6.58 \times 10^{-8}$ |
| M11313 | proteinase inhibitor | A2M | 29.91 | $1.07 \times 10^{-10}$ |
| M31158 | signaling | PRKAR2B | 29.91 | $2.20 \times 10^{-9}$ |
| U24577 | lipoprotein signaling | PLA2G7 | 29.78 | $2.08 \times 10^{-10}$ |
| M16279 | adhesion | MIC2 | 28.75 | $8.01 \times 10^{-11}$ |
| HT2811 | cell cycle | CDK8 | 28.32 | $6.53 \times 10^{-9}$ |

TABLE 4-continued

The 50 Most Significantly Downregulated Genes In Multiple Myeloma In Comparison With Normal Bone Marrow Plasma Cells

| Accession* | Function | Gene Symbol | Chi Square | WRS ‡ P Value |
|---|---|---|---|---|
| M26167 | cxc chemokine | PF4V1 | 27.35 | $4.68 \times 10^{-11}$ |
| U44111 | metabolism | HNMT | 27.24 | $2.07 \times 10^{-11}$ |
| X59871 | transcription | TCF7 | 26.79 | $7.16 \times 10^{-10}$ |
| X67235 | transcription | HHEX | 25.21 | $2.07 \times 10^{-10}$ |
| U19713 | calcium signaling | AIF1 | 25.21 | $2.57 \times 10^{-10}$ |
| Y08136 | apoptosis | ASM3A † | 24.74 | $3.30 \times 10^{-8}$ |
| M97676 | transcription | MSX1 | 24.58 | $9.80 \times 10^{-5}$ |
| M64590 | house keeping | GLDC | 24.27 | $4.10 \times 10^{-8}$ |
| M20203 | protease | ELA2 | 24.03 | $6.36 \times 10^{-12}$ |
| M30257 | adhesion | VCAM1 | 23.42 | $1.71 \times 10^{-10}$ |
| M93221 | mediates endocytosis | MRC1 | 23.30 | $1.15 \times 10^{-7}$ |
| S75256 | lipoprotein signaling | LCN2 | 23.30 | $4.17 \times 10^{-7}$ |
| U97188 | RNA binding | KOC1 † | 22.47 | $5.86 \times 10^{-9}$ |
| Z23091 | adhesion | GP5 | 22.47 | $7.58 \times 10^{-7}$ |
| M34344 | adhesion | ITGA2B | 21.99 | $8.00 \times 10^{-8}$ |
| M25897 | cxc chemokine | PF4 | 21.89 | $1.12 \times 10^{-8}$ |
| M31994 | house keeping | ALDH1A1 | 21.36 | $4.86 \times 10^{-9}$ |
| Z31690 | lipoprotein signaling | LIPA | 20.67 | $1.50 \times 10^{-9}$ |
| S80267 | signaling | SYK | 20.42 | $5.90 \times 10^{-5}$ |
| U00921 | signaling | LY117 | 18.83 | $1.57 \times 10^{-8}$ |

*Accession numbers listed are GENBANK ® numbers, except those beginning with "HT", are provided by the Institute of Genomic Research (TIGR).
† Gene symbol not HUGO approved.
‡ Wilcoxon rank sum test.

TABLE 5

The 70 Most Significantly Upregulated Genes in Multiple Myeloma in Comparison with Normal Bone Marrow Plasma Cells

| Accession* | Function | Gene Symbol † | Chi Square | WRS ‡ P Value |
|---|---|---|---|---|
| U09579 | cell cycle | CDKN1A | 53.33 | $3.65 \times 10^{-11}$ |
| U78525 | amino acid synthesis | EIF3S9 | 49.99 | $2.25 \times 10^{-12}$ |
| HT5158 | DNA synthesis | GMPS | 47.11 | $4.30 \times 10^{-12}$ |
| X57129 | histone | H1F2 | 46.59 | $5.78 \times 10^{-13}$ |
| M55210 | adhesion | LAMC1 | 45.63 | $1.34 \times 10^{-9}$ |
| L77886 | signaling, phosphatase | PTPRK | 45.62 | $5.42 \times 10^{-10}$ |
| U73167 | glycosaminoglycan catabolism | HYAL3 | 44.78 | $1.07 \times 10^{-10}$ |
| X16416 | oncogene, kinase | ABL1 | 43.10 | $3.96 \times 10^{-14}$ |
| U57316 | transcription | GCN5L2 | 43.04 | $1.36 \times 10^{-12}$ |
| Y09022 | protein glycosylation | NOT56L † | 42.05 | $5.53 \times 10^{-10}$ |
| M25077 | RNA binding | SSA2 | 41.26 | $1.69 \times 10^{-7}$ |
| AC002115 | mitochondrial respiration | COX6B | 41.16 | $2.16 \times 10^{-8}$ |
| Y07707 | transcription | NRF † | 37.59 | $4.79 \times 10^{-10}$ |
| L22005 | protein ubiquination | CDC34 | 34.50 | $2.89 \times 10^{-6}$ |
| X66899 | transcription | EWSR1 | 34.39 | $4.23 \times 10^{-8}$ |
| D50912 | RNA binding | RBM10 | 33.93 | $2.61 \times 10^{-6}$ |
| HT4824 | amino acid synthesis | CBS | 33.77 | $1.49 \times 10^{-6}$ |
| U10324 | transcription | ILF3 | 33.33 | $3.66 \times 10^{-11}$ |
| AD000684 | oncogene, transcription | USF2 | 32.18 | $7.41 \times 10^{-11}$ |
| U68723 | cell cycle | CHES1 | 31.68 | $1.03 \times 10^{-6}$ |
| X16323 | signaling, growth factor | HGF | 30.67 | $4.8210^{-9}$ |
| U24183 | metabolism | PFKM | 30.47 | $8.92 \times 10^{-10}$ |
| D13645 | unknown | KIAA0020 † | 30.47 | $7.40 \times 10^{-6}$ |
| S85655 | signaling, growth arrest | PHB | 29.37 | $1.32 \times 10^{-8}$ |
| X73478 | signaling, phosphatase | PPP2R4 | 28.32 | $6.92 \times 10^{-9}$ |
| L77701 | mitochondrial respiration | COX17 | 27.81 | $1.33 \times 10^{-6}$ |
| U20657 | oncogene, proteasome | USP4 | 27.71 | $2.31 \times 10^{-6}$ |
| M59916 | signaling, DAG signaling | SMPD1 | 27.49 | $3.52 \times 10^{-8}$ |
| D16688 | oncogene, DNA binding | MLLT3 | 27.24 | $6.97 \times 10^{-13}$ |
| X90392 | DNA endonuclease | DNASE1L1 | 26.98 | $4.72 \times 10^{-7}$ |
| U07424 | amino acid synthesis | FARSL | 26.93 | $1.66 \times 10^{-6}$ |
| X54199 | DNA synthesis | GART | 26.57 | $9.61 \times 10^{-11}$ |
| L06175 | unknown | P5-1 † | 26.57 | $5.16 \times 10^{-7}$ |
| M55267 | unknown | EVI2A | 25.92 | $3.79 \times 10^{-6}$ |
| M87507 | protein degradation | CASP1 | 25.78 | $5.46 \times 10^{-7}$ |
| M90356 | transcription | BTF3L2 | 25.78 | $9.68 \times 10^{-8}$ |
| U35637 | cytoskeletal matrix | NEB | 25.40 | $9.15 \times 10^{-6}$ |

TABLE 5-continued

The 70 Most Significantly Upregulated Genes in Multiple Myeloma
in Comparison with Normal Bone Marrow Plasma Cells

| Accession* | Function | Gene Symbol † | Chi Square | WRS ‡ P Value |
|---|---|---|---|---|
| L06845 | amino acid synthesis | CARS | 25.34 | $5.39 \times 10^{-8}$ |
| U81001 | DNA, nuclear matrix attachment | SNURF | 24.58 | $4.54 \times 10^{-5}$ |
| U76189 | heparan sulfate synthesis | EXTL2 | 24.58 | $7.28 \times 10^{-6}$ |
| U53225 | protein trafficking | SNX1 | 24.48 | $5.53 \times 10^{-7}$ |
| X04366 | protein degradation | CAPN1 | 24.35 | $1.26 \times 10^{-9}$ |
| U77456 | protein folding | NAP1L4 | 24.27 | $4.23 \times 10^{-10}$ |
| L42379 | signaling, growth arrest | QSCN6 | 24.27 | $1.28 \times 10^{-10}$ |
| U09578 | signaling, kinase | MAPKAPK3 | 24.27 | $2.35 \times 10^{-9}$ |
| Z80780 | histone | H2BFH | 24.27 | $3.44 \times 10^{-12}$ |
| HT4899 | oncogene, transcription | MYC | 24.27 | $1.77 \times 10^{-5}$ |
| M74088 | signaling, b-catenin regulator | APC | 23.94 | $1.50 \times 10^{-5}$ |
| X57985 | histone | H2BFQ | 23.90 | $3.25 \times 10^{-12}$ |
| X79882 | drug resistance | MVP | 23.47 | $1.77 \times 10^{-11}$ |
| X77383 | protein degradation | CTSO | 23.18 | $4.68 \times 10^{-7}$ |
| M91592 | transcription | ZNF76 | 23.16 | $1.12 \times 10^{-8}$ |
| X63692 | DNA methyltransferase | DNMT1 | 23.12 | $5.15 \times 10^{-11}$ |
| M60752 | histone | H2AFO | 21.60 | $1.46 \times 10^{-8}$ |
| M96684 | transcription | PURA | 21.25 | $4.54 \times 10^{-5}$ |
| U16660 | metabolism | ECH1 | 21.18 | $5.52 \times 10^{-5}$ |
| M86737 | DNA repair | SSRP1 | 20.60 | $2.62 \times 10^{-5}$ |
| U35113 | histone deacetylase | MTA1 | 20.60 | $6.67 \times 10^{-10}$ |
| X81788 | unknown | ICT1 | 20.42 | $2.97 \times 10^{-7}$ |
| HT2217 | signaling | MUC2A | 20.33 | $2.61 \times 10^{-7}$ |
| M62324 | unknown | MRF-1 † | 20.31 | $3.98 \times 10^{-9}$ |
| U09367 | transcription | ZNF136 | 20.30 | $7.72 \times 10^{-9}$ |
| X89985 | cytoskeletal matrix | BCL7B | 19.81 | $5.50 \times 10^{-9}$ |
| L19871 | transcription repression | ATF3 | 19.43 | $1.13 \times 10^{-6}$ |
| X69398 | adhesion | CD47 | 19.16 | $6.44 \times 10^{-7}$ |
| X05323 | signaling macrophage inhibitor | MOX2 | 19.16 | $8.58 \times 10^{-6}$ |
| X04741 | protein ubiquination | UCHL1 | 19.14 | $9.76 \times 10^{-5}$ |
| D87683 | vesicular transport | TSC1 | 19.12 | $6.81 \times 10^{-6}$ |
| D17525 | complement cascade | MASP1 | 18.81 | $4.05 \times 10^{-7}$ |

*Accession numbers listed are GENBANK ® numbers, except those beginning with "HT", which are provided by the Institute of Genomic Research (TIGR).
† Gene symbol not HUGO approved.
‡ Wilcoxon rank sum test.

EXAMPLE 9

Altered Expression of 14 Genes Differentiates Malignant From Normal Plasma Cells The present invention also sought to determine whether expression patterns of a minimum number of genes could be used to clearly differentiate normal, pre-neoplastic and malignant plasma cells. A multivariate step-wise discriminant analysis (MSDA) was applied to the top 50 significantly differentially expressed genes across the normal plasma cells (N=26) and multiple myeloma plasma cells (N=162) and a linear discriminant function between the normal plasma cell group and multiple myeloma group was observed. Both forward and backward variable selections were performed. The choice to enter or remove variables was based on a Wilks' $\lambda$ analysis, defined as follows: $\lambda(x) = \det W(x)/\det T(x)$ where $W(x)$ and $T(x)$ are the within-group and total scatter matrices respectively. Wilks' $\lambda$ can assume values ranging from 0 to 1. The significance of change in $\lambda$ was tested using the F statistic. At the end of multivariate step-wise discriminant analysis, only 14 genes were selected to compute the canonical discriminant functions (Table 6). The multivariate step-wise discriminant analysis selected the following equation: Discriminant score = HG4716×3.683−L33930×3.134+L42379×1.284+L77886×1.792+M14636×5.971−M26167×6.834+U10324×2.861−U24577×10.909+U35112×2.309+X16416×6.671−X64072×5.143+79822×5.53+Z22970×4.147+Z80780×2.64−87.795. The cutoff value was −3.3525. Values less than −3.3525 indicated the sample belonged to the normal group and values greater than −3.3525 indicated the sample belonged to the multiple myeloma group.

The 14 gene model was then applied to a training group consisting of 162 multiple myeloma and 26 normal plasma cell (data not shown). A cross-validation analysis was performed where samples were removed one at a time from the sample set, and training statistics and expression means for each class of the modified sample set were re-calculated. A predictive value using genes with a P value <0.05 in the modified sample set was generated. A 100% accurate prediction of the sample types in the training group was obtained.

Figure 5:
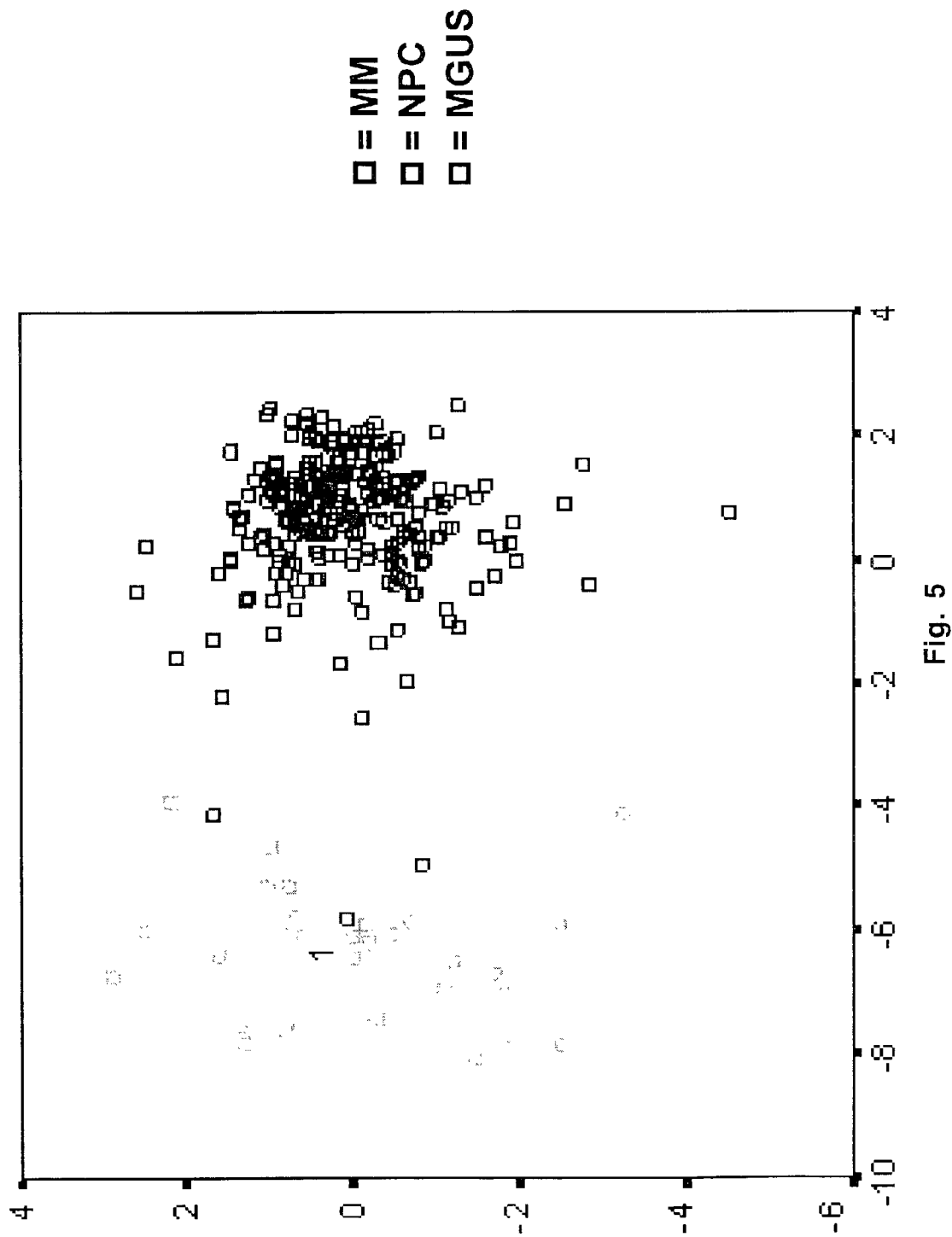
FIG. 5 shows multivariate discriminant analysis of 14 features of all normal plasma cells, MMs, monoclonal gammopathy of undetermined significance and multiple myeloma cell lines. This scatterplot resulted from the orthogonal projection of value per case onto the plane defined by the 2 centers. The green plots represent normal plasma cells; the blue plots represent multiple myeloma plasma cells and multiple myeloma cell lines; the pink plots represent monoclonal gammopathy of undetermined significance.

A validation group was then applied to the model. The multivariate step-wise discriminant analysis correctly classified 116 of 118 (98.31%) primary multiple myeloma samples and 8 of 8 (100%) of human myeloma cell lines as multiple myeloma. In addition, 6 of 6 normal plasma cell samples were classified as normal. Importantly, the model predicted that 6 of 7 monoclonal gammopathy of undetermined significance cases were multiple myeloma with 1 monoclonal gammopathy of undetermined significance case predicted to be normal (FIG. 5). The classification of the 6 monoclonal gammopathy of undetermined significance cases as multiple myeloma has important ramifications in that it suggests that cells in this benign condition have strong similarities to fully transformed cells. These results also have important implications in the eitology of monoclonal gammopathy of undetermined significance and its transition to overt multiple myeloma. The fact that the model classified monoclonal gammopathy of undetermined significance as multiple myeloma is consistent with recent studies that have shown monoclonal gammopathy of undetermined significance has chromosomal abnormalities e.g. translocations of the IGH locus and deletion of chromosome 13 that are also common in multiple myeloma. Future studies will be aimed at identification of gene expression patterns that can actually distinguish monoclonal gammopathy of undetermined significance from multiple myeloma. With the majority of the monoclonal gammopathy of undetermined significance cases being classified as multiple myeloma, the classification of a 1 monoclonal gammopathy of undetermined significance cases as normal m a y indicate 1) the patient does not have monoclonal gammopathy of undetermined significance or 2) the monoclonal gammopathy of undetermined significance cells represented a minority of the plasma cells in the sample. The monoclonal gammopathy of undetermined significance case and the 2 multiple myeloma cases classified as normal will be followed longitudinally to determine whether in the future the samples will shift to the multiple myeloma group.

Figure 6A:
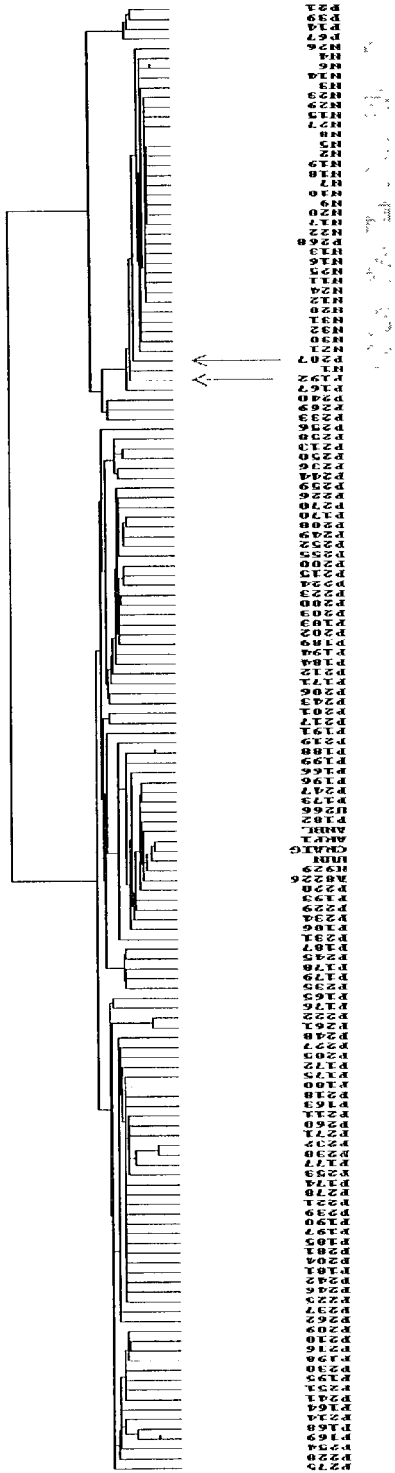
FIG. 6A shows 269 cases of multiple myeloma, 7 multiple myeloma cell lines, 7 monoclonal gammopathy of undetermined significance and 32 normal plasma cells samples clustered based on the correlation of 5,483 genes (probe sets). Two major branches contained two distinct cluster groups. The subgroup including normal plasma cell samples contained 1 monoclonal gammopathy of undetermined significance (green arrow) and 2 misclassified multiple myeloma samples (pink arrow).
Figure 6B:
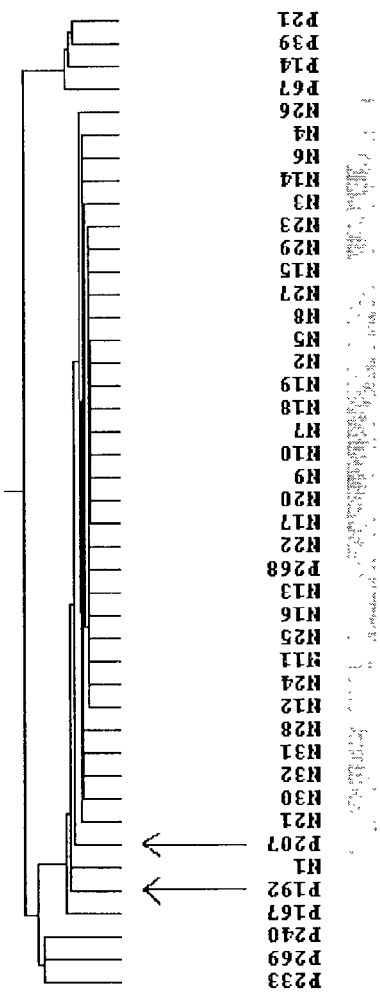
FIG. 6B shows amplified sample cluster showing samples connecting to the normal group.

In order to further validate the discriminant results, two-dimensional hierarchical clustering was performed on 927 genes with expression in at least one sample. The 118 multiple myeloma samples from the validation group, 32 normal plasma cells, 7 multiple myeloma cell lines, and 7 monoclonal gammopathy of undetermined significance were studied. Along the horizontal axis, experimental samples were arranged such that those with the most similar patterns of expression across all genes were placed adjacent to each other. Surprisingly, the two misclassified multiple myelomas and one monoclonal gammopathy of undetermined significance classified as normal plasma samples by discriminant analysis were also connected to the normal group in the cluster analysis (FIG. 6). This result indicated that the 14 gene discriminant model was consistent with a 927 gene hierarchical cluster model.

A survey of the function of the 14 genes in the above analysis showed several interesting features. The genes are not related in function and thus represent unique and independent genetic markers that can clearly be used as signatures of normal and malignant cells. Genes are associated with the microenvironment (ITGB2), cell transformation (ABL1) and drug resistance (MVP). It is possible that the deregulated expression of these genes may represent fundamental genetic abnormalities in the malignant transformation of plasma cells. For example, the ITGB2 gene encodes the glycoprotein β-2 integrin (CD18) which is critical to the formation of integrin heterodimers known to mediate cell-cell and/or cell-matrix adhesion events. As plasma cells constitutively express ICAM-1 and this molecule can be induced on bone marrow adherent cells, one can envisage a mechanism in which the ITGB2/ICAM-1 adhesion pathway mediates, adhesion among plasma cells as well as with cells in the bone marrow microenvironment. In human lymphomas, ITGB2 expression is found on tumor cells in low- and medium-grade malignant lymphomas, whereas absence of ITGB2 seems to be a characteristic of high-grade malignant lymphomas. Similar to other B lymphoma, the absence of ITGB2 might contribute to an escape from immunosurveillance in multiple myeloma.

In summary, the present invention describes a model that makes it possible to diagnosis multiple myeloma by the use of the differential expression of 14 genes. It is currently not clear whether deregulated expressions of these genes are involved in the creation of the malignant phenotype or whether they represent sentinels of some underlying yet to be recognized genetic defect(s). However, the functions of these genes suggest an underlying causal relationship between the deregulated expression and malignancy.

TABLE 6

Fourteen Gene Defining the Optimal Diagnosis Model

| Accession* | Gene Symbol | Wilks' Lambda | F to Remove | P number |
|---|---|---|---|---|
| HT5158 | GMPS | 0.090 | 10.99 | 0.0011 |
| L33930 | CD24 | 0.089 | 8.80 | 0.0034 |
| L42379 | QSCN6 | 0.087 | 4.24 | 0.0409 |
| L77886 | PTPRK | 0.088 | 6.46 | 0.0119 |
| M14636 | PYGL | 0.091 | 12.62 | 0.0005 |
| M26167 | PF4V1 | 0.091 | 12.39 | 0.0005 |
| U10324 | ILF3 | 0.090 | 11.98 | 0.0007 |
| U24577 | PLA2G7 | 0.107 | 44.28 | $3.23 \times 10^{-10}$ |
| U35113 | MTA1 | 0.088 | 6.22 | 0.0135 |
| X16416 | ABL1 | 0.099 | 27.65 | $4.04 \times 10^{-7}$ |
| X64072 | ITGB2 | 0.097 | 24.63 | $1.59 \times 10^{-6}$ |
| X79882 | MVP | 0.098 | 25.83 | $9.19 \times 10^{-7}$ |
| Z22970 | CD163 | 0.088 | 6.08 | 0.0146 |
| Z80780 | H2B | 0.092 | 14.58 | 0.0002 |

*Accession number listed are GENBANK ® numbers, except the one that begin with "HT", which is provided by the Institute of Genomic Research.

EXAMPLE 10

Differential Expression of 24 Genes can Accurately Differentiate Gene Expression Defined Subgroups of Multiple Myeloma The present invention also sought to determine whether expression patterns of a minimum number of genes could be used to clearly differentiate the gene expression-defined subgroups of multiple myeloma identified with hierarchical clustering of over 5,000 genes. As discussed above, two-dimensional cluster analysis of 263 multiple myeloma cases, 14 normal plasma cells, 7 MGUS and 7 multiple myeloma cell lines was performed. The sample dendrogram showed four subgroups of MM1, MM2, MM3 and MM4 containing 50, 75, 67, and 71 patients respectively. Then, the top 120 statistically significant differentially expressed genes as determined by Chi-square and Wilcoxon test of 31 normal plasma cells and 74 newly diagnosed multiple myeloma were chosen for use in a canonical discriminant analysis. By applying a linear regression analysis 24 genes were defined as predictors able to differentiate the multiple myeloma subgroups (Table 7).

The 24 genes predictor model was applied to a training group consisting of multiple myeloma plasma cell samples located in the center of each hierarchical clustering group [total N=129; MM1=23, MM2=33, MM3=34 and MM4=39]. A cross-validation analysis was performed on the training group where samples were removed one at a time from the sample set, and training statistics and expression means for each class of the modified sample set were re-calculated. A predictive value using genes with a P value <0.05 in the modified sample set was generated. The results of this analysis showed that a 100% accurate prediction of the sample types in the training group was obtained.

Figure 7:
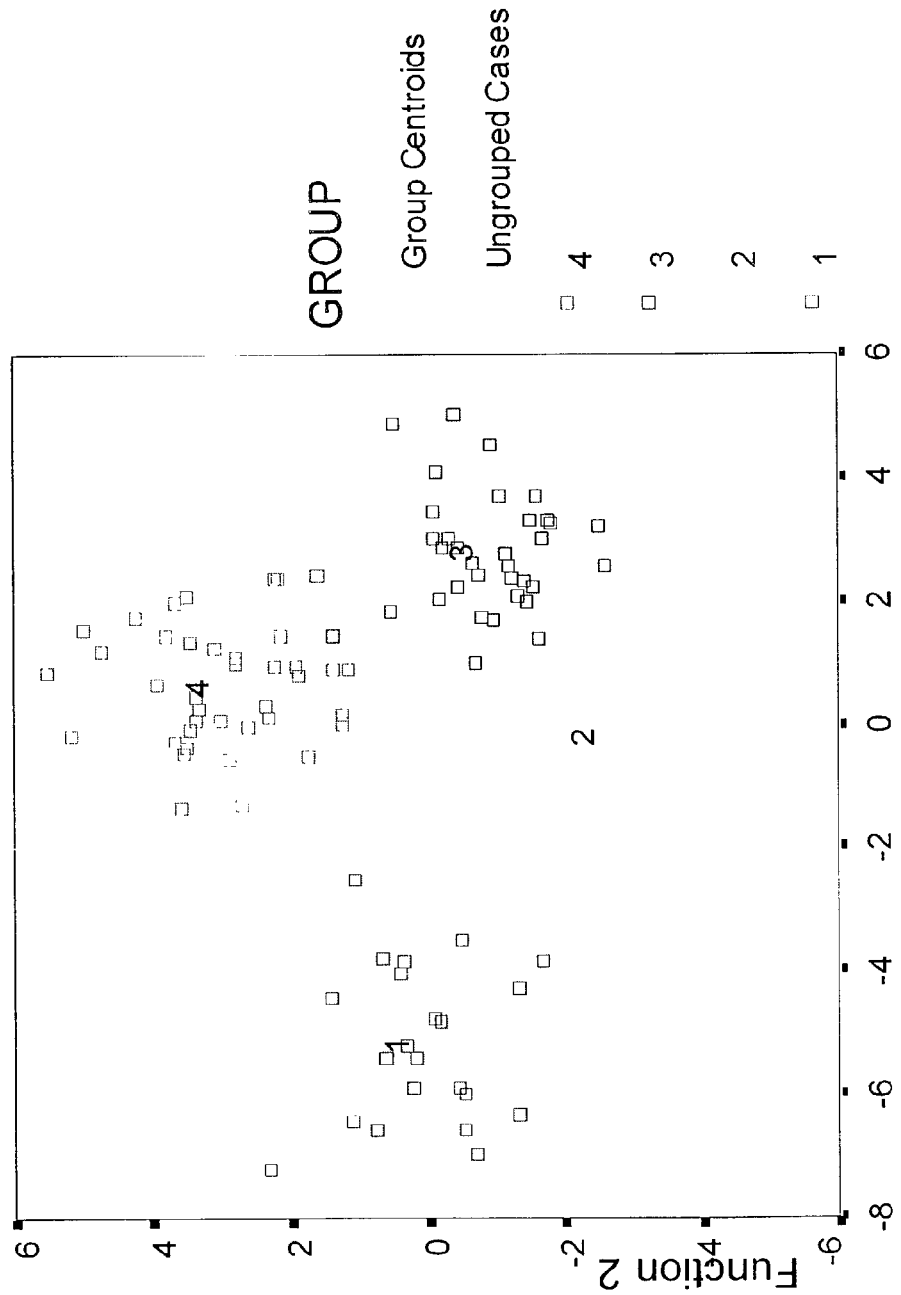
FIG. 7 shows multivariate discriminant analysis of 24 features of all multiple myeloma, monoclonal gammopathy of undetermined significance and multiple myeloma cell lines. This scatterplot resulted from the orthogonal projection of value per case onto the plane defined by the 4 centers. The red plots represent the MM1 subgroup; the green plots represent the MM2 subgroup; the blue plots represent the MM3 subgroup; and the pink plots represent the MM4 subgroup; the light blue plots are ungroup cases; and the large yellow plots represent the group centers.

A validation group was then applied to the model. The multivariate step-wise discriminant analysis correctly classified 116 of 134 (86.56%) primary multiple myeloma samples into different subgroups as compared with the subgroups defined by hierarchical clustering. Importantly, 7 of 7 (100%) of human myeloma cell lines were classified to MM4 as expected. In addition, the model predicted that 5 of 7 MGUS cases were MM1, and the remaining cases were predicted to be MM2 and MM3 respectively (FIG. 7).

TABLE 7

Twenty-Four Genes Defining Subgroups of Multiple Myeloma

| Accession No.* | Gene Symbol | Wilks' Lambda | F to Remove | P value |
|---|---|---|---|---|
| X54199 | GART | 0.004 | 3.13 | 0.0791 |
| M20902 | APOC1 | 0.005 | 4.05 | 0.0462 |
| X89985 | BCL7B | 0.005 | 4.47 | 0.0365 |
| M31158 | PRKAR2B | 0.005 | 5.07 | 0.0260 |
| U44111 | HNMT | 0.005 | 5.68 | 0.0186 |
| X16416 | ABL1 | 0.005 | 6.72 | 0.0106 |
| HT2811 | NEK2 | 0.005 | 8.35 | 0.0045 |
| D16688 | MLLT3 | 0.005 | 8.36 | 0.0045 |
| U57316 | CCN5L2 | 0.005 | 8.49 | 0.0042 |
| U77456 | NAP1L4 | 0.005 | 8.57 | 0.0040 |
| D13645 | KIAA00 | 0.005 | 9.17 | 0.0030 |
| M64590 | GLDC | 0.005 | 9.92 | 0.0020 |
| L77701 | COX17 | 0.005 | 10.01 | 0.0019 |
| U20657 | USP4 | 0.005 | 11.10 | 0.0011 |
| L06175 | P5-1 | 0.005 | 11.11 | 0.0011 |
| M26311 | S100A9 | 0.005 | 11.20 | 0.0011 |
| X04366 | CAPN1 | 0.005 | 11.67 | 0.0009 |
| AC002115 | COX6B | 0.006 | 13.64 | 0.0003 |
| X06182 | C-KIT | 0.006 | 13.72 | 0.0003 |
| M16279 | MIC2 | 0.006 | 16.12 | 0.0001 |
| M97676 | MSX1 | 0.006 | 16.41 | 0.0001 |
| U10324 | LIF3 | 0.006 | 19.66 | 0.0000 |
| S85655 | PHB | 0.007 | 20.63 | 0.0000 |
| X63692 | DNMT1 | 0.007 | 21.53 | 0.0000 |

*Accession number listed are GENBANK ® numbers, except the one that begin with "HT", which is provided by the Institute of Genomic Research.

EXAMPLE 11

Gene Expression "Spikes" in Subsets of Multiple Myeloma

A total of 156 genes not identified as differently expressed in the statistical analysis of multiple myeloma versus normal plasma cells, yet highly overexpressed in subsets of multiple myeloma, were also identified. A total of 25 genes with an AD spike greater than 10,000 in at least one sample are shown (Table 8). With 27 spikes, the adhesion associated gene FBLN2 was the most frequently spiked. The gene for the interferon induced protein 27, IFI27, with 25 spikes was the second most frequently spiked gene and contained the highest number of spikes over 10,000 (N=14). The FGFR3 gene (SEQ ID NO: 3; GENBANK® accession number M64347) was spiked in 9 of the 74 cases (FIG. 2A). It was the only gene for which all spikes were greater than 10,000 AD. In fact, the lowest AD value was 18,961 and the highest 62,515, which represented the highest of all spikes. The finding of FGFR3 spikes suggested that these spikes were induced by the multiple myeloma-specific, FGFR3-activating t(4;14) (p21;q32) translocation. To test the above hypothesis, RT-PCR for a t(4;14) (p21;q32) translocation-specific fusion transcript between the IGH locus and the gene MMSET was performed (data not shown). The translocation-specific transcript was present in all 9 FGFR3 spike samples but was absent in 5 samples that did not express FGFR3. These data suggested that the spike was caused by the t(4;14)(p21;q32) translocation.

The CCND1 gene was spiked with AD values greater than 10,000 in 13 cases. TRI-FISH analysis for the t(11;14)(q13;q32) translocation was performed (Table 9). All 11 evaluable samples were positive for the t(11;14)(q13;q32) translocation by TRI-FISH; 2 samples were not analyzable due to loss of cell integrity during storage. Thus, all FGFR3 and CCND1 spikes could be accounted for by the presence of either the t(4;14)(p21;q32) translocation or the t(11;14)(q13;q32) translocation respectively.

Figure 2:
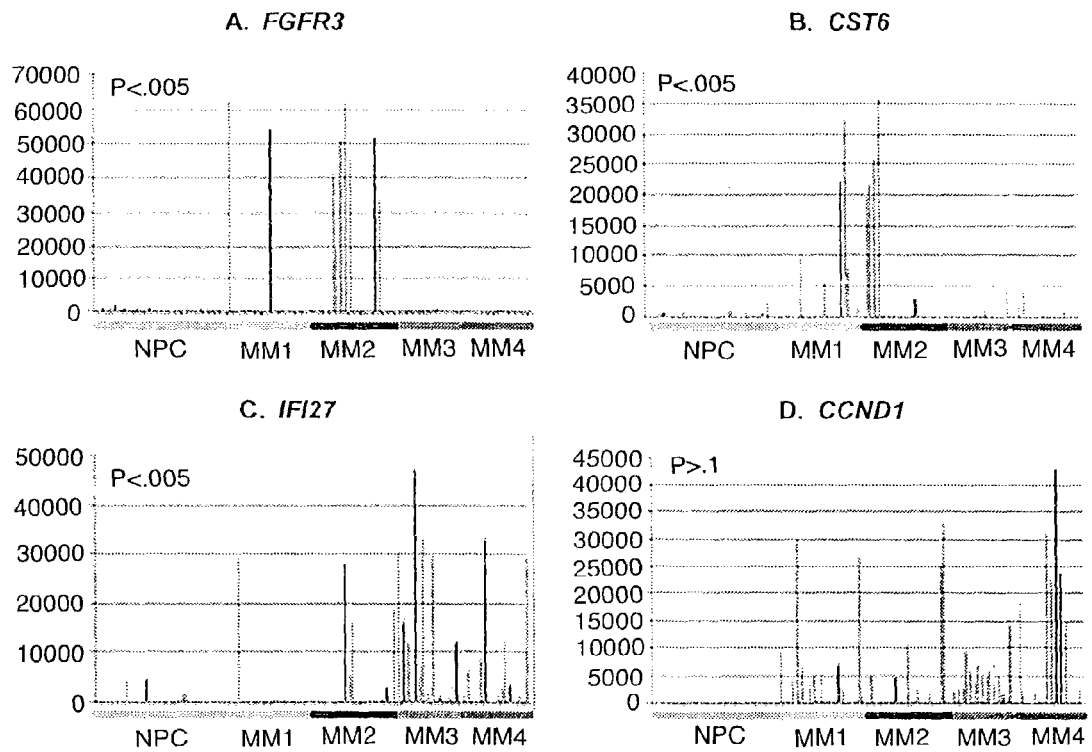
FIG. 2 shows the spike profile distributions of FGFR3, CST6, IFI27, and CCND1 gene expression. The normalized average difference (AD) value of fluorescence intensity of streptavidin-phycoerythrin stained biotinylated cRNA as hybridized to probes sets is on the vertical axis and samples are on the horizontal axis. The samples are ordered from left to right: normal plasma cells (NPCs) (green), MM1 (light blue), MM2 (dark blue), MM3 (violet), and MM4 (red). Note relatively low expression in 31 plasma cells and spiked expression in subsets of multiple myeloma samples. The P values of the test for significant nonrandom spike distributions are noted.

Next, the distribution of the FGFR3, CST6, IFI27, and CCND1 spikes within the gene expression-defined multiple myeloma subgroups was determined (FIG. 2). The data showed that FGFR3 and CST6 spikes were more likely to be found in MM1 or MM2 (P<0.005) whereas the spikes for IFI27 were associated with an MM3 and MM4 distribution (P<0.005). CCND1 spikes were not associated with any specific subgroup (P>0.1). It is noteworthy that both CST6 and CCND1 map to 11q13 and had no overlap in spikes. It remains to be tested whether CST6 overexpression is due to a variant t(11;14)(q13;q32) translocation. The five spikes for MS4A2 (CD20) were found in either the MM1 (3 spikes) or MM2 (2 spikes) subgroups (data not shown).

Figure 3A:
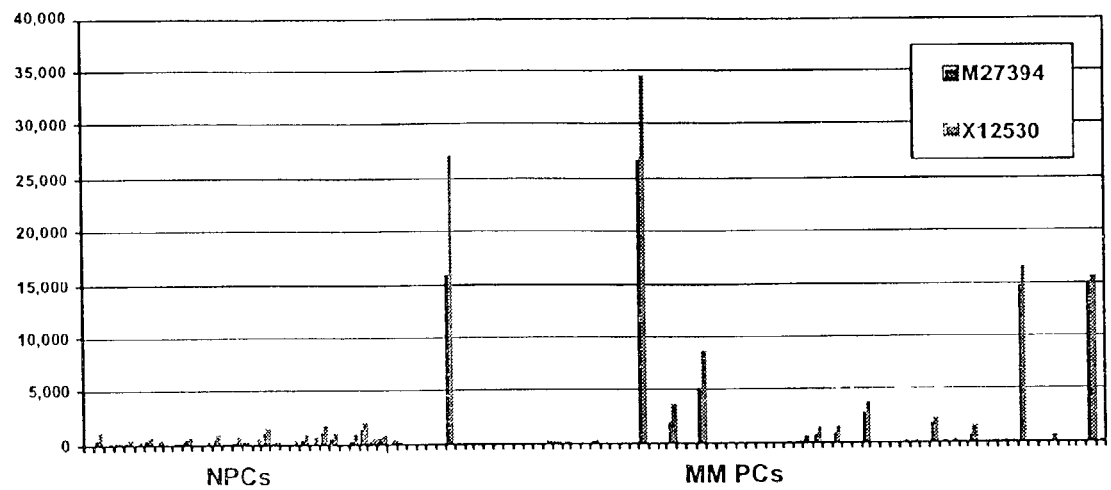
FIG. 3A shows GENECHIP (GeneChip) HUGENEFL (HuGeneFL) analysis of MS4A2 (CD20) gene expression. The normalized average difference (AD) value of fluorescence intensities of streptavidin-phycoerythrin stained biotinylated cRNA as hybridized to two independent probes sets (accession numbers M27394 (blue) and X12530 (red) located in different regions of the MS4A2 gene is on the vertical axis and samples are on the horizontal axis. Note relatively low expression in 31 normal plasma cells (NPCs) and spiked expression in 5 of 74 multiple myeloma samples (multiple myeloma plasma cells). Also note similarity in expression levels detected by the two different probe sets.
Figure 3B:
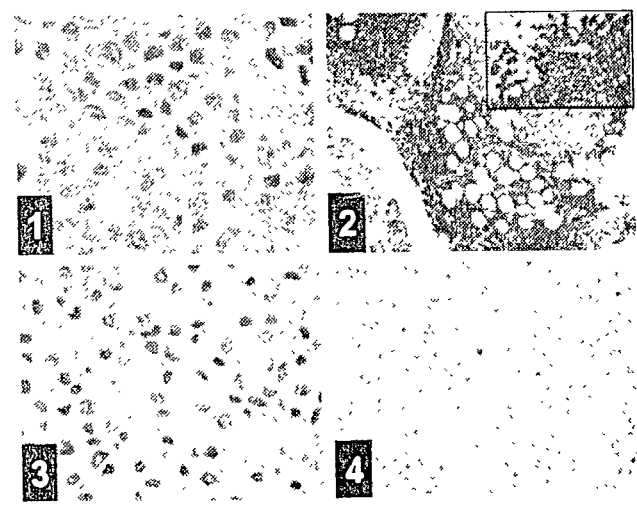
FIG. 3B shows immunohistochemistry for CD20 expression on clonal multiple myeloma plasma cells: (1) bone marrow biopsy section showing asynchronous type multiple myeloma cells (H&E, ×500); (2) CD20+ multiple myeloma cells (×100; inset ×500); (3) biopsy from a patient with mixed asynchronous and Marschalko-type multiple myeloma cells (H&E, ×500); and (4) CD20+ single lymphocyte and CD20− multiple myeloma cells (×200). CD20 immunohistochemistry was examined without knowledge of clinical history or gene expression findings.
Figure 4:
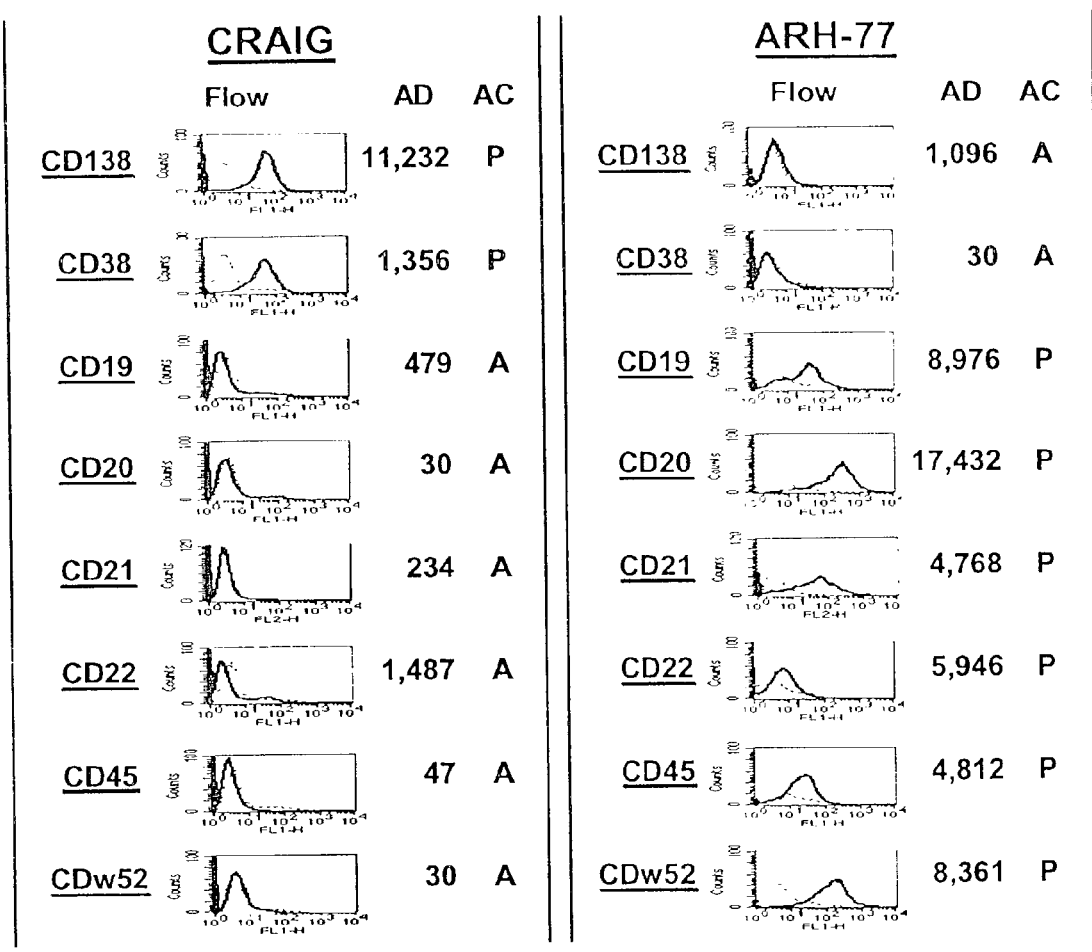
FIG. 4 shows the gene expression correlates with protein expression. Gene and protein expression of CD markers known to b e differentially expressed during B-cell differentiation were compared between the multiple myeloma cell line CAG (left panel) and the Epstein-Barr virus (EBV) transformed B-lymphoblastoid line ARH-77 (right panel). In both panels, the 8 CD markers are listed in the left column of each panel. Flow cytometric analysis of protein expression is presented in the second column; the average difference (AD) and absolute call (AC) values of gene expression are presented in the third and fourth columns. Note the strong expression of both the gene and protein for CD138 and CD38 in the CAG cells but the low expression in the ARH-77 cells. The opposite correlation is observed for the remaining markers.

The gene MS4A2 which codes for the CD20 molecule was also found as a spiked gene in four cases (FIG. 3A). To investigate whether spiked gene expression correlated with protein expression, immunohistochemistry for CD20 was performed on biopsies from 15 of the 74 multiple myeloma samples (FIG. 3B). All four cases that had spiked MS4A2 gene expression were also positive for CD20 protein expression, whereas 11 that had no MS4A2 gene expression were also negative for CD20 by immunohistochemistry. To add additional validation to the gene expression profiling, a comparison of CD marker protein and gene expression in the multiple myeloma cell line CAG and the EBV-transformed lymphoblastoid cell line ARH-77 were also performed (FIG. 4). The expression of CD138 and CD38 protein and gene expression was high in CAG but absent in ARH-77 cells. On the other hand, expression of CD19, CD20, CD21, CD22, CD45, and CDw52 was found to be strong in ARH-77 and absent in CAG cells. The nearly 100% coincidence of FGFR3 or CCND1 spiked gene expression with the presence of the t(4;14)(p14;q32) or t(11;14)(q13;q32) translocation; the strong correlation of CD20 and MS42A gene expression in primary multiple myeloma; and strong correlation of CD marker protein and gene expression in B cells and plasma cells represent important validations of the accuracy of the gene expression profiling disclosed herein.

TABLE 8

Genes with "Spiked" Expression in Plasma Cells from Newly Diagnosed Multiple Myeloma Patients

| Accession No.* | Function | Gene Symbol | # of Spikes | Spikes >10K | Max Spike |
|---|---|---|---|---|---|
| M64347 | signaling | FGFR3 | 9 | 9 | 62,515 |
| U89922 | immunity | LTB | 4 | 2 | 49,261 |

TABLE 8-continued

Genes with "Spiked" Expression in Plasma Cells
from Newly Diagnosed Multiple Myeloma Patients

| Accession No.* | Function | Gene Symbol | # of Spikes | Spikes >10K | Max Spike |
|---|---|---|---|---|---|
| X67325 | interferon signaling | IFI27 | 25 | 14 | 47,072 |
| X59798 | cell cycle | CCND1 | 6 | 13 | 42,814 |
| U62800 | cysteine protease inhibitor | CST6 | 17 | 6 | 36,081 |
| U35340 | eye lens protein | CRYBB1 | 4 | 1 | 35,713 |
| X12530 | B-cell signaling | MS4A2 | 5 | 5 | 34,487 |
| X59766 | unknown | AZGP1 | 18 | 4 | 28,523 |
| U58096 | unknown | TSPY | 4 | 1 | 23,325 |
| U52513 | interferon signaling | IFIT4 | 5 | 2 | 21,078 |
| X76223 | vesicular trafficking | MAL | 19 | 5 | 20,432 |
| X92689 | O-linked glycosylation | GALNT3 | 4 | 1 | 18,344 |
| D17427 | adhesion | DSC3 | 8 | 7 | 17,616 |
| L11329 | signaling | DUSP2 | 14 | 1 | 15,962 |
| L13210 | adhesion, macrophage lectin | LGALS3BP | 8 | 2 | 14,876 |
| U10991 | unknown | G2† | 7 | 1 | 14,815 |
| L10373 | integral membrane protein | TM4SF2 | 4 | 2 | 14,506 |
| U60873 | unknown | 137308 | 12 | 1 | 12,751 |
| M65292 | complement regulation | HFL1 | 9 | 1 | 12,718 |
| HT4215 | phospholipid transport | PLTP | 23 | 1 | 12,031 |
| D13168 | growth factor receptor | ENDRB | 18 | 1 | 11,707 |
| AC002077 | signaling | GNAT1 | 21 | 1 | 11,469 |
| M92934 | growth factor | CTGF | 4 | 1 | 11,201 |
| X82494 | adhesion | FBLN2 | 27 | 7 | 10,648 |
| M30703 | growth factor | AR | 5 | 1 | 10.163 |

*Accession numbers listed are GENBANK ® numbers, except those beginning with "HT", which are provided by the Institute of Genomic Research (TIGR).
†Gene symbol not HUGO approved.

TABLE 9

Correlation of CCND1 Spikes with FISH-Defined t(11;14)(q13;q32)

| GC PT* | CCND1 Spike (AD value)† | FISH t(11;14) | Percent PCs with Translocation | Cells Counted |
|---|---|---|---|---|
| P168 | 42,813 | Yes | 59% | 113 |
| P251 | 33,042 | Yes | 80% | 124 |
| P91 | 31,030 | Not done | — | — |
| P99 | 29,862 | Yes | 65% | 111 |
| P85 | 26,737 | Yes | 92% | 124 |
| P241 | 25,611 | Yes | 96% | 114 |
| P56 | 23,654 | Yes | 100% | 106 |
| P63 | 22,358 | Yes | 98% | 104 |
| P199 | 18,761 | Yes | 60% | 35 |
| P107 | 15,205 | Yes | 100% | 147 |
| P75 | 14,642 | Yes | 100% | 105 |
| P187 | 14,295 | Yes | 25% | 133 |
| P174 | 10.594 | Not done | — | — |

*GC PT = patient identifier;
†AD = average difference call.

EXAMPLE 12

Endothelin B Receptor as Potential Therapeutic Target of Multiple Myeloma

Figure 8A:
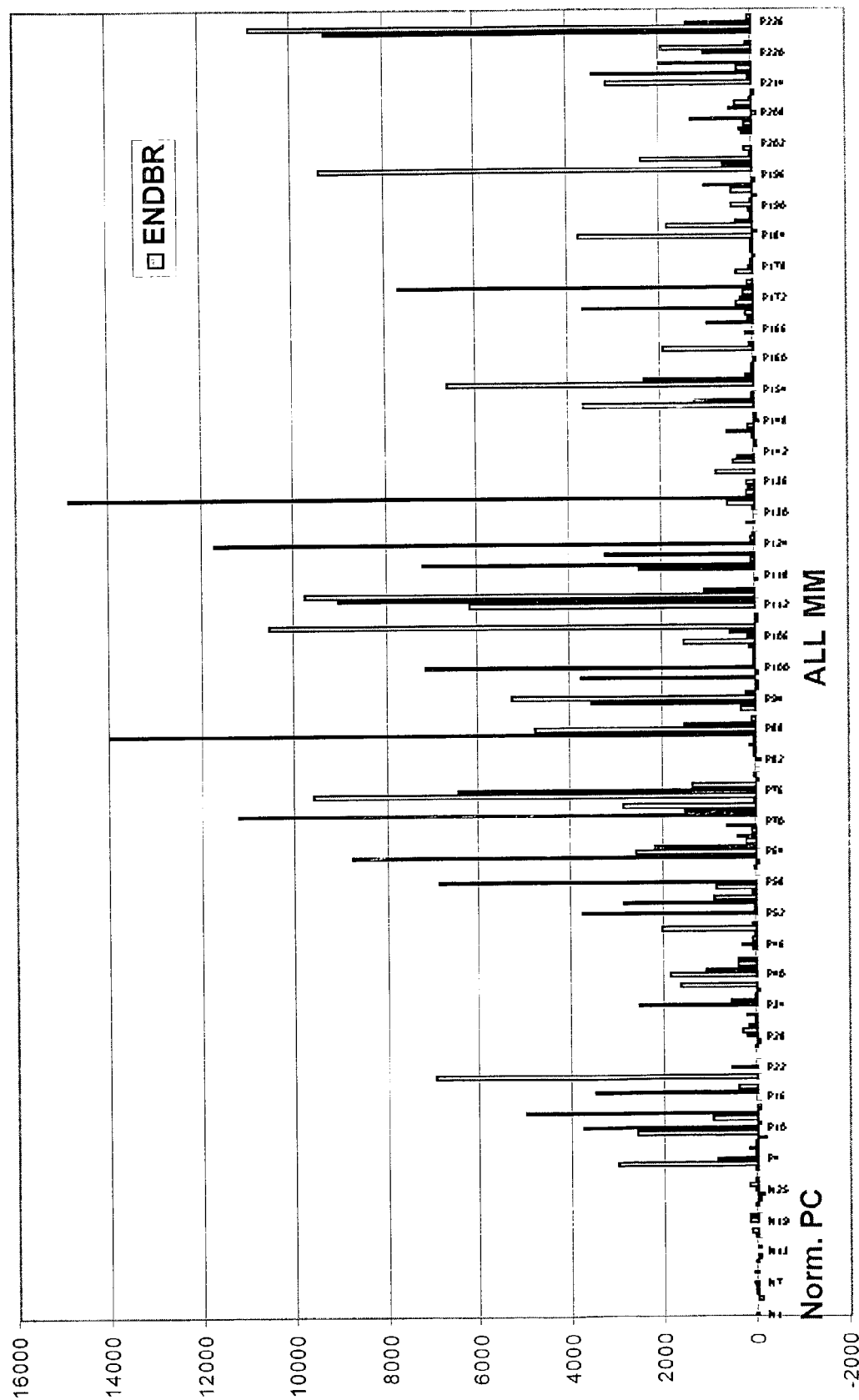
FIG. 8A shows endothelin B receptor (ENDBR) expression in normal plasma cells and in approximately 200 myeloma patients starting with P1 through P226 as indicated by the mean fluorescent intensity of the microarry data depicted on the Y axis.
Figure 8B:
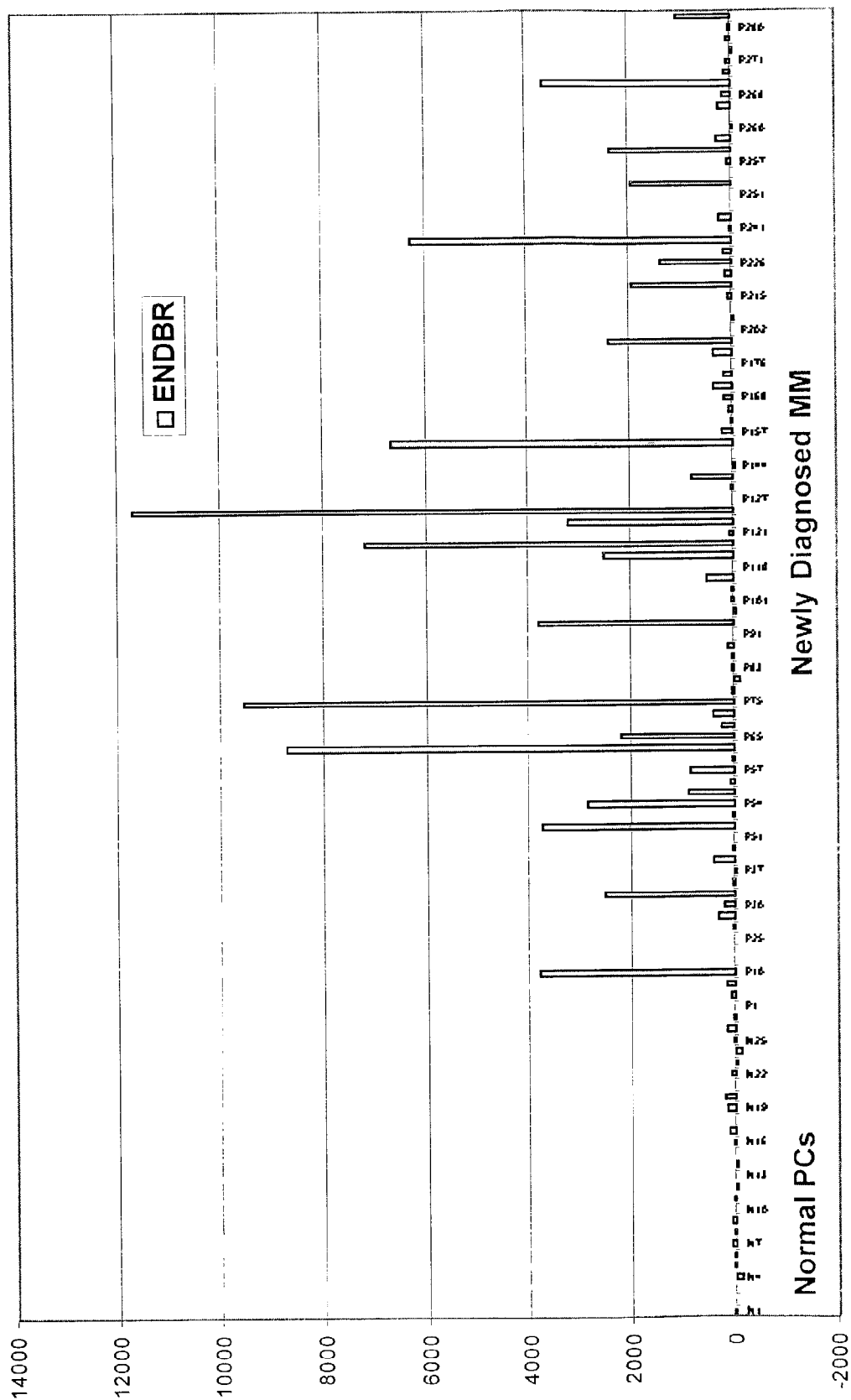
FIG. 8B shows endothelin B receptor expression in normal plasma cells and in newly diagnosed myeloma patients.

As disclosed above, the present invention has identified a number of genes that have significantly different expression levels in plasma cells derived from multiple myeloma compared to those of normal control. Genes that are significantly up-regulated or down-regulated in multiple myeloma are potential therapeutic targets of multiple myeloma. Examples of these genes are listed in Tables 4, 5 and 8. Among these differentially expressed genes is endothelin B receptor (ENDBR). This gene was not expressed in normal plasma cells, but does show highly elevated expression in a subset of myeloma. In fact, this gene now appears to be highly expressed in between 30-40% of myeloma patients. FIG. 8 shows a comparison of ENDBR expression in normal plasma cells and in approximately 200 myeloma patients starting with P1 through P226. ENDBR was either off or highly expressed in multiple myeloma patients (FIG. 8A). Levels of ENDBR expression levels were approximately the same in newly diagnosed and previously treated patients, suggesting that the activation is not a progression event (FIG. 8B).

Several important features of ENDBR should be noted. The ENDBR gene is located on chromosome 13. This is of potential significance given that abnormalities in chromosome 13 such as translocation or deletions represent one of the most powerful negative risk factors in multiple myeloma. Thus, it is possible that the hyperactivation of ENDBR expression could be an indicator of poor prognosis for multiple myeloma. There are also extensive reports linking endothelin signaling to cell growth, and endothelins have been shown to activate several key molecules with documented pathological roles in plasma cell tumorigenesis. Of note are the c-MYC oncogene, a gene that is activated in 100% of mouse plasmacytomas and hyperactivated in many primary human myeloma cells, and IL-6 which is a major growth and survival factor for myeloma cells. The endothelins also appear to exert their signaling through the phospholipase C pathway, a major signaling pathway in B-cells. Moreover, a recent paper reported that blocking endothelin signaling resulted in inhibition of the proliferation of Kaposi's sarcoma cells.

Figure 9B:
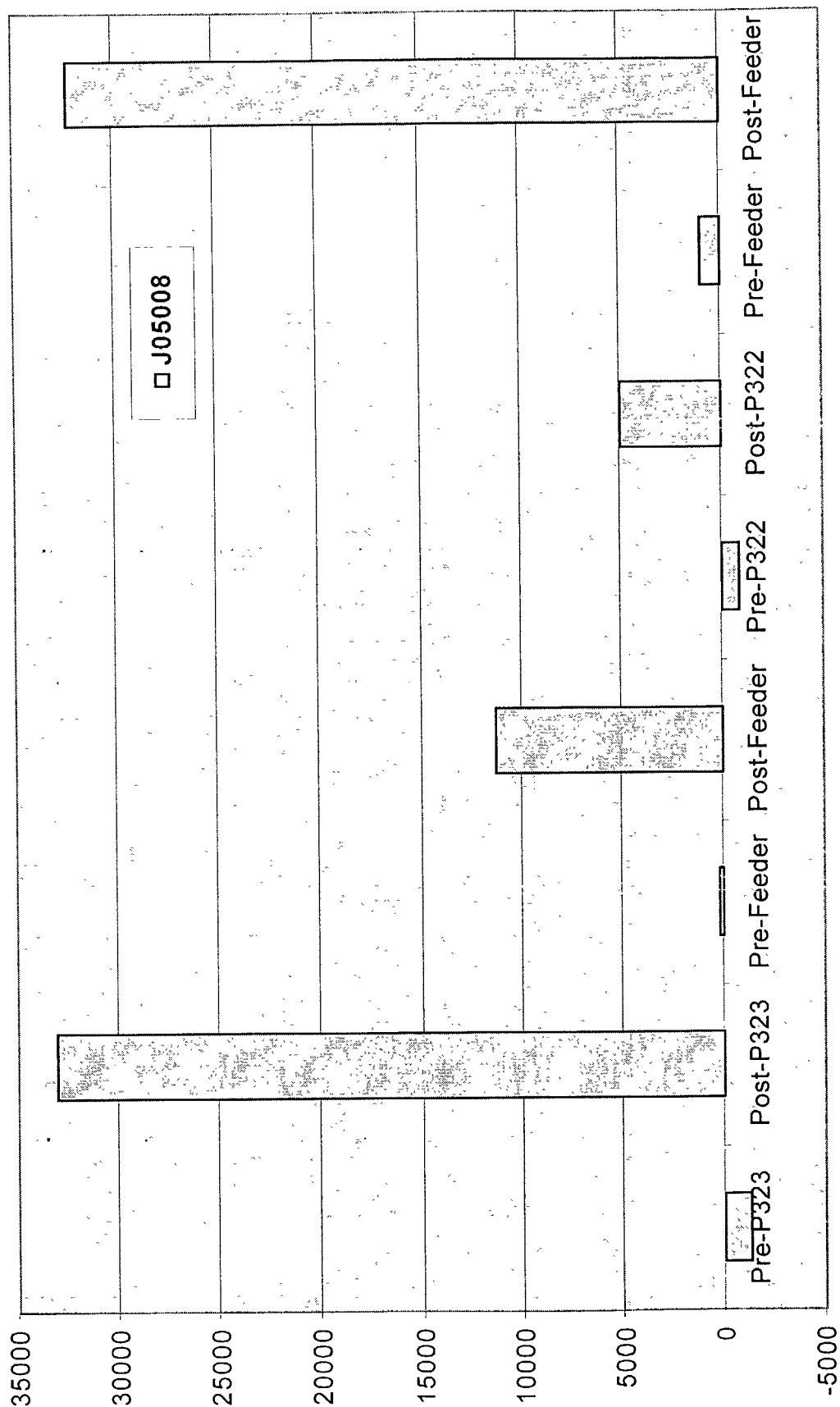
FIG. 9B shows the expression of endothelin 1 in feeder cells and myeloma cells P323 and P322 before and after co-culture.

When the tumor cells of multiple myeloma patients were taken out of the microenvironment of bone marrow, the tumor cells did not appear to express endothelins genes in a large proportion of the population. They lack expression of the endothelin 1, 2 and 3 in most cases. However, when the myeloma cells were taken out of the bone marrow and cultured for 48-72 hours on proprietary feeder layer that mimics the bone marrow microenvironment, endothelin 1 gene expression was massively up-regulated in both the myeloma cells P323 and P322 as well as the feeder layer (FIG. 9). Hence, a major variable within multiple myeloma may be the availability of endothelins. Enhanced production of endothelins coupled with up-regulated expression of ENDBR in local areas may contribute to the neoplastic phenotype of multiple myeloma, and blocking endothelins and endothelin receptor interaction may disrupt the development of the malignant phenotype.

EXAMPLE 13

Comparative Gene Expression Profiling of Human Plasma Cell Differentation

Examples 13-15 describe global gene expression profiling that reveals distinct changes in transcription associated with human plasma cell differentiation.

Data presented below demonstrate for the first time that highly purified plasma cells could be isolated from two unique hematopoietic organs, tonsil and bone marrow. This purification of millions of cells eliminated background "noise" from non-specific cell types (see FIG. 10), thereby allowing accurate genetic profile and characterization of these samples using highly sensitive gene expression profiling technology. The results disclosed herein characterized molecular transcription changes associated with different cell stages and especially distinguishing differences in plasma cell, a cell previously thought to represent an end-stage differentiation product based on morphological criterion.

The $CD19^+$ tonsil B cells and $CD138^+$ plasma cells isolated from tonsil and bone marrow used in the study represent homogeneous populations with unique phenotypic characteristics. Thus, results presented are based on well-characterized cells as shown by flow cytometry, morphology, and expression of cIg. These results are important because although great efforts have been made to understand B cell development, little is known about plasma cells, most likely due to their scarcity with most previous studies focusing only on flow cytometric characterizations.

Another unique finding from the results is that B cells and plasma cells segregated into two branches using a hierarchical gene expression cluster analysis. Further, within the plasma cell branch, tonsil plasma cells could be distinguished from bone marrow plasma cells, indicating that the cells represent unique stages of development as suspected from their derivation from unique hematopoietic organs. Genes identified herein (e.g., cell surface markers and transcription factors) matched those previously identified as distinguishing late-stage B cell development. In addition to the novel genes found, previously identified genes followed expected patterns of up- and down-regulation and matched those genes already shown to be linked to plasma cell differentiation or essential transcription factors for plasma cell differentiation.

Although cells at distinct stages of B cell development express CD19, it is likely that the majority of the tonsil B cells studied here represent germinal center centroblasts. It is known that centrocytes and centroblasts of germinal centers can be differentiated based on the expression of CD44 (centrocytes, $CD44^+$; centroblasts, $CD44^-$). Expression of the CD44 gene was undetectable in the tonsil B cell samples used in this study. In addition, the high level of expression of genes linked to proliferation, e.g. MKI67, PCNA, and CCNB1 (data not shown) suggests blasts make up the largest population of cells among the tonsil B cells. Finally, MYBL, whose expression is a marker of $CD38^+$ $CD39^-$ centroblasts, was found to be highly expressed in the tonsil B cells, down-regulated in tonsil plasma cells (P=0.00068), and extinguished in bone marrow plasma cells. Because centroblasts have already undergone switch recombination, the tonsil B cells studied here represent an optimal late stage B cell population to use in a comparative study of gene expression changes associated with early plasma cell differentiation.

Figure 10:
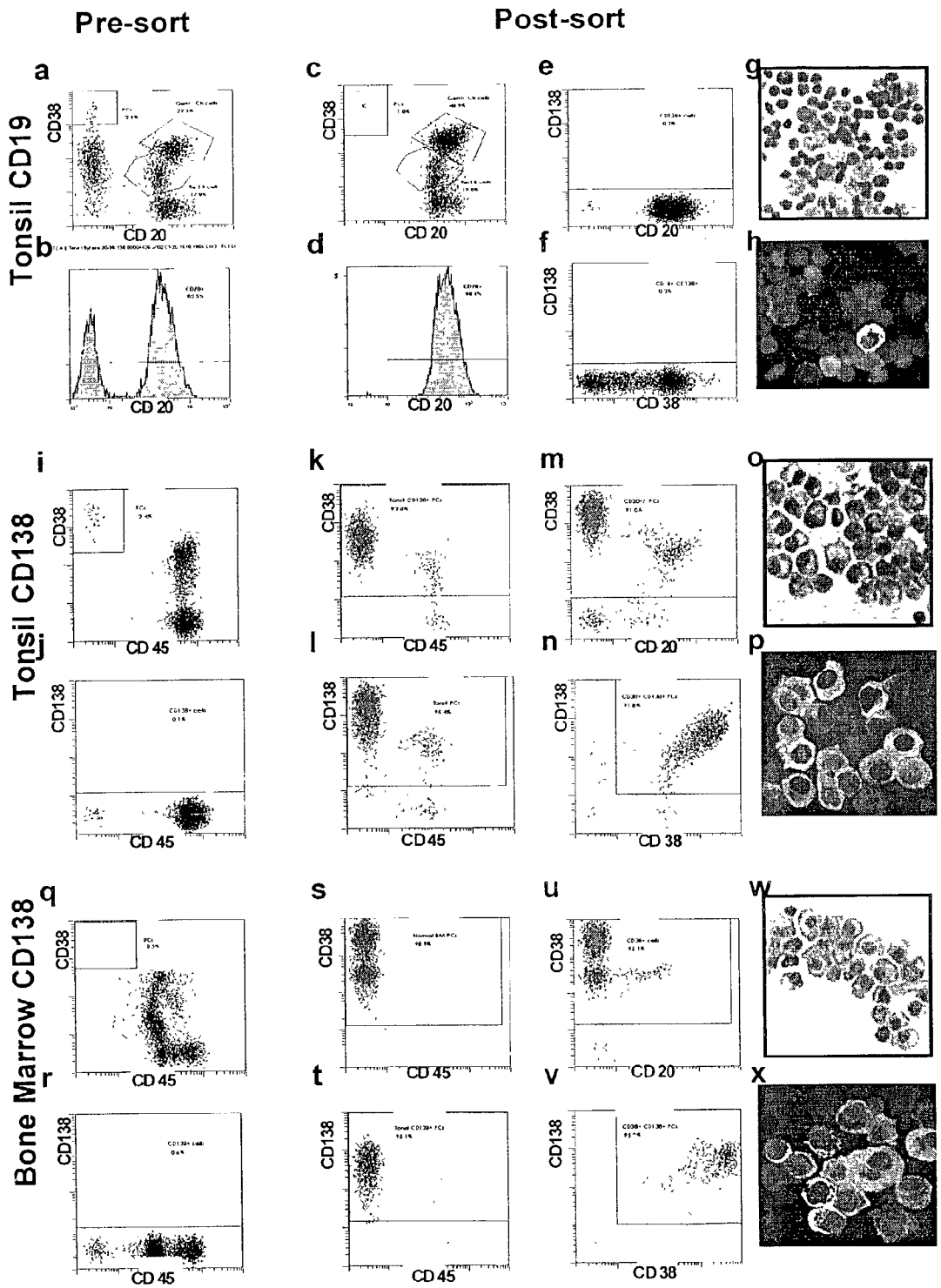
FIG. 10 shows flow cytometric, immunofluorescence and cytological analysis of normal B cell and plasma cell samples.

A representative analysis of normal cell types used in this study is presented in FIG. 10. FACs analysis of the tonsil preparations before sorting indicated that $CD20^{hi}/CD38^{lo}$ cells represented 70% and $CD38+/CD20^-0$ cells represented 30% of the population (FIGS. 10a, b). After anti-CD19 immunomagnetic bead selection, the $CD20^{hi}/CD38^{lo/-}$cells were enriched to 98% and the $CD38^+/CD20^-$, $CD138^-/CD20^+$, and $CD138^-/CD38^+$ fractions represented 1% of the population (FIGS. 10b, c, e, f). Cell morphology of the purified fraction also showed that the majority of cells had typical B cell morphology (FIG. 10g). Immunofluorescence microscopy with anti-kappa and anti-lambda antibodies indicated a slight contamination with $cIg^+$ $CD19^+$ cells (FIG. 10h).

Before tonsil plasma cell isolation, FACs analysis of the tonsil mononuclear fractions indicated that $CD38^{hi}/CD45^-$ (FIG. 10i) and $CD138^{hi}/CD45^-$ cells (FIG. 10j) represented 2.4% of the population. After anti-CD138 immunomagnetic bead sorting, cells with a plasma cell phenotype that was either $CD38^{hi}/CD45^{lo}$ (95%), $CD138^{hi}/CD45^{lo}$ (94%), $CD38^{h}/CD20^{lo}$ (91%), or $CD138^{hi}/CD38^{hi}$ (92%) were greatly enriched (FIGS. 10k, l, m, n). The tonsil CD138- selected cells were also found to have a typical plasma cell morphology with increased cytoplasmic to nuclear ratio of prominent perinuclear Hoff or endoplasmic reticulum (FIG. 10o) and >95% of the cells were cIg positive (FIG. 10p).

FACs analysis prior to anti-CD138 immunomagnetic bead sorting of bone marrow mononuclear cell samples showed similar but distinct profiles in comparison with the tonsil preparations. $CD38^{hi}/CD45^{int}$ and $CD138^{hi}/CD45^{int}$ fractions showed more cells with lower expression of CD45 and a higher percentage of $CD138^+$ cells in the bone marrow plasma cells (FIGS. 10q, r). FACS analysis after purification showed that the $CD38^{hi}/CD45^-0$ and $CD38^{hi}/CD20^{lo}$ cells were enriched to 99% and 91%, respectively (FIGS. 10s, u). Differences between tonsil plasma cells and bone marrow plasma cells after sorting were also evident, in that whereas the tonsil plasma cells had clear evidence of $CD38^+/CD45^+$ and $CD38^+/CD20^+$ cells, these fractions were greatly reduced in the bone marrow CD138-selected cells. Bone marrow plasma cells also expressed higher levels of CD38 than the tonsil plasma cells (FIGS. 10s, k). The $CD138^{hi}/CD45^-$ and $CD138^{hi}/CD38^{hi}$ populations represented 96% and 95% of the bone marrow plasma cell population (FIGS. 10t, v), again with a reduced amount of $CD45^+$ cells and higher percentage of $CD38^+$ cells as compared with tonsil plasma cells. As with the tonsil plasma cells, the majority of the bone marrow cells had plasma cell morphology (FIG. 10w) and were cIg positive (FIG. 10x). Thus, immunomagnetic bead selection resulted in the purification of a relatively homogenous tonsil B cell population and distinct plasma cell populations from two different organs, likely representing cells at different stages of maturation.

Having demonstrated the phenotypic characteristics of the cells, the global mRNA expression was then analyzed in 7 tonsil B cell, 11 tonsil plasma cell, and 31 bone marrow plasma cell samples using the Affymetrix high-density oligonucleotide microarray interrogating approximately 6800 named and annotated genes. The mean value of the AD expression level of genes for the CD markers used in the cell analysis, as well as other CD markers, chemokine receptors, apoptosis regulator, and a panel of transcription factors were analyzed across the normal samples (Table 10). CD45 was found to be highly expressed on tonsil B cells, with lower expression on tonsil plasma cells, and absent on bone marrow plasma cells. The genes for CD20, CD79B, CD52, and CD19 showed CD45-like expression patterns with progressive down-regulation from tonsil B cells to tonsil plasma cells. Although CD21 showed no significant change from tonsil B cells to tonsil plasma cells, the gene was down-regulated in bone marrow plasma cells. CD22, CD83, and CD72 showed progressive down-regulation.

Consistent with the FACS analysis, Syndecan-1 (CD138) and CD38, key plasma cell differentiation antigens, were absent or weakly expressed on tonsil B cells, with intermediate levels on tonsil plasma cells, and highest expression on bone marrow plasma cells. The intermediate level of CD138 expression is likely a direct reflection of the heterogeneous mixture of CD138$^+$ cells in the tonsil plasma cell fraction (see above) with some cells being highly CD138$^+$ and others weakly positive but still able to be sorted based on surface expression of CD138. CD38 expression showed the progressive increase seen with CD138 in the normal cells.

It was also observed that the CD63 gene was significantly up-regulated in bone marrow plasma cells. This is the first indication that this marker may be differentially regulated during plasma cell differentiation. The gene for CD27 showed significant up-regulation from the B cell to tonsil plasma cell transition, whereas bone marrow plasma cells and tonsil plasma cells showed similar levels.

Transcription factors differentially expressed in plasma cell development showed the expected changes. IRF4 and XBP1 were significantly up-regulated in tonsil and bone marrow plasma cells and CTIIA, BCL6, and STAT6 were down-regulated in the plasma cell samples. BSAP (PAX5) did not show the expected changes, but it is believed that this was due to an ineffective probe set for the gene because the BSAP target gene, BLK, did show the expected down-regulation in the tonsil and bone marrow plasma cells. Interestingly, whereas MYC showed significant down-regulation in the tonsil B cell to tonsil plasma cell transition, the gene was reactivated in bone marrow plasma cells to levels higher than seen in the tonsil B cells. Whereas the chemokine receptors CXCR4 and CXCR5 showed down-regulation in the tonsil B cell to tonsil plasma cell transition, CXCR4 showed a MYC-like profile in that the gene was reactivated in bone marrow plasma cells. The BCL2 homologue BCL2A1 also showed the expected changes. Thus, gene expression patterns of cell surface markers are consistent with phenotypic patterns and genes known to be strongly associated with plasma cell differentiation showed anticipated patterns. These data support the notion that the tonsil B cells, tonsil plasma cells, and bone marrow plasma cells represent distinct stages of B-cell differentiation and that gene expression profiling of these cells can be used to gain a better understanding of the molecular mechanisms of differentiation.

TABLE 10

Gene Expression Of CD Marker And Proteins Known To Be Differentially Expressed During Plasma Cell Differentiation

| Accession | Symbol | TBC | TPC | BPC |
|---|---|---|---|---|
| Y00062 | CD45 | 11495 ± 2198 | 4979 ± 2522 | 1385 ± 706 |
| M27394 | CD20 | 23860 ± 5494 | 3799 ± 2977 | 289 ± 358 |
| M89957 | CD79B | 14758 ± 3348 | 4696 ± 2440 | 1243 ± 1357 |
| X62466 | CD52 | 14576 ± 2395 | 4348 ± 2074 | 2831 ± 1002 |
| M84371 | CD19 | 12339 ± 1708 | 6174 ± 1345 | 2852 ± 852 |
| M26004 | CD21 | 8909 ± 1640 | 5434 ± 4053 | 458 ± 140 |
| X59350 | CD22 | 10349 ± 1422 | 5356 ± 1610 | 1929 ± 612 |
| Z11697 | CD83 | 9201 ± 1900 | 2380 ± 1087 | 392 ± 403 |
| M54992 | CD72 | 6177 ± 1620 | 865 ± 554 | 454 ± 548 |
| Z48199 | CD138 | 719 ± 519 | 9935 ± 3545 | 24643 ± 6206 |
| D84276 | CD38 | 3122 ± 967 | 9833 ± 3419 | 14836 ± 3462 |
| X62654 | CD63 | 2310 ± 431 | 6815 ± 1582 | 16878 ± 3305 |
| M63928 | CD27 | 6235 ± 1736 | 15937 ± 6691 | 16714 ± 4442 |
| M31627 | XBP1 | 12978 ± 1676 | 54912 ± 13649 | 49558 ± 10798 |
| U52682 | IRF4 | 1863 ± 630 | 8422 ± 3061 | 11348 ± 3118 |
| U00115 | BCL6 | 7979 ± 1610 | 3303 ± 2070 | 618 ± 335 |
| X74301 | CIITA | 1553 ± 263 | 236 ± 217 | 113 ± 82 |
| U16031 | STAT6 | 1314 ± 512 | 386 ± 335 | 191 ± 187 |
| S76617 | BLK | 3654 ± 1551 | 388 ± 592 | 95 ± 86 |
| X68149 | CXCR5 | 3381 ± 1173 | 183 ± 299 | 92 ± 183 |
| U29680 | BCL2A1 | 3290 ± 1073 | 1121 ± 817 | 483 ± 209 |
| L00058 | MYC | 1528 ± 474 | 348 ± 239 | 2103 ± 903 |
| L06797 | CXCR4 | 11911 ± 2093 | 6673 ± 3508 | 18033 ± 5331 |

Accession = GENBANK ® accession number.
Symbol = HUGO approved gene symbol.
The numbers in the columns under the tonsil B cell (TBC), tonsil plasma cell (TPC), and bone marrow plasma cell (BPC) samples represent the mean average difference (AD) value ± the standard deviation (STD) for the given gene. Differences in expression across comparisons were significant (P < 0.01) unless indicated in bold.

EXAMPLE 14

Identification of Differentially Expressed Genes in the Tonsil B Cell to Tonsil Plasma Cell and in the Tonsil Plasma Cell to Bone Marrow Plasma Cell Transitions A more detailed and comprehensive evaluation was performed to determine gene expression changes that accompany the transition of tonsil B cells to tonsil plasma cells and the changes that occur as the immature tonsil plasma cells exit the lymph node germinal center and migrate to the bone marrow. To reveal global expression distinctions among the samples, hierarchical cluster analysis was performed with 4866 genes in 7 tonsil B cell, 7 tonsil plasma cell, and 7 bone marrow plasma cell cases (FIG. 11). As expected, this analysis revealed a major division between the tonsil B cell samples and plasma cell samples with the exception of one tonsil plasma cell sample being clustered with tonsil B cell. The normal plasma cells were further subdivided into two distinct groups of tonsil plasma cells and bone marrow plasma cells. Thus, global gene expression patterns confirmed the segregation of tonsil plasma cells and bone marrow plasma cells and also allowed the distinction of tonsil B cells from both plasma cell types.

$\chi^2$ and Wilcoxon rank sum analysis were used to identify 359 and 500 genes whose mRNA expression levels were significantly altered (P<0.00005) in the tonsil B cell to tonsil plasma cell and tonsil plasma cell to bone marrow plasma cell comparison, respectively. Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs).

Early Differentiation Genes

Of the top 50 EDGs (Table 11), most of the genes (43) were down-regulated with only 7 genes being up-regulated in this transition. Gene expression was described as being at 1 of 5 possible levels. An AAC, indicating an undetectable or absent gene transcript, was defined as "−". For all the samples in a group, expression levels were defined as "+" if the gene transcript was present and the AD was <1000, "++" for 1000≦AD<5000, "+++" for 5000≦AD<10,000, and "++++" for AD≧10,000. The largest group of EDGs encoded transcription factors. Of 16 transcription factors, only 3, XBP-1, IRF4 and BMI1, were up-regulated EDGs. Among the down-regulated transcription factors, MYC and CIITA were found. The largest family included four ets domain-containing proteins: ETS1, SPIB, SPI1, and ELF1. Other transcription factors included the repressors EED and ID3, as well as the activators RUNX3, ICSBP1, REL, ERG3, and FOXM1. It is of potential significance that as IRF4 is up-regulated in both the tonsil B cell to tonsil plasma cell and tonsil plasma cell to bone marrow plasma cell transitions, the IRF family member interferon consensus sequence binding protein, ICSBP1, which is a lymphoid-specific negative regulator, was the only gene that was expressed at a +++ level in tonsil B cells and was shut down in both tonsil plasma cells and bone marrow plasma cells. These results suggest that the removal of ICSBP1 from IRF binding sites may be an important mechanism in regulating IRF4 function.

The second most abundant class of EDGs code for proteins involved in signaling. CASP10 which is involved in the activation cascade of caspases responsible for apoptosis execution represented the only signaling protein up-regulated in tonsil plasma cells. Three small G proteins, the Rho family members ARHG and ARHH, and the proto-oncogene HRAS were down-regulated EDGs. Two members of the tumor necrosis factor family TNF and lymphotoxin beta (LTB), as well as the TNF receptor binding protein were LDGs. Given the important role of IL-4 in triggering class-switch recombination, the observation of down-regulation (tonsil B cell to tonsil plasma cell), and eventual extinguishing (tonsil plasma cell to bone marrow plasma cell) of IL4R fits well with the differentiation states of the cells under study.

Finally, the down-regulation of the B lymphoid tyrosine kinase (BLK) whose expression is restricted to B lymphoid cells and may function in a signal transduction pathway suggests that the reduction of this kinase is important in the early stages of plasma cell differentiation. Given the important role of cell adhesion in plasma cell biology, up-regulation of ITGA6 and PECAM1 could be of particular importance. In fact, these genes also showed a continual up-regulation in the tonsil plasma cell to bone marrow plasma cell transition and represented the only extracellular adhesion genes in the EDG class. Other multiple-member classes of down-regulated EDGs included those involved in cell cycle (CCNF, CCNG2, and CDC20) or DNA repair/maintenance (TERF2, LIG1, MSH2, RPA1). The down-regulation of these genes may thus be important to inducing and/or maintaining the terminal differentiated state of the plasma cells.

Late Differentiation Genes

In the top 50 LDGs, 33 were up-regulated or turned on and 17 genes were down-regulated or turned off (Table 12). Although 16 EDGs were transcription factors, only 5 LDGs belonged to this class. The BMI1 gene, which was an up-regulated EDG, was also an LDG, indicating that the gene undergoes a significant increase in expression in both the tonsil B cell to tonsil plasma cell and tonsil plasma cell to bone marrow plasma cell transitions. BMI1 was the only up-regulated transcription factor. MYBL1, MEF2B, and BCL6 were shut down in bone marrow plasma cells and the transcription elongation factor TCEA1 was down-regulated. The largest class of L)G (n=16; 11 up- and 5 down-regulated) coded for proteins involved in signaling. The LIM containing protein with both nuclear and focal adhesion localization, FHL1; and the secreted proteins, JAG1, a ligand for Notch, insulin-like growth factor IGF1; and bone morphogenic protein BMP6 were up-regulated. The dual specific phosphatase DUSP5 and the chemokine receptor CCR2 represented genes with the most dramatically altered expression and were turned on to extremely high levels in bone marrow plasma cells while being absent in tonsil plasma cells. Additional signaling genes, including the membrane caveoloe, CAV1 and CAV2, plasma membrane proteins important in transportation of materials and organizing numerous signal transduction pathways, were up-regulated LDGs.

Given the dramatic difference in life spans of tonsil plasma cells (several days) and bone marrow plasma cells (several weeks to months), the up-regulation of the anti-apoptotic gene BCL2 (− in tonsil B cells and ++ in bone marrow plasma cells) and concomitant down-regulation of the apoptosis-inducing protein BIK (+++ in tonsil B cells and − in bone marrow plasma cells) may be critical in regulating normal programmed cell death. As in the EDGs, LDGs contained multiple adhesion-related genes, and, as in the EDGs, the LDG adhesion genes were all up-regulated.

The PECAM1 gene was found to be both an EDG and LDG, suggesting that a gradation of cell surface expression of this gene is critical in development. Whereas the integrin family member ITGA6 was an EDG, ITGA4 was found to be an LDG. The finding that ITGA4 or VLA-4 (very late antigen 4) was an LDG is consistent with published data showing that this integrin is most predominant on late stage plasma cells. The adhesion molecule selectin P ligand (SELPLG) which mediates high affinity, calcium-dependent binding to P-, E- and L-selectins, mediating the tethering and rolling of neutrophils and T lymphocytes on endothelial cells, may facilitate a similar mechanism in late stage plasma cells. In addition, the epithelial membrane protein 3 (EMP3), a integral membrane glycoprotein putatively involved in cell-cell interactions, was identified. LRMP (JAW1), a lymphoid-restricted, integral ER membrane protein based on strong homology to MRVI1 (IRAG) and is likely a essential nitric oxide/cGKI-dependent regulator of IP3-induced calcium release from endoplasmic reticulum stores, was found to be a down-regulated LDG. The discovery of LRMP as a down-regulated LDG is consistent with previous studies showing that, although highly expressed in lymphoid precursors, it is shut down in plasma cells.

Thus, the gene expression profiling results confirmed previous observations as well as identified novel and highly significant changes in mRNA synthesis when tonsil B cells and tonsil plasma cells and tonsil plasma cells and bone marrow plasma cells are compared.

TABLE 11

Early-Stage Differentiation Genes: Top 50 Differentially Expressed Genes In Comparison Of Tonsil B Cells And Tonsil And Bone Marrow Plasma Cells

| Accession | Symbol | Function | TBC | TPC | BPC |
|---|---|---|---|---|---|
| U60519 | CASP10 | apoptosis | − | + | ++ |
| X53586 | ITGA6 | adhesion | − | + | ++ |
| U04735 | STCH | chaperone | + | ++ | ++ |
| L13689 | BMI1 | transcription; repressor; PcG | + | ++ | +++ |
| L34657 | PECAM1 | adhesion | + | ++ | +++ |
| U52682 | IRF4 | transcription; IRF family | + | +++ | +++ |
| M31627 | XBP1 | transcription; bZip family | +++ | ++++ | ++++ |
| AB000410 | OGG1 | DNA glycosylase | + | − | − |
| D87432 | SLC7A6 | solute transporter | + | − | − |
| J04101 | ETS1 | transcription; ets family | + | − | − |
| L38820 | CD1D | immunity | + | − | − |
| M28827 | CD1C | immunity | + | − | − |
| M55542 | GBP1 | signaling; GTP binding | + | − | − |
| M81182 | ABCD3 | ABC transporter | + | − | − |
| M85085 | CSTF2 | mRNA cleavage stimulating factor | + | − | − |
| U74612 | FOXM1 | transcription; fork-head family | + | − | − |
| U84720 | RAE1 | RNA export | + | − | − |
| V00574 | HRAS | signaling; GTP binding protein | + | − | − |
| X02910 | TNF | signaling; TNF__ | + | − | − |
| X63741 | EGR3 | transcription; egr family | + | − | − |
| X93512 | TERF2 | telomere repeat binding protein | + | − | − |
| Z36714 | CCNF | cell cycle; cyclin F | + | − | − |
| AB000409 | MNK1 | signaling; kinase | + | − | + |
| M33308 | VCL | cytoskeleton | + | − | ++ |
| D16480 | HADHA | mitochondrial oxidation | ++ | − | − |
| M63488 | RPA1 | DNA replication/repair | ++ | − | − |
| U03911 | MSH2 | DNA repair | ++ | − | − |
| U69108 | TRAF5 | signaling; TNFR associated protein | ++ | − | − |
| X12517 | SNRPC | mRNA splicing | ++ | − | − |
| X52056 | SPI1 | transcription; ets family | ++ | − | − |
| X68149 | BLR1 | signaling; cxc receptor | ++ | − | − |
| X74301 | CIITA | transcription; adaptor | ++ | − | − |
| X75042 | REL | transcription; rel/dorsal family | ++ | − | − |
| L00058 | MYC | transcription; bHLHZip | ++ | − | ++ |
| M36067 | LIG1 | DNA ligase | ++ | + | + |
| M82882 | ELF1 | transcription; ets family | ++ | + | + |
| S76617 | BLK | signaling; kinase | ++ | + | + |
| U47414 | CCNG2 | cell cycle; cyclin G | ++ | + | + |
| U61167 | SH3D1B | unknown; SH3 containing protein | ++ | + | + |
| X61587 | ARHG | signaling; Rho G | ++ | + | + |
| Z35278 | RUNX3 | transcription; contains runt domain | ++ | + | + |
| M91196 | ICSBP1 | transcription; IRF family | +++ | − | − |
| M34458 | LMNB1 | cytoskeletal matrix | +++ | + | − |
| U90651 | EED | transcription; repression; PcG | +++ | + | − |
| X69111 | ID3 | transcription; repression; bHLH | +++ | + | + |
| X52425 | IL4R | signaling; cytokine receptor | +++ | ++ | − |
| Z35227 | ARHH | signaling; Rho H | +++ | ++ | + |
| U89922 | LTB | signaling; TNF-c | ++++ | + | + |
| U05340 | CDC20 | cell cycle; activator of APC | ++++ | ++ | − |
| X66079 | SPIB | transcription; ets family | ++++ | ++ | − |

Accession = GENBANK ® accession number. Symbol = HUGO approved gene symbol. TBC, tonsil B cell; TPC, tonsil plasma cell; BPC, bone marrow plasma cell; AD, mean average difference; AC, absolute call. Quantitative gene expression: −, AC absent; +, AC present and AD < 1,000; ++, AD = 1,000 to 5,000; +++, AD = 5,000 to 10,000; ++++, AD > 10,000.

TABLE 12

Late-Stage Differentiation Genes: Top 50 Differentially Expressed Genes In Comparison Of Tonsil And Bone Marrow Plasma Cells

| Accession | Symbol | Function | TPC | BPC |
|---|---|---|---|---|
| U32114 | CAV2 | signaling; membrane caveolae | − | + |
| U60115 | FHL1 | signaling; LIM domain | − | + |
| U73936 | JAG1 | signaling; Notch ligand | − | + |
| X57025 | IGF1 | signaling; growth factor | − | + |
| Z32684 | XK | membrane transport | − | + |
| D10511 | ACAT1 | metabolism; ketone | − | ++ |
| Y08999 | ARPC1A | actin polymerization | − | ++ |
| M14745 | BCL2 | signaling; anti-apoptosis | − | ++ |
| M24486 | P4HA1 | collagen synthesis | − | ++ |
| M60315 | BMP6 | signaling; TGF family | − | ++ |
| U25956 | SELPLG | adhesion | − | ++ |
| X16983 | ITGA4 | adhesion | − | ++ |
| Z18951 | CAV1 | signaling; membrane caveolae | − | ++ |
| M60092 | AMPD1 | metabolism; energy | − | +++ |
| U15932 | DUSP5 | signaling; phosphatase | − | ++++ |
| U95626 | CCR2 | signaling; chemokine receptor | − | ++++ |
| D78132 | RHEB2 | signaling; ras homolog | + | ++ |
| L41887 | SFRS7 | mRNA splicing factor | + | ++ |
| M23161 | LOC90411[a] | unknown | + | ++ |
| M37721 | PAM | metabolism; hormone amidation | + | ++ |
| M69023 | TSPAN-3[a] | unknown | + | ++ |
| U02556 | TCTE1L | dynein homolog | + | ++ |
| U41060 | LIV-1[a] | unknown | + | ++ |
| U44772 | PPT1 | lysosome enzyme | + | ++ |
| U70660 | ATOX1 | metabolism; antioxidant | + | ++ |
| X92493 | PIP5K1B | signaling; kinase | + | ++ |
| M23254 | CAPN2 | cysteine protease | + | +++ |
| J02763 | S100A6 | signaling; calcium binding | ++ | +++ |
| L13689 | BMI1 | transcription; repressor; PcG | ++ | +++ |
| L34657 | PECAM1 | adhesion | ++ | +++ |
| M23294 | HEXB | metabolism; hexoaminidase | ++ | +++ |
| M64098 | HLDBP | metabolism; sterol | ++ | ++++ |

TABLE 12-continued

Late-Stage Differentiation Genes: Top 50 Differentially Expressed Genes In Comparison Of Tonsil And Bone Marrow Plasma Cells

| Accession | Symbol | Function | Quantitative Gene Expression | |
|---|---|---|---|---|
| | | | TPC | BPC |
| U52101 | EMP3 | adhesion | ++ | ++++ |
| X66087 | MYBL1 | transcription; myb-like | + | − |
| X54942 | CKS2 | cell cycle; kinase regulator | ++ | − |
| X73568 | SYK | signaling; kinase | ++ | − |
| L08177 | EBI2 | signaling; receptor | ++ | − |
| M25629 | KLK1 | protease; serine | ++ | − |
| U00115 | BCL6 | transcription; Zn-finger | ++ | − |
| U23852 | LCK | signaling; kinase | ++ | − |
| U60975 | SORL1 | endocytosis | ++ | − |
| X63380 | MEF2B | transcription; MADs box | ++ | − |
| L25878 | EPXH1 | metabolism; epoxide hydrolase | ++ | + |
| Z35227 | ARHH | signaling; Rho C | ++ | + |
| X89986 | BIK | signaling; apoptosis | +++ | − |
| M13792 | ADA | metabolism; purine | +++ | + |
| U10485 | LRMP | ER membrane protein | +++ | + |
| M81601 | TCEA1 | transcription; elongation | +++ | ++ |
| X70326 | MACMARCK | actin binding | ++++ | + |
| X56494 | PKM2 | metabolism; energy | ++++ | + |

Accession = GENBANK ® accession number.
Symbol = HUGO approved gene symbol.
<sup>a</sup>Unapproved symbol.
TPC, tonsil plasma cell;
BPC, bone marrow plasma cell;
AD, mean average difference;
AC, absolute call.
Quantitative gene expression:
−, AC absent;
+, AC present and AD < 1,000;
++, AD = 1,000 to 5,000;
+++, AD = 5,000 to 10,000;
++++, AD > 10,000.

EXAMPLE 15

Previously Identified and Novel Genes in Plasma Cell Differentiation

In this gene expression profiling study, not only previously identified but also novel genes associated with plasma cell development were identified. Some of the genes that may be pertinent to plasma cell differentiation are discussed here.

Polyadenylation of mRNA is a complex process that requires multiple protein factors, including 3 cleavage stimulation factors (CSTF1, CSFT2 and CSTF3). It has been shown that the concentration of CSTF2 increases during B cell activation, and this is sufficient to switch IgM heavy chain mRNA expression from membrane-bound form to secreted form. The CSTF2 gene was expressed at low levels in tonsil B cells, but was turned off in tonsil and bone marrow plasma cells, indicating that CSTF2 gene expression can also be used to define plasma cell differentiation.

The gene for CD63 showed a progressive increase in gene expression across the three cell types studied. CD63 belongs to the transmembrane 4 super family (TM4SF) of membrane proteins. Expression has been found on the intracellular lysosomal membranes of hemopoietic precursors in bone marrow, macrophages, platelets, and Wiebel-Palade bodies of vascular endothelium. Importantly, CD63 was described as a maker for melanoma progression and regulates tumor cell motility, adhesion, and migration on substrates associated with β1 integrins.

Most importantly, the discovery of novel genes reported herein will lead to a broader knowledge of the molecular mechanisms involved in plasma cell differentiation. Specifically, of the top 50 EDGs, most were down-regulated, and a majority of the EDGs were transcription factors, suggesting that transcriptional regulation is a n important mechanism for modulating differentiation. Among the LDGs, transcription factor representation was much lower than among the EDGs.

Cell Cycle Control and Programmed Cell Death

Consistent with the terminal differentiation of plasma cells, many genes involved in cell cycle control and DNA metabolism were down-regulated EDGs. The modulation of DNA ligase LIG1; repair enzymes MSHC, and RPA1, CDC20; and the cyclins CCNG2 and CCNF may have important consequences in inducing the quiescent state of plasma cells. The telomeric repeat binding protein TERF2, which is one of two recently cloned mammalian telomere binding protein genes, was a down-regulated EDG. TERF2 acts to protect telomer ends, prevents telomere end-to-end fusion, and may be important in maintaining genomic stability. It is of interest to determine if TERF2 is down-regulated during the terminal differentiation of all cell types, and whether the lack of this gene product in tumors of terminally differentiated cells results in the high degree of chromosome structural rearrangements which is a hallmark of multiple myeloma that lacks TERF2 gene expression (unpublished data).

The CDC28 protein kinase 2 gene CKS2, which binds to the catalytic subunit of the cyclin dependent kinases and is essential for their biological function, was the only cell cycle gene in the LDG genes. It was expressed in tonsil plasma cells that are capable of modest proliferation; however, CKS2 was completely extinguished in bone marrow plasma cells. Thus, shutting down CKS2 expression may be critical in ending the proliferative capacity of bone marrow plasma cells.

A distinguishing feature of plasma cell terminal differentiation is the acquisition of increased longevity in the bone marrow plasma cells. It is likely that this phenomenon is controlled through programmed cell death or apoptosis. The finding that anti-apoptotic and pro-apoptotic genes, BCL2 and BIK, demonstrated opposing shifts in expression is consistent with these two genes playing major roles in extending the life-span of bone marrow plasma cells.

Transcription Factors

The majority of differentially expressed genes belong to the transcription factor family. Of the 50 EDGs, only 7 were up-regulated. IRF4 and XBP1, two genes known to be up-regulated during plasma cell differentiation were in this group. Both genes were expressed at equal levels in the tonsil and bone marrow plasma cells, suggesting that a continual increase in expression of these important regulators does not occur. Although not on the HuGenFL Microarray, recent studies using third generation AffymetrixU95Av2 microarray have also revealed an induction of Blimp-1 (PRDM1) expression in plasma cells compared with tonsil B cells (unpublished data), confirming the expected patterns of these transcription factors.

The vast majority of EDGs were down-regulated and the single largest subgroup of EDGs represented transcription factors (13 of 43 genes). Four of the 13 transcription factors, ETS1, SPI1, SP1B, and ELF1, belong to the ets family. These results are consistent with previous studies showing that several of the ETS proteins (ETS1, ELF1, PU.1 (SPI1), and SPI-B) are expressed in the B cell lineage. It is interesting to note that the down-regulation of ETS1 in the transition between tonsil B cell to tonsil plasma cell may be an important switch, as ETS1 knock-out mice show dramatic increases in plasma cells in the spleen and peripheral blood. In addition, it is curious that although SPI1 (PU.1) interacts with IRF4 in Blimp-1+ germinal center tonsil B cells and plasma cells, data presented herein show that whereas IRF4 is up-regulated in the plasma cell transition, SPI1 is shut down in tonsil and bone marrow plasma cells. Thus, these data support the notion that the ets family of transcription factors are important hematopoietically and that down-regulation of at least four family members appears to be an important event in terminal differentiation of plasma cells.

The cytoskeletal gene vinculin (VCL) and the MAP kinase-interacting serine/threonine kinase 1 gene (MKNK1) represented novel EDGs. Vinculin is thought to function in anchoring F-actin to the membrane, whereas MKNK1 is an ERK substrate that phosphorylates eIF4e after recruitment to the eIF4F complex by binding to eIF4G. These two genes were turned off in the tonsil B cell to tonsil plasma cell transition, but were reactivated in bone marrow plasma cells. The MYC proto-oncogene also showed a dramatic down-regulation in the tonsil B cell to tonsil plasma cell transition with reactivation in bone marrow plasma cells. It will be important to understand if these two genes are regulated either directly or indirectly by MYC. One of the mechanisms by which PRDF1-BF1 promotes generation of plasma cells is repression of MYC, thereby allowing the B cells to exit the cell cycle and undergo terminal differentiation. Instant study showing the extinguishing of MYC in the tonsil B cell to tonsil plasma cell transition is consistent with this data. The reactivation of MYC in bone marrow plasma cells to levels similar to those seen in tonsil B cells, which appear to be highly proliferative blasts, is unresolved but suggests that MYC may have dual roles.

Similar to the tonsil B cell to tonsil plasma cell transition, the majority of the transcription factors were down-regulated in the tonsil to bone marrow plasma cell transition. The BCL6 gene, although not in the top 50 significant EDGs, did make the top 50 list for LDGs. BCL6 did show a progressive loss of expression from tonsil B cells to tonsil plasma cells (see Table 10), but there was then a dramatic loss of expression in bone marrow plasma cells. Additional transcription factors, the myb-like gene MYBL1, and the MADS box factor MEF2B, were also turned off in bone marrow plasma cells and may be major regulators of the terminal stages of plasma cell differentiation. The transcription elongation factor TCEA1 was down-regulated but remained present. BMI1, a member of a vertebrate Polycomb complex that regulates segmental identity by repressing HOX genes throughout development, showed a significant progressive increase in expression across all groups. It is of note that BMI1 is the human homolog of the mouse Bmi-1 proto-oncogene originally discovered as cooperating with transgenic c-Myc in inducing B cell lymphomas.

Given the recognition that changes in levels of expression of transcription factors represent the most striking feature of plasma cell differentiation, it is of interest to elucidate distinct pathways of transcriptional regulation driven by the various classes of transcription factors discovered herein. This can be done with the aid of global expression profiling and sophisticated data mining tools such as Baysian networks.

EXAMPLE 16

Identification of Genes with Similar Expression Between Multiple Myeloma and Cells at Different Stages of B Cell Development Examples 16 and 17 describe the establishment of a B cell developmental stage-based classification of multiple myeloma using global gene expression profiling.

To classify multiple myeloma with respect to EDG and LDG reported above, 74 newly diagnosed cases of multiple myeloma and 7 tonsil B cell, 7 tonsil plasma cell, and 7 bone marrow plasma cell samples were tested for variance across the 359 EDGs and 500 LDGs disclosed above. The top 50 EDGs that showed the most significant variance across all samples were defined as early differentiation genes for myeloma (EDG-MM); likewise, the top 50 LDGs showing the most significant variance across all samples were identified as late differentiation genes for myeloma-1 (LDG-MM1). Subtracting the LDG-MM1 from the 500 LDG and then applying one-way ANOVA test for variance to the remaining genes identified the top 50 genes showing similarities between bone marrow plasma cells and multiple myeloma. These genes were defined as LDG-MM2.

Within the top 50 EDG-MM (Table 13), 18 genes that showed up-regulation in the tonsil B cell to tonsil plasma cell transition showed down-regulation to levels at or below that seen in tonsil B cells. The remaining 32 EDG-MM showed a reverse profile, in that these genes were down-regulated in the tonsil B cell to plasma cell transition, but showed tonsil B cell-like expression in multiple myeloma. In Table 13, gene expression was described as being at 1 of 5 possible levels. An absent absolute call (AAC), indicating an undetectable or absent gene transcript, was defined as "−". For all the samples in a group, expression levels were defined as "+" if the gene transcript was present and the average difference (AD) was <1000, "++" for $0.1000 \leq AD < 5000$, "+++" for $5000 \leq AD < 10,000$, and "++++" for $AD \geq 10,000$.

One of the most striking genes defining EDG-MM was the cyclin dependent kinase 8 (CDK8), which was found absent in tonsil B cells but up-regulated to extremely high levels in tonsil and bone marrow plasma cells and then shut down again in virtually all multiple myeloma cases. The mitotic cyclin showed a progressive loss in expression from tonsil B cell (++) to tonsil plasma cell (+) to bone marrow plasma cell (−), whereas multiple myeloma cases either showing bone marrow-like levels or tonsil B cell levels. Given that the tonsil B cells used in this study likely represent highly proliferative centroblasts, multiple myeloma cases with similar levels might b e suggestive of a proliferative form of the disease. A total of 27 of the top 50 EDG-MM showed no variability in multiple myeloma, ie, all multiple myeloma and tonsil B cell samples showed similar levels of expression.

A majority (34 of 50) of the top 50 LDG-MM1 (Table 14) were genes that showed up-regulation from the transition of tonsil plasma cell to bone marrow plasma cell, but showed down-regulation to tonsil plasma cell levels in multiple myeloma. The overall pattern seen for LDG-MM1 was the reverse seen for the EDG-MM, where a majority of those genes showed down-regulation from tonsil B cell to plasma cell and up regulation to tonsil B cell-like levels in multiple myeloma. The most dramatically altered LDG-MM1 was seen in the massive up-regulation of the cxc chemokines SDF1, PF4, and PPBP in bone marrow plasma cells in contrast with complete absence of detectable transcripts in all multiple myeloma. These results are validated by the fact that two separate and distinct probe sets interrogating different region of SDF1 (accession numbers L36033 and U19495) were found to show identical patterns. The RB1 tumor suppressor gene showed a significant up-regulation in the tonsil plasma cell (+) to bone marrow plasma cell (++) transition with multiple myeloma showing levels consistent with either cell type. Unlike with the EDG-MM, only 15 of the top 50 LDG-MM1 showed no variability within the multiple myeloma population.

The LDG-MM2 genes (Table 15) showing similarities between bone marrow plasma cells and subsets of multiple myeloma revealed that all genes showed variability within multiple myeloma and that the variability could be dramatic, e.g. the apoptosis inhibitor BIK. Unlike those seen in EDG-MM and LDG-MM1, a large class of LDG-MM2 represented genes coding for enzymes involved in metabolism with a majority involved in glucose metabolism.

TABLE 13

EDG-MM: Tonsil B Cell-like Multiple Myeloma Genes

| | | | Quantitative Gene Expression | | | |
|---|---|---|---|---|---|---|
| Accession | Symbol | Function | TBC | TPC | BPC | MM |
| D28364 | ANXA2 | annexin family | − | + | + | −/+ |
| U81787 | WNT10B | signaling; ligand | − | + | ++ | −/++ |
| U88898 | LOC51581[a] | unknown | − | + | + | −/+ |
| X12451 | CTSL | protease; cysteine | − | ++ | ++ | − |
| Z25347 | CDK8 | cell cycle; kinase | − | ++++ | ++++ | −/++ |
| D38548 | KIAA0076[a] | unknown | + | ++ | ++ | +/++ |
| D86479 | AEBP1 | extracellular matrix | + | ++ | ++ | + |
| U04689 | OR1D2 | signaling; receptor | + | ++ | + | + |
| M31328 | GNB3 | signaling; G protein | + | ++ | ++ | + |
| U13395 | WWOX | metabolism; oxidoreductase | + | ++ | ++ | + |
| X14675 | BCR | signaling; GTPase for RAC | + | ++ | ++ | + |
| X16665 | HOXB2 | transcription; homeobox domain | + | ++ | ++ | −/+ |
| Z11899 | POU5F1 | transcription; homeobox domain | + | ++ | ++ | + |
| Z36531 | FGL2 | secreted fibrinogen-like | + | ++ | ++ | + |
| X80907 | PIK3R2 | signaling; kinase adaptor | + | +++ | +++ | ++ |
| D31846 | AQP2 | aquaporin | ++ | +++ | +++ | ++ |
| L18983 | PTPRN | phosphatase; membra | ++ | ++++ | ++++ | ++ |
| M23323 | CD3E | signaling; TCR partner | ++ | ++++ | ++++ | ++ |
| D83781 | KIAA0197[a] | unknown | + | − | − | + |
| HT4824 | CBS | metabolism; cystathionine-beta-synthase | + | − | − | −/++ |
| S78873 | RABIF | signaling; GTP releasing factor | + | − | − | +/++ |
| U32645 | ELF4 | transcription; ets domian | + | − | − | −/+ |
| X97630 | EMK1 | signaling; kinase; ELK domain | + | − | − | + |
| Z24724 | UNKNOWN[a] | cell cycle | + | − | − | +/++ |
| D16480 | HADHA | mitochondrial oxidation | ++ | − | − | −/++ |
| L77701 | COX17 | mitochondrial oxidation | ++ | − | − | −/++ |
| M90356 | BTF3L2 | transcription; NAC doi | ++ | − | − | ++ |
| U08815 | SF3A3 | spliceosome | ++ | − | − | +/++ |
| U53225 | SNX1 | Intracellular trafficking | ++ | − | − | +/++ |
| M25753 | CCNB1 | cell cycle | ++ | + | − | −/++ |
| D87448 | TOPBP1[a] | topoisomerase II bind protein | ++ | + | + | −/++ |
| L38810 | PSMC5 | 26S proteasome subunit 5 | ++ | + | + | ++ |
| M29551 | PPP3CB | signaling; calcium dep phosphatase | ++ | + | + | +/++ |
| M32886 | SRI | signaling; calcium binding | ++ | + | + | ++ |
| U24704 | PSMD4 | 26S proteasome subunit 4 | ++ | + | + | ++ |
| U25165 | FXR1 | RNA binding protein | ++ | + | + | ++ |
| U37022 | CDK4 | cell cycle; kinase | ++ | + | + | ++ |

TABLE 13-continued

EDG-MM: Tonsil B Cell-like Multiple Myeloma Genes

| Accession | Symbol | Function | Quantitative Gene Expression | | | |
|---|---|---|---|---|---|---|
| | | | TBC | TPC | BPC | MM |
| U53003 | C21orf33 | unknown; highly conserved | ++ | + | + | ++ |
| X89985 | BCL7B | actin crosslinking | ++ | + | + | ++ |
| D49738 | CKAP1 | tubulin folding | +++ | + | + | ++ |
| D43950 | CCT5 | chaperonin | +++ | ++ | ++ | +++ |
| D82348 | ATIC | metabolism; purine biosynthesis | +++ | ++ | ++ | +++ |
| D86550 | DYRK1A | signaling; kinase | +++ | ++ | ++ | +++ |
| L06132 | VDAC1 | anion channel | +++ | ++ | ++ | ++/+++ |
| L43631 | SAFB | nuclear scaffold factor | +++ | ++ | ++ | ++/+++ |
| M30448 | CSNK2B | signaling; casein kinas regulation | +++ | ++ | ++ | |
| X76013 | QARS | metabolism; glutaminyl tRNA synthetase | +++ | ++ | ++ | ++/+++ |
| D83735 | CNN2 | actin binding | ++++ | ++ | ++ | ++/++++ |
| M86667 | NAP1L1 | nucleosome assembly | ++++ | ++ | ++ | +++ |
| X04828 | GNAI2 | signaling; G protein | ++++ | ++ | ++ | ++/+++ |

Genes identified by one-way ANOVA analysis. Accession = GENBANK® accession number. Symbol = HUGO approved gene symbol; unapproved symbol marked by $^a$. TBC, tonsil B cells; TPC, tonsil plasma cells; BPC, bone marrow plasma cells; AC, absolute call; AD, average difference. Quantitative gene expression: −, AC absent; +, AC present and AD < 1,000; ++, AD = 1,000 to 5,000; +++, AD = 5,000 to 10,000; ++++, AD > 10,000.

TABLE 14

LDG-MM1: Tonsil Plasma Cell-Like Multiple Myeloma Genes

| Accession | Symbol | Function | Quantitative Gene Expression | | |
|---|---|---|---|---|---|
| | | | TPC | BPC | MM |
| U90902 | 23612[a] | unknown; related to TIAM1 | − | + | −/++ |
| D12775 | AMPD3 | metabolism; AMP deaminase | − | + | −/++ |
| U37546 | BIRC3 | signaling; anti-apoptosis | − | ++ | −/++ |
| Z11793 | SEPP1 | metabolism; selenium transport | − | +++ | −/+ |
| L36033 | SDF1 | signaling; cxc chemokine | − | +++ | − |
| U19495 | SDF1 | signaling; cxc chemokine | − | +++ | − |
| M27891 | CST3 | protease inhibitor | − | ++++ | −/++++ |
| M26602 | DEFA1 | immunity | − | ++++ | −/++++ |
| M25897 | PF4 | signaling; cxc chemokine | − | ++++ | − |
| M54995 | PPBP | signaling; cxc chemokine | − | ++++ | − |
| U79288 | KIAA0513[a] | unknown | + | ++ | +/++ |
| M59465 | TNFAIP1 | signaling; anti-apoptosis | + | ++ | +/++++ |
| X53586 | ITGA6 | adhesion | + | ++ | +/++ |
| D50663 | TCTEL1 | dynein light chain | + | ++ | +/++ |
| U40846 | NAGLU | metabolism; hepran sulfate degradation | + | ++ | +/++ |
| M80563 | S100A4 | Signaling; calcium binding | + | ++ | +/++++ |
| X04085 | CAT | metabolism; catalase | + | ++ | +/++ |
| L02648 | TCN2 | metabolism; vitamin B12 transport | + | ++ | + |
| L35249 | ATP6B2 | lysosome; vacuolar proton pump | + | ++ | + |
| L09209 | APLP2 | amyloid beta precursor like | + | ++ | + |
| L41870 | RB1 | cell cycle | + | ++ | +/++ |
| X76732 | NUCB2 | signaling; calcium binding | + | +++ | +/+++ |
| D29805 | 5B4GALT1 | adhesion | + | +++ | + |
| M29877 | FUCA1 | lysosome; fucosidase | + | +++ | +/++ |
| M32304 | TIMP2 | metalloproteinase 2 inhibitor | + | +++ | +/++++ |
| D10522 | MACS | actin crosslinking | + | ++++ | −/++ |
| L38696 | RALY[a] | RNA binding | ++ | +++ | ++ |
| U05875 | IFNGR2 | signaling; interferon gamma receptor | ++ | +++ | ++/+++ |
| U78095 | SPINT2 | protease inhibitor; blocks HGF | ++ | +++ | −/+++ |
| L13977 | PRCP | lysosomal; angiotensinase C | ++ | ++++ | ++ |

TABLE 14-continued

LDG-MM1: Tonsil Plasma Cell-Like Multiple Myeloma Genes

| Accession | Symbol | Function | Quantitative Gene Expression | | |
|---|---|---|---|---|---|
| | | | TPC | BPC | MM |
| U12255 | FCGRT | IgG Fc receptor | ++ | ++++ | −/+++ |
| L06797 | CXCR4 | signaling; SDF1 receptor | ++ | ++++ | ++/++++ |
| D82061 | FABGL | metabolism | ++ | ++++ | ++/+++ |
| Y00433 | GPX1 | oxidation protection | +++ | − | ++/+++ |
| M60752 | H2AFA | histone; nucleosome | + | − | −/++ |
| U18300 | DDB2 | DNA repair | + | − | + |
| X63692 | DNMT1 | DNA methyltransferase | + | − | + |
| D11327 | PTPN7 | signaling; phosphatase | ++ | − | ++ |
| X54942 | CKS2 | cell cycle; kinase regulator | ++ | − | +/+++ |
| D14874 | ADM | adrenomedullin | ++ | + | +/++++ |
| D86976 | KIAA0223[a] | minor histocompatability antigen | ++ | + | +/+++ |
| X52979 | SNRPB | mRNA splicing | ++ | + | +/++ |
| Z49254 | MRPL23 | mitochondrial ribosomal protein | ++ | + | ++ |
| U66464 | HPK1 | signaling; kinase | ++ | + | +/++ |
| U91903 | FRZB | signaling; WNT antagonists | ++ | + | +/++ |
| D87453 | MRPS27 | mitochondrial ribosomal protein | ++ | + | +/++ |
| X59932 | CSK | signaling; kinase | +++ | ++ | ++ |
| L17131 | HMGIY | transcription; high mobility group | ++++ | + | ++/++++ |
| L19779 | H2AFO | histone; nucleosome | ++++ | ++ | ++++ |
| U70439 | SSP29[a] | unknown | ++++ | +++ | +++/++++ |

Genes identified by one-way ANOVA analysis. Accession = GENBANK ® accession number. Symbol = HUGO approved gene symbol; unapproved symbol marked by [a]. TPC, tonsil plasma cells; BPC, bone marrow plasma cells; AC, absolute call; AD, average difference. Quantitative gene expression: −, AC absent; +, AC present and AD < 1,000; ++, AD = 1,000 to 5,000; +++, AD = 5,000 to 10,000; ++++, AD > 10,000.

TABLE 15

LDG-MM2: Bone marrow Plasma Cell-like Multiple Myeloma Genes

| Accession | Symbol | Function | Quantitative Gene Expression | |
|---|---|---|---|---|
| | | | BPC | MM |
| U61145 | EZH2 | transcription; SET domain | − | −/+ |
| HT4000 | SYK | signaling; lymphocyte kinase | − | −/++ |
| X89986 | BIK | signaling; apoptosis inducer | − | −/++++ |
| D85181 | SC5DL | metabolism; sterol-C5-desaturase | + | −/+ |
| M98045 | FPGS | metabolism; folylpolyglutamate synthase | + | −/++ |
| L41559 | PCBD | transcription; enhances TCF1 activity | + | −/++ |
| L25876 | CDKN2 | cell cycle; CDK inhibitor; phosphatase | + | +/++ |
| U76638 | BRAD1 | transcription; BRCA1 heterodimer | + | +/++ |
| L05072 | IRF1 | transcription; IRF family | + | +/++ |
| D87440 | KIAA025[a] | unknown | + | +/++ |
| U02680 | PTK9 | tyrosine kinase | + | +/++ |
| U28042 | DDX10 | oncogene; ATP-dependent RNA helicase | + | +/++ |
| L20320 | CDK7 | cell cycle; kinase | + | +/++ |
| X56494 | PKM2 | metabolism; pyruvate kinase | + | +/++++ |
| M12959 | TCRA | signaling; T cell receptor | ++ | −/++ |
| HT3981 | INSL3 | signaling; insulin-like peptide; IGF family | ++ | −/++ |
| U21931 | FBP1 | metabolism; fructose bisphophatase | ++ | −/++++ |
| Z48054 | PXR1 | metabolism; peroxisome biogenesis | ++ | +/++ |
| D84145 | WS-3[a] | dynatin 6 | ++ | +/++ |
| D14661 | KIAA0105[a] | transcription; WT1-associating protein | ++ | +/++ |
| X77548 | NCOA4 | transcription; nuclear receptor coactivator | ++ | +/++ |
| M90696 | CTSS | cysteine protease | ++ | +/++ |
| D11086 | IL2RG | cytokine receptor | ++ | +/++ |
| U70426 | RGS16 | signaling; GTPase activating protein | ++ | +/+++ |

TABLE 15-continued

LDG-MM2: Bone marrow Plasma Cell-like Multiple Myeloma Genes

| | | | Quantitative Gene Expression | |
|---|---|---|---|---|
| Accession | Symbol | Function | BPC | MM |
| X14850 | H2AX | histone; required for antibody maturation | ++ | +/+++ |
| M29927 | OAT | metabolism; ornithine aminotransferase | ++ | +/+++ |
| S74017 | NFE2L2 | transcription; | ++ | +/+++ |
| HT4604 | GYG | metabolism; glycogen biogenesis | ++ | +/+++ |
| M55531 | SLC2A5 | metabolism; fructose transporter | ++ | +/++++ |
| M60750 | H2BFL | histone; nucleosome | ++ | +/++++ |
| L19437 | TALDO1 | metabolism; transaldolase | ++ | ++/+++ |
| M10901 | NR3C1 | transcription; glucocorticoid receptor | ++ | ++/+++ |
| L41887 | SFRS7 | MRNA splicing factor | ++ | ++/+++ |
| M34423 | GLB1 | metabolism; galactosidase | ++ | ++/++++ |
| X15414 | AKR1B1 | metabolism; aldose reductase | +++ | +/++++ |
| J04456 | LGALS1 | signaling; inhibits CD45 phosphatase | +++ | +/++++ |
| X92493 | PIP5K1B | signaling; kinase | +++ | +/++++ |
| U51478 | ATP1B3 | Na+, K+ transporter | +++ | ++/++++ |
| X91257 | SARS | seryl-tRNA synthetase | +++ | ++/++++ |
| D30655 | EIF4A2 | translation initiation | +++ | ++/++++ |
| D31887 | KIAA0062$^a$ | unknown | +++ | ++/++++ |
| X04106 | CAPN4 | cysteine protease; calcium dependent | +++ | ++/++++ |
| D87442 | NCSTN$^a$ | nicastrin | +++ | ++/++++ |
| L76191 | IRAK1 | signaling; cytokine receptor kinase | +++ | +++/++++ |
| HT1428 | HBB | hemoglobin | ++++ | −/++++ |
| U44975 | COPEB | oncogene; transcription factor | ++++ | −/++++ |
| X55733 | EIF4B | translation initiation | ++++ | +/++++ |
| L09604 | PLP2 | signaling; colonic epithelium differentiation | ++++ | +/++++ |
| HT1614 | PPP1CA | signaling; phosphatase | ++++ | +++/++++ |
| L26247 | SUI1$^a$ | translation initiation; probable | ++++ | +++/++++ |

Accession = GENBANK ® accession number or TIGR database.
Symbol = HUGO approved gene symbol;
$^a$unapproved symbol marked by$^a$.
BPC, bone marrow plasma cells;
AC, absolute call;
AD, average difference.
Quantitative gene expression:
−, AC absent;
+, AC present and AD < 1,000;
++, AD = 1,000 to 5,000;
+++, AD = 5,000 to 10,000;
++++, AD > 10,000.

EXAMPLE 17

Hierachical Cluster Analysis with EDG-MM, LDG-MM1, and LDG-MM2 Reveals Developmental Stage-Based Classification of Multiple Myeloma To identify whether variability in gene expression seen in multiple myeloma (MM) might be used to discern subgroups of disease, hierarchical cluster analysis was performed on 74 newly diagnosed MM, 7 tonsil B cell, 7 tonsil plasma cell, and 7 bone marrow samples using the EDG-MM (FIG. 12), LDG-MM1 (FIG. 13), and LDG-MM2 (FIG. 14). Hierarchical clustering was applied to all samples using 30 of the 50 EDG-MM. A total of 20 genes were filtered out with Max-Min <2.5. This filtering was performed on this group because many of the top 50 EDG-MM showed no variability across MM and thus could not be used to distinguish MM subgroups. A similar clustering strategy was employed to cluster the samples using the 50 LDG-MM1 and 50 LDG-MM2.

The MM samples clustering with the tonsil B cell samples were then identified to determine whether the MM cases clustering with tonsil B cells, or tonsil and bone marrow plasma cells could be correlated with gene expression-defined MM subgroups (Table 16). This data showed that of the MM cases clustering tightly with the tonsil B cell samples, 13 of 22 were from the MM4 subgroup, accounting for a majority of all MM4 cases (13 of 18 MM4 samples). The LDG-MM defined cluster distribution of gene expression-defined MM subgroups was dramatically different in that 14 of the 28 MM samples clustering with the tonsil plasma cell samples were from MM3 subgroup (14 of 15 MM3 samples). LDG-MM2 again showed a strong correlation with the MM subgroups in that 14 of the 20 MM cases in this cluster were from the MM2 subgroup (14 of 21 MM2 cases). Thus, the MM4, MM3, and MM2 subtypes of MM have similarities to tonsil B cells, tonsil plasma cells, and bone marrow plasma cells respectively. MM1 represented the only subgroup with no strong correlations with normal cell counterparts tested here, suggesting that this class has unique characteristics yet to be uncovered.

The distribution of the four MM subgroups in the normal cell cluster groups was determined next (Table 17). The results demonstrate that whereas all MM3 cases were able to be classified, 6 MM1, 5 MM2, and 3 MM4 cases were not clustered with any normal cell group in any of the three cluster analyses. In all samples capable of being clustered, there were strong correlations between gene expression-defined subgroups and normal cell types with the exception of MM1. The data also show that 3 MM1, 2 MM2, 4 MM3, and 1 MM4 cases were found to cluster in two groups. No samples were found in three groups and all cases clustering with two normal classes were always in an adjacent, temporally appropriate groups. P241 was a n exception in that it was clustered in the bone marrow plasma cell and tonsil B cell groups.

Because one of the EDG-MMs was discovered to be cyclin B1 (CCNB1) (Table 13), it was determined if a panel of proliferation association genes recently discovered to be up-regulated in MM4 could be used to advance and validate the classification of MM4 as a so-called tonsil B cell-like form of MM. Box plots of the expression patterns of CCNB1, CKS1, CKS2, SNRPC, EZH2, KNSL1, PRKDC, and PRIM1 showed significant differences across all the groups tested with strong significant correlation between tonsil B cells and MM4 (FIG. 15). Several important observations were made in this analysis. For all the genes, with the exception of SNRPC, there was a progressive reduction in expression in the transition from tonsil B cells to tonsil plasma cells to bone marrow plasma cells. In addition, striking correlations were observed with PRIM1 (FIG. 15). Although PRIM1 expression was significantly different across the entire group ($P=4.25\times10^{-5}$), no difference exists between tonsil B cells and MM4 (Wilcoxon rank sum [WRS] P=0.1), or between tonsil plasma cells and MM3 (WRS P=0.6). Given the important function of several transcription factors in driving and/or maintaining plasma cell differentiation, it was determined if these factors showed altered expression across the groups under study. Although other factors showed no significant changes, XBP1 (FIG. 15) showed an enormous up-regulation between tonsil B cells and tonsil plasma cells as expected. However, the gene showed a reduction in bone marrow plasma cells and a progressive loss across the four MM subgroups with MM4 showing the lowest level ($P=3.85\times10^{-10}$).

Based on conventional morphological features, plasma cells have been thought to represent a homogeneous end-stage cell type. However, phenotypic analysis and gene expression profiling disclosed herein demonstrated that plasma cells isolated from distinct organs can be recognized as belonging to distinct stages of development. Multiple myeloma plasma cells are derived from the bone marrow and are thought to represent a transformed counterpart of normal terminally differentiated bone marrow plasma cells. However, the dramatic differences in survival, which can range from several months to greater than 10 years, suggests that multiple myeloma may represent a constellation of several subtypes of disease. Conventional laboratory parameters have not been particular useful in segregating distinct disease subtypes with sufficient robustness that would allow adequate risk stratification. In addition, unlike achievements in classifying leukemias and lymphomas based on similar nonrandom recurrent chromosomal translocations, the extreme karyotypic heterogeneity of multiple myeloma has made attempts at understanding the molecular mechanisms of the disease and classification prediction virtually impossible.

In studies presented here, it was identified that many EDGs and LDGs exhibit highly variable expression in multiple myeloma, suggesting that multiple myeloma might be amenable to a developmental stage-based classification. It appears from the results of this study that multiple myeloma can in fact be classified based on similarities in gene expression with cells representing distinct stages of B cell differentiation. This developmental based-system in conjunction with the gene expression-based system reported above represents a critical affirmation of the validity of the developmental-based system.

Recent studies provide support for the hypothesis that MM3 represents a tonsil plasma cell-like form of the disease. Microarray profiling with the U95Av2 GeneChip on 150 newly diagnosed patients (including the 74 described here) along with a n analysis of chromosome 13 loss has revealed a significant link between reduced RB1 transcripts with either monosomy or partial deletions of chromosome 13 (unpublished data). In these studies, it was observed that a number of multiple myeloma cases with or without chromosome 13 deletion had RB1 transcripts at levels comparable to those seen in normal tonsil plasma cells. FISH analysis with a bacterial artificial chromosome BAC covering RB1 demonstrated that these cases did not have interstitial deletions of the RB1 locus. Given that RB1 was found to be a LDG-MM1, it was determined if the low levels of RB1 may be linked to tonsil plasma cell-like MM, i.e MM3. Of 35 multiple myeloma cases with RB1 AD values of <1100 (RB1 AD value not less than 1100 in 35 normal bone marrow plasma cell samples tested), 74% belonged to the MM3 class. In contrast, of 38 multiple myeloma cases lacking deletion 13 and having RB1 AD values greater than 1100, only 21% belonged to the MM3 subtype (unpublished data).

Although there is a significant link between the cell development-based classification and gene expression profiling-based classification disclosed herein, there are exceptions in that although as expected the majority of the MM4 cases belonged to the tonsil B cell-cluster subgroup, 5 MM3, 1 MM2, and 3 MM1 cases were also found in this cluster. The recognition that cases within one gene expression-defined subgroup could be classified in two normal cell defined clusters suggests these cases may have intermediate characteristics with distinct clinical outcomes. It is of interest to determine if the unsupervised gene expression-based system or developmental stage-based system alone or in combination will allow the creation of robust risk stratification system. This can be tested by allowing sufficient follow-up time on >150 uniformly treated multiple myeloma cases in which profiling has been performed at diagnosis.

MM1 was the only gene expression-defined subgroup lacking strong similarities to any of the normal cell types analyzed in this study. It is possible that MM1 has similarities to either mucosal-derived plasma cells or peripheral blood plasma cells which has recently been shown to represent a distinct type of plasma cells. Future studies will be aimed at providing a developmental stage position for this subtype.

The hypoproliferative nature of multiple myeloma, with labeling indexes in the clonal plasma cells rarely exceeding 1%, has lead to the hypothesis that multiple myeloma is a tumor arising from a transformed and proliferative precursor cell that differentiates to terminally differentiated plasma cells. It has been shown that there is a bone marrow B cell population transcribing multiple myeloma plasma cell-derived VDJ joined to IgM sequence in IgG- and IgA-secreting multiple myelomas. Other investigations have shown that the clonogenic cell in multiple myeloma originates from a pre-switched but somatically mutated B cell that lacks intraclonal variation. This hypothesis is supported by recent use of single-cell and in situ reverse transcriptase-polymerase chain reaction to detect a high frequency of circulating B cells that share clonotypic Ig heavy-chain VDJ rearrangements with multiple myeloma plasma cells. Studies have also implicated these precursor cells in mediating spread of disease and affecting patient survival.

Links of gene expression patterns between subsets of multiple myeloma and cells representing different late stages of B cell differentiation further support the above hypothesis in that MM4 and MM3 may have origins in a so called "multiple myeloma stem cell". This hypothesis can be tested by isolating B cells from tonsils or lymph nodes or peripheral blood of MM3 and MM4 patients, differentiating them into plasma cells in vitro using a new method described by Tarte et al. (2002) and then testing for the presence of an multiple myeloma gene expression signature within the differentiated populations. Even if the multiple myeloma stem cell represents a minority population in the B cells, the multiple myeloma gene expression signature may be recognized, if not with conventional microarray, then by more sensitive quantitative real-time RT-PCR. A real time RT-PCR method is envisioned as expression profile models using at little as 20 genes that distinguish malignant multiple myeloma plasma cells from normal plasma cells at an accuracy of 99.5% have been developed (unpublished data).

Regardless of the outcome of these experiments, it is clear that gene expression profiling has become an extremely powerful tool in evaluating the molecular mechanisms of plasma cell differentiation and how these events relate to multiple myeloma development and progression, which in turn should provide more rational means of treating this currently fatal disease.

TABLE 16

Distribution of Multiple Myeloma Subgroups in Hierarchical Clusters Defined by EDG-MM, LDG-MM1, and LDG-MM2 Genes

| Normal Cell-Defined Cluster | Gene Expression-Defined MM Subgroups | | | | |
|---|---|---|---|---|---|
| | MM1 (n = 20) | MM2 (n = 21) | MM3 (n = 15) | MM4 (n = 18) | P |
| EDG-MM (n = 22) | 3 | 1 | 5 | 13 | .00005 |
| LDG-MM1 (n = 29) | 8 | 4 | 14 | 3 | .000008 |
| LDG-MM2 (n = 20) | 6 | 14 | 0 | 0 | .000001 |

TABLE 17

Distribution of Gene Expression-Defined Multiple Myeloma Subgroup Cases in Normal Cell Clusters defined by EDG-MM, LDG-MM1, and LDG-MM2

| MM1 | TBC | TPC | BPC | MM2 | TBC | TPC | BPC | MM3 | TBC | TPC | BPC | MM4 | TBC | TPC | BPC |
|---|---|---|---|---|---|---|---|---|---|---|---|---|---|---|---|
| P026 | | Y | Y | P237 | | Y | Y | P052 | Y | Y | | P034 | Y | Y | |
| P037 | | Y | Y | P241 | Y | | Y | P098 | Y | Y | | P051 | Y | | |
| P029 | Y | Y | | P079 | | | Y | P107 | Y | Y | | P057 | Y | | |
| P061 | | Y | | P083 | | | Y | P158 | Y | Y | | P063 | Y | | |
| P066 | | Y | | P121 | | | Y | P119 | | Y | | P065 | Y | | |
| P006 | | Y | | P144 | | | Y | P221 | | Y | | P075 | Y | | |
| P120 | | Y | | P157 | | | Y | P030 | | Y | | P084 | Y | | |
| P131 | | Y | | P171 | | | Y | P043 | | Y | | P122 | Y | | |
| P002 | | | Y | P176 | | | Y | P053 | | Y | | P127 | Y | | |
| P010 | | | Y | P213 | | | Y | P055 | | Y | | P154 | Y | | |
| P067 | | | Y | P215 | | | Y | P138 | | Y | | P187 | Y | | |
| P226 | | | Y | P251 | | | Y | P155 | | Y | | P199 | Y | | |
| P025 | Y | | | P250 | | | Y | P163 | | Y | | P255 | Y | | |
| P082 | Y | | | P222 | | Y | | P239 | | Y | | P054 | | Y | |
| *P085* | | | | P103 | | Y | | P175 | Y | | | P101 | | Y | |
| *P099* | | | | P202 | | Y | | | | | | P056 | | | |
| *P001* | | | | P015 | | | | | | | | *P091* | | | |
| *P016* | | | | *P048* | | | | | | | | *P168* | | | |
| *P036* | | | | P124 | | | | | | | | | | | |
| *P118* | | | | *P212* | | | | | | | | | | | |
| | | | | *P249* | | | | | | | | | | | |

MM1, MM2, MM3, MM4, and PXXX represent gene expression-defined subgroups and patient identifiers, respectively. Y indicates that the case was found in the normal cell-defined cluster. Cases in italics were not found to cluster with any normal cell type. Some cases were found to cluster with two normal cell types. TBC, tonsil B cells; TPB, tonsil plasma cells; BPC, bone marrow plasma cells.

EXAMPLE 18

Diagnostic Models that Distinguish Multiple Myeloma, Monoclonal Gammopathy of Undetermined Significance, And Normal Plasma Cells The molecular mechanisms of the related plasma cell dyscrasias monoclonal gammopathy of undetermined significance (MGUS) and multiple myeloma (MM) are poorly understood. Additionally, the ability to differentiate these two disorders can be difficult. This has important clinical implications because monoclonal gammopathy of undetermined significance is a benign plasma cell hyperplasia whereas MM is a uniformly fatal malignancy. Monoclonal gammopathies are characterized by the detection of a monoclonal immunoglobulin in the serum or urine and underlying proliferation of a plasma cell/B lymphoid clone. Patients with monoclonal gammopathy of undetermined significance have the least advanced disease and are characterized by a detectable plasma cell population in the marrow (<10%) and secretion of a monoclonal protein detectable in the serum (<30 g/L), but they lack clinical features of overt malignancy (such as lytic bone lesions, anemia, or hypercalcemia). Patients with overt MM have increased marrow plasmacytosis (>10%), serum M protein (>30 g/L), and generally present with anemia, lytic bone disease, hypercalcemia, or renal insufficiency.

Approximately 2% of all monoclonal gammopathy of undetermined significance cases will convert to overt multiple myeloma per year, but it is virtually impossible to predict which of these cases will convert. A difficulty in the clinical management of multiple myeloma is the extreme heterogeneity in survival, which can range from as little as two months to greater than eight years with only 20% of this variability being accounted for with current clinical laboratory tests. Thus, there is a great need for more robust methods of classification and stratification of these diseases.

This example reports on the application of a panel of statistical and data mining methodologies to classify multiple myeloma (MM), monoclonal gammopathy of undetermined significance and normal plasma cells. Expressions of 12,000 genes in highly purified plasma cells were analyzed on a high density oligonucleotide microarray. Various methodologies applied to global gene expression data identified a class of genes whose altered expression is capable of discriminating normal and malignant plasma cells as well as classifying some monoclonal gammopathy of undetermined significance as "like" MM and others as "unlike" MM. The extremely high predictive power of this small subset of genes, whose products are involved in a variety of cellular processes e.g., adhesion and signaling, suggests that their deregulated expression may not only prove useful in the creation of molecular diagnostics, but may also provide important insight into the mechanisms of MM development and/or conversion from the benign condition of monoclonal gammopathy of undetermined significance to the overly malignant and uniformly fatal MM.

Six different methodologies were employed herein: logistic regression, decision trees, support vector machines (SVM), Ensemble of Voters with 20 best information gain genes (EOV), naïve Bayes, and Bayesian networks. All six models were run on microarray data derived from Affymetrix (version 5) high density oligonucleotide microarray analysis. One hundred fifty six untreated MM samples, 34 healthy samples and 32 samples designated as monoclonal gammopathy of undetermined significance were compared. The normalization algorithm available from the Affymetrix software was used. Information on normalization and standardization of the microarray data is available on Affymetrix's website.

Statistical and Data Mining Methodologies

Various methods were employed with two goals in mind. The first goal is to identity genes whose over or under expression are apparent in the comparison of healthy samples, monoclonal gammopathy of undetermined significance samples, and malignant MM (multiple myeloma) samples. The second goal is to identify optimal methods for use in analyzing microarray data and specifically methods applicable to analyzing microarray data on samples from MGUS and MM patients. This is the first work that has been done on simultaneously identifying discriminatory genes and creating models to predict and describe the differences between myeloma, monoclonal gammopathy of undetermined significance, and healthy samples.

For each of the methods (and each of the comparisons), a 10-fold cross validation was employed to estimate the prediction error. Using 10-fold cross validation, $\frac{1}{10}^{th}$ of the data was removed (the 'test' data), and the entire model was created using only the remaining 90% of the data (the 'training' data.) The test data were then run through the training model and any misclassifications were noted. Error rates were computed by compiling the misclassifications from each of the 10 independent runs. Empirical results suggest that 10-fold cross validation may provide better accuracy estimates than the more common leave one out cross validation (Kohavi, 1995).

Logistic Regression

The logistic procedure creates a linear model that yields a number between zero and one. This value represents a predictive probability, for example, of being in the multiple myeloma sample (predictive value close to one) or of being in the normal sample (predictive value close to zero). The structure allows for knowledge of the uncertainty in predicting the group membership of future samples. For example, a new sample may be classified with a predictive probability of 0.53 and classified as multiple myeloma, albeit with less confidence than another sample whose predictive probability is 0.99.

Decision Trees

Decision tree induction algorithms begin by finding the single feature that is most correlated with class. For the present discussion, mutual information was used and the classes were multiple myeloma vs. normal, multiple myeloma vs. monoclonal gammopathy of undetermined significance and monoclonal gammopathy of undetermined significance vs. normal. For each feature, the algorithm computes the information gain of the detection and of the optimal split point for the real-valued measure (signal). Information gain is defined as follows: the entropy of a data set is $-p \log_2 p - (1-p) \log_2(1-p)$ where p is the fraction of samples that are of a certain class. A split takes one data set and divides it into two data sets: the set of data points for which the feature has a value below the split point (or a particular nominal value) and the set of data points for which the gene has a value above the split point (or any other nominal value).

Ensembles

Even with pruning, decision trees can sometimes over fit the data. One approach to avoid over fitting is to learn the n best simple decision trees and let these trees vote on each new case to be predicted. The simplest decision tree is a decision stump, a decision tree with a single internal node, or decision node. The "Ensemble of Voters" (EOV) approach is an unweighted majority vote of the top 20 decision stumps, scored by information gain.

Naïve Bayes

Naïve Bayes is so named because it makes the (often) naive assumption that all features (e.g. gene expression levels) are conditionally independent of the given class value (e.g. MM or normal). In spite of this naive assumption, in practice it often works very well. Like logistic regression, naive Bayes returns a probability distribution over the class values. The model simply takes the form of Bayes' rule with the naive conditional independence assumption.

Bayesian Networks

Bayesian networks (Bayes nets) are a very different form of graphical model from decision trees. Like decision trees, the nodes in a Bayes net correspond to features, or variables. For classification tasks, one node also corresponds to the class variable. A Bayes net is a directed acyclic graph (DAG) that specifies a joint probability distribution over its variables. Arcs between nodes specify dependencies among variables, while the absence of arcs can be used to infer conditional independencies. By capturing conditional independence where it exists, a Bayes net can provide a much more compact representation of the joint distribution than a full joint table or other representation. There is much current research into the development of algorithms to construct Bayes net models from data (Friedman et al., 1999; Murphy, 2001; Pe'er et al., 2001.) Bayes nets are proven to be outstanding tools for classification. For example, in KDD Cup 2001, an international data mining competition with over 100 entries, the Bayes net learning algorithm PowerPredictor was the top performer on a data set with strong similarities to microarray data (Cheng et al., 2000). This is the algorithm employed in the present study.

Support Vector Machines

Support vector machines (SVMs) (Vapnik, 1998; Cristianini and Shawe-Taylor, 2000) are another novel data mining approach that has proven to be well suited to gene expression microarray data (Brown et al., 1999; Furey et al., 2000.) At its simplest level, a support vector machine is an algorithm that attempts to find a linear separator between the data points of two classes. Support vector machines seek to maximize the margin, or separation between the two classes. Maximizing the margin can be viewed as an optimization task that can be solved with linear programming techniques. Support vector machines based on "kernel methods" can efficiently identify separators that belong to other functional classes. A commonly used kernel is the Gaussian kernel. Nevertheless, for gene expression microarray data, it has been repeatedly demonstrated empirically that simple linear SVMs give better performance (Brown et al. 1999; Furey et al., 2000) than SVMs with other kernels.

Results

As mentioned, each model was tested using 10-fold cross validation to obtain error (misclassification) rates. For each of 10 runs of the data, 10% of the sample was removed and the prediction model was created. Then, using the created model, the test sample was predicted into groups and the accuracy was recorded. After completing all 10 runs, the accuracy values were accumulated into the following table (Table 18).

TABLE 18

Ten-Fold Cross Validation Results

| % correctly classified | MM | Normal | MM | MGUS | MGUS | Normal |
|---|---|---|---|---|---|---|
| Logistic | 98.72% | 91.18% | 89.1% | 18.8% | 90.63% | 97.06% |
| Trees | 97.44% | 94.12% | 87.18% | 37.5% | 90.63% | 94.12% |
| SVM | 98.72% | 97.06% | 89.10% | 34.38% | 90.63% | 100% |
| Bayes Net | 98.72% | 100% | 93.56% | 34.38% | 90.63% | 97.06% |
| EOV | 98.08% | 100% | 57.69% | 68.75% | 90.63% | 100% |
| Naïve Bayes | 98.08% | 100% | 91.67% | 43.75% | 90.63% | 100% |

There does not appeal to be one methodology that stands out from the rest in terms of predicting group membership. In the difficult classification of multiple myeloma (MM) vs. MGUS, Ensemble of Voters classifies the most MGUS correctly (68.75%), but the fewest multiple myeloma correctly (57.69%.) Using naive Bayes produces the best classification, though it does not seem to be appreciably better than the other methods. All the methods appear to be able to classify multiple myeloma vs. Normal quite well and MGUS vs. Normal almost as well.

To test the difference of accuracy across procedures, a paired t-test was done for the overall correct classification rate for each of the comparisons on each of the folds of the procedures. None of the methods were significantly different ($p \leq 0.05$) except the EOV when compared to the other methods in the MGUS vs. multiple myeloma test. The paired t-tests give p-values between 0.002 and 0.031 (unadjusted for multiple comparisons) for the EOV compared with the other 5 models in the MGUS vs. multiple myeloma test. According to this test, the EOV has a significantly lower rate of correct classification, though it is the most accurate MGUS classifier as shown above. In comparing two groups, this is often the trade off between sensitivity and specificity.

Models for predicting group membership were identified for each method. The models classifying multiple myeloma vs. MGUS had more overlapping genes (17 unique genes) then the models classifying multiple myeloma vs. Normal (12 unique genes) or MGUS vs. Normal (10 unique genes.) A possible explanation for this is that there are probably numerous genes that distinguish multiple myeloma and normal samples because the two groups are quite distinct. However, the genetic similarities between multiple myeloma and MGUS lead to fewer number of genes that are different across the two groups. This dearth of distinguishing genes conditions any good model to contain some of the same limited number of genes. A more detailed discussion of the particular genes is given in the conclusion.

Meta-Voting

As an additional step to improve the prediction capabilities of the method, a "meta" prediction value was calculated. For each of the logistic regression, support vector machine, and Bayes Net procedures, the marginal predicted group was calculated and then a final prediction was given as the top voted group. A sample is classified in a group if at least two of the three methods predict that group. The calculation indicate that the meta voting procedure does not improve the results.

Receiver Operator Characteristic (ROC) Curves

A Receiver Operating Characteristic, (ROC) curve demonstrates the relationship between sensitivity (correct prediction to the more diseased group) and specificity (correct prediction to the less diseased group). FIG. 16 gives the Receiver Operating Characteristic curves for the comparison of MM (multiple myeloma) vs. MGUS classification. The difficult comparison (multiple myeloma vs. MGUS) is challenging for all the methods. For example, naive Bayes has a high sensitivity but at the cost of low specificity. For even mediocre values of specificity, the sensitivity drops off quite rapidly. In order to have a high sensitivity for any of the methods (that is, in order to have very few false positives of multiple myeloma), the ability to predict MGUS accurately (specificity) was compromised.

Prediction of MGUS

The models that classify the multiple myeloma and normal samples into distinct groups may also be able to be used as a predictive model for samples that are not clearly in either group, based on clinical data. As a whole, the MGUS samples are clinically healthy (except for high levels of immunoglobulins) but genetically appear malignant. Applying the multiple myeloma vs. normal model to the MGUS samples will give us an idea as to which group the MGUS samples look more like. Table 19 provides the prediction distribution for the MGUS samples into the multiple myeloma and normal groups based on the model which compared multiple myeloma to normal samples. On average, about 90% of the MGUS samples are classified as multiple myeloma, and about 10% are classified as normal. The possible reason for this is that the 10% who are classified as normal may have longer survival times and less disease progression. Regardless, the similarity of MGUS to multiple myeloma (even in the model that was derived without any MGUS) gives additional evidence that the MGUS is actually genetically much more similar to the multiple myeloma than to the normal samples. From both the prediction of the dichotomous groups and the classification of MGUS samples into the two extreme groups, it can be concluded that the methods are not notably different.

In order to better understand the mechanisms behind the poor classification of the MGUS samples (when compared to multiple myeloma), the number of MGUS classified as multiple myeloma for each of three methods, logistic regression, SVM, and Bayes Net was tabulated. Of the 32 MGUS samples the misclassification rates are given in Table 20. There were 26 MGUS samples misclassified using the logistic procedure; 17 of the 26 were also misclassified using SVM, and 18 of the 26 were misclassified using Bayes Net. This cross tabulation indicates that the misclassified MGUS samples are continuously getting misclassified which lends evidence to a possible subset of MGUS samples that are genetically similar to the multiple myeloma samples.

TABLE 19

MM vs. Normal (predicting MGUS)

| % MGUS classified as: | MM | Normal |
| --- | --- | --- |
| Logistic | 87.5% | 12.5% |
| Trees | 93.75% | 6.25% |
| SVM | 93.75% | 6.25% |
| Bayes Net | 93.75% | 6.25% |
| EOV | 84.37% | 15.63% |
| Naïve Bayes | 93.75% | 6.25% |

TABLE 20

| # MGUS misclassified | Logistic | SVM | Bayes Net |
| --- | --- | --- | --- |
| Logistic | 26 | 17 | 18 |
| SVM |  | 21 | 17 |
| Bayes Net |  |  | 21 |

Discussion

Six different statistical and data mining algorithms were examined for their ability to discriminate normal, hyperplastic, and malignant cells based on the expression patterns of ~12,000 genes. The models were highly accurate in distinguishing normal plasma cells from abnormal cells. However, these models displayed a uniform failure in the discrimination between the hyperplasic cells and malignant cells. A major goal of this study was to develop or modify data mining tools in order to capture a small subset of genes from massive gene expression data sets to accurately distinguish groups of cells, e.g. normal, precancerous, and cancerous cells, with the ultimate goal to create sensitive and reproducible molecular-based diagnostic tests. In addition, future studies can be aimed at using a similar strategy to identify a minimum subset of genes capable of discriminating subgroups of disease for risk stratification and prognostics. This is a particularly important concept for this disease as the overall survival in multiple myeloma is highly variable, with some patients surviving as long as 10 years while others die within several months of diagnosis. Current microarray studies require the isolation of large numbers of cells that necessitate advanced facilities and expertise. The studies described in this example represent the first step toward streamlining this process, as a smaller subset of genes (10-20) with a high predictive power allows for a massive reduction in scale, which in turn will make development of a commercial test more amenable to mass production and hence widespread clinical use.

One possible reason for the inability of the models to discriminate monoclonal gammopathy of undetermined significance from multiple myeloma is that MGUS represents at least two different diseases. This is supported by the overlap in misclassification of MGUS samples as shown in Tables 19-20. In simplistic terms, MGUS can be viewed as a disease that will remain indolent or one that will convert to overt malignancy. Accruing sufficient numbers of stable and progressive MGUS cases along with sufficient follow-up time will help resolve this issue.

The failure of the models to differentiate the two disease types could be related to the limitations of the current methodologies. The microarray profiling utilized here only interrogated ⅓ of the estimated 35,000 human genes (International Human Genome Sequencing Consortium. 2001; Venter et al., 2001), thus it is possible that a whole genome survey would reveal discriminating features. A new Affymetrix U133 GeneChip system which is thought to interrogate all human genes may be used to address this question. It is also possible that a whole genome analysis will reveal no significant differences. This revelation could mean any of a variety of possibilities: (1) there is no genetic difference between the two diseases, (2) only the MGUS that are classified as multiple myeloma are genetically similar to multiple myeloma, and the clinical tests are unable to identify that distinction, (3) the current microarray technology is not specific enough to measure the differences between the two diseases, (4) the methods described above are not appropriate for this type of analysis. If (1) or (2) is true, these results would point to other determinants of an indolent or malignant course such as genetic predisposition or somatic DNA mutations not manifest in gene expression, a unique environmental exposure interacting with these predisposing genetic traits, or a non-tumor cell microenvironment or "soil" that promotes plasma cell growth.

Another goal of this work was to use the models of global gene expression profiling to define critical genetic alterations that accompany the transition of a plasma cell from its normal homeostasis to a benign hyperplasia and from hyperplasia to an overt malignancy. Integration of the data from the six models revealed a group of genes that were found in two or more of the models. For purposes of this study these genes were interpreted to represent the most differentially expressed in these transitions. Ten common genes were identified in the normal to MGUS (monoclonal gammopathy of undetermined significance) comparison with 8 of the genes being down-regulated or shut down in the abnormal cells. A similar phenomenon was seen in the normal versus multiple myeloma comparison with 9 of 12 common genes being down-regulated. This was in contrast to the MGUS versus multiple myeloma comparison where almost half (8 of 18 probe sets representing 17 unique genes) of the probe sets were up-regulated in multiple myeloma. Probes sets for 4 different chemokine genes SCYA23 (Normal vs. MGUS), SDF1 (Normal vs. MM); and SCYC2 and SCYA18 (MGUS vs. MM) were down-regulated in the latter group in each of the 3 comparisons. Two probe sets for SCYA18 were found in the MGUS vs. MM comparison. This is an important validation of SCYA18 gene expression truly being different in the two conditions. Chemokines are important mediators of immune responses and act as soluble factors that induce the migration of specific immune cells to sites of inflammation. The potential significance of the loss of expression of multiple chemokine genes in plasma cell dyscrasias is not understood, but may point to how tumors may suppress anti-tumor immune reactions.

As with SCYA18, two unrelated probe sets for the human homologue of the *Drospohila melangaster* gene frizzled (FZD2) were clown-regulated in the normal to MGUS transition. FZD2 codes for a membrane bound receptor that binds a highly conserved family of soluble ligands known as WNTs. WNT signaling regulates homeotic patterning and cell-fate decisions in multicellular organisms ranging from flies to humans. The Wnt signaling cascade has also been shown to be involved in neoplasia as hyperactivation of the Wnt-1 gene by viral insertional mutagenesis caused spontaneous mammary tumorigenesis in mice. It is suspected that loss of FZD2 expression in MGUS carries potential significance given that expression profiling has revealed deregulated expression of multiple members of the WNT signaling pathway in multiple myeloma and plasma cell leukemia (results shown above; Zhan et al. 2002; De Vos et al., 2001). Results in previous examples presented above also show that a secreted antagonist of WNT signaling, FRZB, exhibits elevated expression in a comparison of normal plasma cells and multiple myeloma (Zhan et al., 2002; De Vos et al., 2001). The concomitant, or possibly sequential, down-regulation of the functional WNT receptor (FZD2) and up-regulation of a decoy receptor strongly suggests that disruption of WNT signaling plays a pathological role in multiple myeloma development. In addition to abnormalities in the receptor and decoy genes the genes for the ligands, WNT5A and WNT10B, have been identified as altered in multiple myeloma (results shown above; Zhan et. al., 2002). Whereas WNT5A is upregulated in multiple myeloma, WNT10B is expressed at high levels in normal plasma cells but not in a majority of multiple myeloma plasma cells (Zhan et. al., 2002). It is of note that recent studies have demonstrated that Wnt-5A, Wnt-2B, Wnt-10B Wnt-11 comprise a novel class of hematopoietic cell regulators Taken together these findings suggests that deregulated autocrine and/or paracrine Wnt signaling may play a pivitol role in plasma cell dyscrasias and that a progressive deregulation of multiple components of the signaling complex may be associated with disease progression from normal plasma cells to hyperplastic, but benign, MGUS then to overt multiple myeloma. In conclusion, it is anticipated that strategies like those employed here will allow the creation of new molecular diagnostic and prognostic tests and should provide useful in sight into the genetic mechanisms of neoplastic transformation.

The following references are cited herein:

Brown et al., Support vector machine classification of microarray gene expression data. UCSC-CRL 99-09, Department of Computer Science, University California Santa Cruz, Santa Cruz, Calif. (1999).

Chauhan et al., *Oncogene* 21:1346-1358 (2002).

Cheng et al., KDD Cup 2001. *SIGKDD Explorations* 3:47-64 (2000).

Cristianini and Shawe-Taylor, An Introduction to Support Vector Machines and other kernel-based learning methods. Cambridge University Press (2000).

De Vos et al., *Blood* 98:771-80 (2001).

Eisen et al., *Proc Natl Acad Sci USA* 95:14863-14868 (1998).

Friedman et al., Learning Bayesian network structure from massive datasets: the "sparse candidate" algorithm. *Proc of the International Conf on Uncertainty in Artificial Intelligence* (1999).

Furey et al., *Bioinformatics* 16:906-914 (2000).

International Human Genome Sequencing Consortium, Initial sequencing and analysis of the human genome. *Nature* 409:860-921 (2001).

Kohavi, A study of cross-validation and bootstrap for accuracy estimation and model selection. *Proceedings of the International Joint Conference on Artificial Intelligence* (IJCAI) (1995).

Murphy, The Bayes Net Toolbox for Matlab. *Computing Science and Statistics: Proceedings of the Interface,* (2001).

Pe'er et al., Inferring Subnetworks from Perturbed Expression Profiles. *Proc of Ninth Intnl Conf on Intelligent Systems for Mol Biol* (2001).

Shaughnessy et al., Blood 96:1505-1511 (2000).

Vapnik, Statistical Learning Theory. John Wiley & Sons (1998).

Venter et al., *Science* 291:1304-51 (2001).

Zhan et al., *Blood* 99:1745-1757 (2002).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for gene expression-based classification for multiple myeloma, comprising:
   extracting total RNA of plasma cells obtained from individuals with newly diagnosed multiple myeloma and control group of healthy individuals:
   isolating total RNA from said plasma cells;
   processing said total RNA for hybridization to a DNA microarray;
   hybridizing said total RNA to a DNA microarray; and
   applying hierarchical clustering analysis to the data obtained from said hybridization, wherein said clustering analysis will classify said individuals with multiple myeloma into one of the four distinct subgroups of multiple myeloma.

2. The method of claim 1, wherein said subgroups of multiple myeloma are MM1, MM2, MM3 and MM4.

3. A method for identifying genes with elevated expression in subsets of multiple myeloma patients, comprising:
   extracting total RNA of plasma cells obtained from individuals with newly diagnosed multiple myeloma;
   isolating total RNA from said plasma cells;
   processing said total RNA for hybridization to a DNA microarray;
   hybridizing said total RNA to a DNA microarray; and
   applying hierarchical clustering analysis to the data obtained from said hybridization, wherein said clustering analysis will identify genes with elevated expression in subgroups of multiple myeloma patients.

4. The method of claim 3, wherein one of said genes has nucleotide sequence of SEQ ID NO: 3.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<221> NAME/KEY: primer_bind
<223> OTHER INFORMATION: primer IGJH2

<400> SEQUENCE: 1
```

```
caatggtcac cgtctcttca                                            20

<210> SEQ ID NO 2
<211> LENGTH: 22
<212> TYPE: DNA
<213> ORGANISM: Artificial Sequence
<220> FEATURE:
<221> NAME/KEY: primer_bind
<223> OTHER INFORMATION: primer MMSET

<400> SEQUENCE: 2
cctcaatttc ctgaaattgg tt                                         22

<210> SEQ ID NO 3
<211> LENGTH: 3829
<212> TYPE: DNA
<213> ORGANISM: Homosapiens
<220> FEATURE:
<223> OTHER INFORMATION: GENBANK Accession Number M64347

<400> SEQUENCE: 3
aaggatggca cagggctggt gccctcggag cgtgtcctgg tggggcccca            50
gcggctgcag gtgctgaatg cctcccacga ggactccggg gcctacagct           100
gccggcagcg gctcacgcag cgcgtactgt gccacttcag tgtgcgggtg           150
acagacgctc catcctcggg agatgacgaa gacggggagg acgaggctga           200
ggacacaggt gtggacacag gggcccctta ctggacacgg cccgagcgga           250
tggacaagaa gctgctggcc gtgccggccg ccaacaccgt ccgcttccgc           300
tgcccagccg ctggcaaccc cactccctcc atctcctggc tgaagaacgg           350
cagggagttc cgcggcgagc accgcattgg aggcatcaag ctgcggcatc           400
agcagtggag cctggtcatg gaaagcgtgg tgccctcgga ccgcggcaac           450
tacacctgcg tcgtggagaa caagtttggc agcatccggc agacgtacac           500
gctggacgtg ctggagcgct ccccgcaccg gcccatcctg caggcggggc           550
tgccggccaa ccagacggcg gtgctgggca gcgacgtgga gttccactgc           600
aaggtgtaca gtgacgcaca gccccacatc cagtggctca agcacgtgga           650
ggtgaatggc agcaaggtgg gcccggacgg cacaccctac gttaccgtgc           700
tcaagacggc gggcgctaac accaccgaca aggagctaga ggttctctcc           750
ttgcacaacg tcacctttga ggacgccggg gagtacacct gcctggcggg           800
caattctatt gggttttctc atcactctgc gtggctggtg gtgctgccag           850
ccgaggagga gctggtggag gctgacgagg cgggcagtgt gtatgcaggc           900
atcctcagct acggggtggg cttcttcctg ttcatcctgg tggtggcggc           950
tgtgaccgtc tgccgcctgc gcagcccccc caagaaaggc ctgggctccc          1000
ccaccgtgca caagatctcc cgcttccccg tcaagcgaca ggtgtccctg          1050
gagtccaacg cgtccatgag ctccaacaca ccactggtgc gcatcgcaag          1100
gctgtcctca ggggagggcc ccacgctggc caatgtctcc gagctcgagc          1150
tgcctgccga cccaaatggg agctgtctc gggcccggct gacccctggc           1200
aagccccttg ggagggctg cttcggccag gtggtcatgg cggaggccat           1250
cggcattgac aaggaccggg ccgccaagcc tgtcaccgta gccgtgaaga          1300
tgctgaaaga cgatgccact gacaaggacc tgtcggacct ggtgtctgag          1350
```

| | |
|---|---|
| atggagatga tgaagatgat cgggaaacac aaaaacatca tcaacctgct | 1400 |
| gggcgcctgc acgcagggcg ggcccctgta cgtgctggtg gagtacgcgg | 1450 |
| ccaagggtaa cctgcgggag tttctgcggg cgcggcggcc cccgggcctg | 1500 |
| gactactcct tcgacacctg caagccgccc gaggagcagc tcaccttcaa | 1550 |
| ggacctggtg tcctgtgcct accaggtggc ccggggcatg gagtacttgg | 1600 |
| cctcccagaa gtgcatccac agggacctgg ctgcccgcaa tgtgctggtg | 1650 |
| accgaggaca acgtgatgaa gatcgcagac ttcgggctgg cccgggacgt | 1700 |
| gcacaacctc gactactaca agaagacaac caacggccgg ctccccgtga | 1750 |
| agtggatggc gcctgaggcc ttgtttgacc gagtctacac tcaccagagt | 1800 |
| gacgtctggt cctttggggt cctgctctgg gagatcttca cgctgggggg | 1850 |
| ctccccgtac cccggcatcc tgtggagga gctcttcaag ctgctgaagg | 1900 |
| agggccaccg catggacaag cccgccaact gcacacacga cctgtacatg | 1950 |
| atcatgcggg agtgctggca tgccgcgccc tcccagaggc ccaccttcaa | 2000 |
| gcagctggtg gaggacctgg accgtgtcct taccgtgacg tccaccgacg | 2050 |
| agtacctgga cctgtcggcg cctttcgagc agtactcccc gggtggccag | 2100 |
| gacacccca gctccagctc ctcaggggac gactccgtgt tgcccacga | 2150 |
| cctgctgccc ccggccccac ccagcagtgg gggctcgcgg acgtgaaggg | 2200 |
| ccactggtcc ccaacaatgt gaggggtccc tagcagccca ccctgctgct | 2250 |
| ggtgcacagc cactcccgg catgagactc agtgcagatg gagagacagc | 2300 |
| tacacagagc tttggtctgt gtgtgtgtgt gtgcgtgtgt gtgtgtgtgt | 2350 |
| gcacatccgc gtgtgcctgt gtgcgtgcgc atcttgcctc caggtgcaga | 2400 |
| ggtaccctgg gtgtccccgc tgctgtgcaa cggtctcctg actggtgctg | 2450 |
| cagcaccgag gggcctttgt tctgggggga cccagtgcag aatgtaagtg | 2500 |
| ggcccacccg gtgggacccc gtggggcagg gagctgggcc cgacatggct | 2550 |
| cggcctctgc cttttgcacca cgggacatca cagggtgcgc tcggcccctc | 2600 |
| ccacaccccaa agctgagcct gcagggaagc cccacatgtc cagcaccttg | 2650 |
| tgcctggggt gttagtggca ccgcctcccc acctccaggc tttcccactt | 2700 |
| cccaccctgc ccctcagaga ctgaaattac gggtacctga agatgggagc | 2750 |
| cttaccttt tatgcaaaag gtttattccg gaaactagtg tacatttcta | 2800 |
| taaatagatg ctgtgtatat ggtatatata catatatata tataacatat | 2850 |
| atggaagagg aaaaggctgg tacaacggag gcctgcgacc ctgggggcac | 2900 |
| aggaggcagg catggccctg ggcggggcgt ggggggggcgt ggagggaggc | 2950 |
| cccagggggtc tcacccatgc aagcagagga ccagggcttt ttctggcacc | 3000 |
| gcagttttgt tttaaaactg gacctgtata tttgtaaagc tatttatggg | 3050 |
| cccctggcac tcttgttccc acccccaac acttccagca tttagctggc | 3100 |
| cacatggcgg agagttttaa tttttaactt attgacaacc gagaaggttt | 3150 |
| atcccgccga tagggacg gccaagaatg tacgtccagc ctgccccgga | 3200 |
| gctggaggat cccctccaag cctaaaaggt tgttaatagt tggaggtgat | 3250 |
| tccagtgaag atatttatt tgctttgtcc tttttcagga gaattagatt | 3300 |

```
tctataggat ttttctttag gagatttatt ttttggactt caaagcaagc        3350
tggtattttc atacaaattc ttctaattgc tgtgtgtccc aggcagggag        3400
acggtttcca gggaggggcc ggccctgtgt gcaggttccg atgttattag        3450
atgttacaag tttatatata tctatatata taatttattg agttttaca         3500 agatgtattt gttgtagact taacacttct tacgcaatgc ttctagagtt        3550
ttatagcctg gactgctacc tttcaaagct tggagggaag ccgtgaattc        3600
agttggttcg ttctgtactg ttactgggcc ctgagtctgg gcagctgtcc        3650
cttgcttgcc tgcagggcca tggctcaggg tggtctcttc ttggggccca        3700
gtgcatggtg gccagaggtg tcacccaaac cggcaggtgc gattttgtta        3750
acccagcgac gaactttccg aaaaataaag acacctggtt gctaacctga        3800
aaaaaaaaaa aaaaaaaaaa aaaaaaaa                                3829
```